US010676772B2

(12) United States Patent
Yang et al.

(10) Patent No.: US 10,676,772 B2
(45) Date of Patent: Jun. 9, 2020

(54) CONTROL OF PROTEIN GLYCOSYLATION BY CULTURE MEDIUM SUPPLEMENTATION AND CELL CULTURE PROCESS PARAMETERS

(71) Applicants: Biogen MA Inc., Cambridge, MA (US); Samsung Bioepis, Yeonsu-gu (KR)

(72) Inventors: William C. Yang, Cary, NC (US); Yao-Ming Huang, Cary, NC (US); Kyle McElearney, Medford, MA (US); Lia Tescione, Cambridge, MA (US); James Lambropoulos, Cambridge, MA (US); An Zhang, Cary, NC (US); Valerie Liu Tsang, Cary, NC (US); Thomas Ryll, Lexington, MA (US); Sangil Lee, Incheon (KR); Dae Sung Lee, Incheon (KR)

(73) Assignees: Biogen MA Inc., Cambridge, MA (US); Samsung Bioepis, Yeonsu-gu (KR)

( * ) Notice: Subject to any disclaimer, the term of this patent is extended or adjusted under 35 U.S.C. 154(b) by 0 days.

(21) Appl. No.: 15/953,746

(22) Filed: Apr. 16, 2018

(65) Prior Publication Data

US 2019/0085369 A1  Mar. 21, 2019

Related U.S. Application Data

(63) Continuation of application No. 15/000,522, filed on Jan. 19, 2016, now Pat. No. 9,944,968, which is a continuation of application No. 14/625,559, filed on Feb. 18, 2015, now abandoned, and a continuation-in-part of application No. PCT/US2014/051727, filed on Aug. 19, 2014.

(60) Provisional application No. 61/867,592, filed on Aug. 19, 2013.

(51) Int. Cl.
C12N 5/18 (2006.01)
C12P 21/00 (2006.01)
C12N 5/00 (2006.01)

(52) U.S. Cl.
CPC .......... *C12P 21/005* (2013.01); *C12N 5/0018* (2013.01); *C12N 2500/20* (2013.01); *C12N 2500/30* (2013.01); *C12N 2500/34* (2013.01); *C12N 2500/40* (2013.01); *C12N 2500/90* (2013.01); *C12N 2501/04* (2013.01); *C12N 2511/00* (2013.01)

(58) Field of Classification Search
CPC .......... C07K 2314/732; C07K 2314/41; C12P 21/05; C12P 21/005; C12N 5/0018; C12N 2500/30; C12N 2500/34; C12N 2500/40
See application file for complete search history.

(56) References Cited

U.S. PATENT DOCUMENTS

| 4,560,655 A | 12/1985 | Baker |
| 4,657,866 A | 4/1987 | Kumar |
| 4,767,704 A | 8/1988 | Cleveland et al. |
| 4,927,762 A | 5/1990 | Darfler |
| 5,122,469 A | 6/1992 | Mather et al. |
| 5,500,362 A | 3/1996 | Robinson et al. |
| 5,821,337 A | 10/1998 | Carter et al. |
| 5,869,046 A | 2/1999 | Presta et al. |
| 7,294,481 B1 | 11/2007 | Fung |
| 9,944,968 B2 | 4/2018 | Yang et al. |
| 2012/0276631 A1 | 11/2012 | Bengea et al. |
| 2016/0237399 A1 | 8/2016 | Yang et al. |

FOREIGN PATENT DOCUMENTS

| WO | WO 87/00195 A1 | 1/1987 |
| WO | WO 87/05330 A1 | 9/1987 |
| WO | WO 90/03430 A1 | 4/1990 |
| WO | WO 99/61650 A1 | 12/1999 |

OTHER PUBLICATIONS

Dove, Dec. 2013; Living large: Scaling up cell culture. On the web at www.sciencemag.org/site/products/lst_20131206.pdf?_ga=2.224280347.1232800455.1563907476-1075437599.1544626516. pp. 1259-1261.*
Janosi et al. 1999; N-linked glycosylation and sialyation of the acid-labile subunit. Journal of Biol. Chem. 274(9): 5292-5298.*
Sokoloski et al. 1986; Alterations in glycoprotein synthesis and guanosine triphosphate levels associated with the differentiation of HL-60 leukemia cells produced by inhibitors of inosine 5'-phosphate dehydrogenase. Cancer Research 46 (5): 2314-2319.*
PCT/US2014/051727, Jan. 21, 2015, International Search Report and Written Opinion.
PCT/US2014/051727, Mar. 3, 2016, International Preliminary Report on Patentability.
International Search Report and Written Opinion for Application No. PCT/US2014/051727 dated Jan. 21, 2015.
International Preliminary Report on Patentability for Application No. PCT/US2014/051727 dated Mar. 3, 2016.
Aplin, J.D. and Wriston, J.C., Jr. "Preparation, Properties, and Applications of Carbohydrate Conjugates of Proteins and Lipids," CRC Critical Reviews in Biochemistry 10(4):259-306, CRC Press, United States (1981).
Barnes, D. and Sato, G., "Methods for Growth of Cultured Cells in Serum-Free Medium," Analytical Biochemistry 102(2):255-270, Academic Press, United States (1980).

(Continued)

*Primary Examiner* — Karen Cochrane Carlson
(74) *Attorney, Agent, or Firm* — Wolf, Greenfield & Sacks, P.C.

(57) ABSTRACT

The present invention pertains to a cell culture medium comprising media supplements that are shown to control recombinant protein glycosylation and/or cell culture in a controlled or modulated (shifted) temperature to control recombinant protein glycosylation and/or cell culture with controlled or modulated seed density to control recombinant protein glycosylation, and methods of using thereof. The present invention further pertains to a method of controlling or manipulating glycosylation of a recombinant protein of interest in a large scale cell culture.

28 Claims, 18 Drawing Sheets

(56) References Cited

OTHER PUBLICATIONS

Figure 2B:
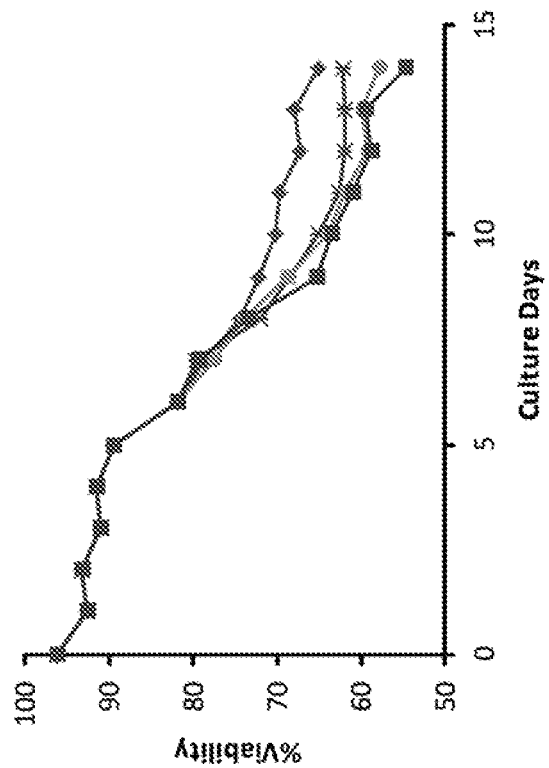

Bertalanffy, P., et al., "Alterations of Endothelial Nucleotide Levels by Mycophenolic Acid Result in Changes of Membrane Glycosylation and E-Selectin Expression," Clinical Chemistry and Laboratory Medicine 37(3):259-264, Walter De Gruyter, Germany (1999).

Edge, A.S.B, et al., "Deglycosylation of Glycoproteins by Trifluoromethanesulfonic Acid," Analytical Biochemistry 118(1):131-137, Academic Press, United States (1981).

Grabenhorst, E., et al., "Genetic Engineering of Recombinant Glycoproteins and the Glycosylation Pathway in Mammalian Host Cells," Glycoconjugate Journal 16(2):81-97, Springer, United States (1999).

Grainger, R.K. and James, D.C., "CHO Cell Line Specific Prediction and Control of Recombinant Monoclonal Antibody N-Glycosylation," Biotechnology and Bioengineering. 110:2970-2983, Wiley Periodicals, United Kingdom (2013).

Ham, R.G., and McKeehan, W.L., "Media and Growth Requirements," in Methods in Enzymology, vol. 58, Jakoby, W.B., and Pastan, I.H., eds., pp. 44-93, Academic Press, Inc., United States (1979).

Huang, M., et al., "Guanine Nucleotide Depletion Inhibits Pre-Ribosomal RNA Synthesis and Causes Nucleolar Disruption," Leukemia Research 32(1):131-141, Pergamon Press, England (2008).

Huang, Y.-M., et al., "Maximizing Productivity of CHO Cell-based Fed-Batch Culture Using Chemically Defined Media Conditions and Typical Manufacturing Equipment," Biotechnology Progress 26(5):1400-1410, Wiley-Blackwell, United States (2010).

James, D.C. and Baker, K.N., "Fermentation, Biocatalysis and Bioseparation," Encyclopedia of Bioprocess Technology, 1336-1349, John Wiley & Sons, United States (1999).

James, D.C., et al., "N-Glycosylation of Recombinant Human Interferon-Gamma Produced in Different Animal Expression Systems," Biotechnology 13(6):592-596, Nature Pub. Co., United States (1995).

Jenkins, N., et al., "Getting the Glycosylation Right: Implications for the Biotechnology Industry," Nature Biotechnology 14(8):975-981, Nature America Publishing, United States (1996).

Kim, K.R., et al., "Recombinant Baculovirus-Based Multiple Protein Expression Platform for Drosophilia S2 cell culture," Journal of Biotechnology. 133:116-122, Elsevier B.V., Netherlands (2008).

Kshirsagar, R., et al., "Controlling Trisulfide Modification in Recombinant Monoclonal Antibody Produced in Fed-Batch Cell Culture," Biotechnology and Bioengineering 109(10):2523-2532, Wiley, United States (2012).

Lifely, M.R., et al., "Glycosylation and Biological Activity of CAMPATH-1H Expressed in Different Cell Lines and Grown Under Different Culture Conditions," Glycobiology 5(8):813-822, IRL Press at Oxford University Press, England (1995).

Luo, Y. and Chen, G., "Combined Approach of NMR and Chemometrics for Screening Peptones Used in the Cell Culture Medium for the Production of a Recombinant Therapeutic Protein," Biotechnology and Bioengineering 97(6):1654-1659, Wiley, United States(2007).

Ma, N., et al., "A Single Nutrient Feed Supports Both Chemically Defined NS0 and CHO Fed-Batch Processes: Improved Productivity and Lactate Metabolism," Biotechnology Progress 25(5):1353-1363, Wiley-Blackwell, United States (2009).

Oliveira, C. and Banerjee, D.K., "Role of Extracellular Signaling on Endothelial Cell Proliferation and Protein N-Glycosylation," J. Cell Physiol. 144:467-472, Wiley-Liss Inc., United States (1990).

Peck, W.A., and Messinger, K., "Nucleoside and Ribonucleic Acid Metabolism in Isolated Bone Cells. Effects of Insulin and Cortisol In Vitro," The Journal of Biological Chemistry 245(10):2722-2729, American Society for Biochemistry and MolecularBiology, United States (1970).

Picard, N., et al., "A Comparison of the Effect of Ciclosporin and Sirolimus on the Pharmacokinetics of Mycophenolate in Renal Transplant Patients," Br. J. Clin. Pharmacol. 62(4):477-484, Blackwell Publishing, England (2006).

Shipkova, M., et al., "The Acyl Glucuronide Metabolite of Mycophenolic Acid inhibits the Proliferation of Human Mononuclear Leukocytes," Transplantation Proceedings 33:1080-1081, Elsevier Science Inc., United States (2001).

Sojar, H.T. and Bahl, O.P., "A Chemical Method for the Deglycosylation of Proteins," Archives of Biochemistry and Biophysics 259(1):52-57 (1987).

Tachibana et al. (1994; Changes of monosaccharide availability of human hybridoma lead to alterations of biological properties of human monoclonalantibody. Cytotechnology 16(3): 151-157.

Thotakura, N.R. and Bahl, O.P., "Enzymatic Deglycosylation of Glycoproteins," Methods in Enzymology 138:350-359, Academic Press, United States (1987).

Xie, L., et al., "Mycophenolic Acid Reverses IgA.sub.1 Aberrant Glycosylation Through Up-Regulating Cosmc Expression in IgA Nephropathy," International Urology and Nephrology 45(2):571-579, Springer Science + Business Media Dordrecht, Germany(2013).

Yu, M., et al., "Understanding the intracellular Effect of Enhanced Nutrient Feeding Toward High Titer Antibody Production Process," Biotechnology and Bioengineering 108(5):1078-1088, Wiley, United States (2011).

Zhang et al., Identifying the differences in mechanisms of mycophenolic acid controlling fucose content of glycoproteins expressed in different CHO cell lines. Biotechnol Bioeng. Nov. 2016;113(11):2367-76. doi: 10.1002/bit.25995. Epub May 11, 2016.

* cited by examiner

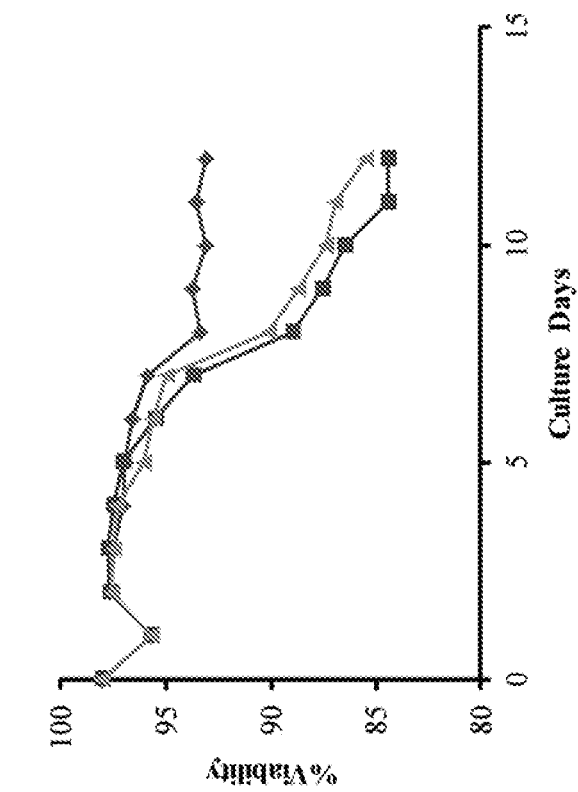
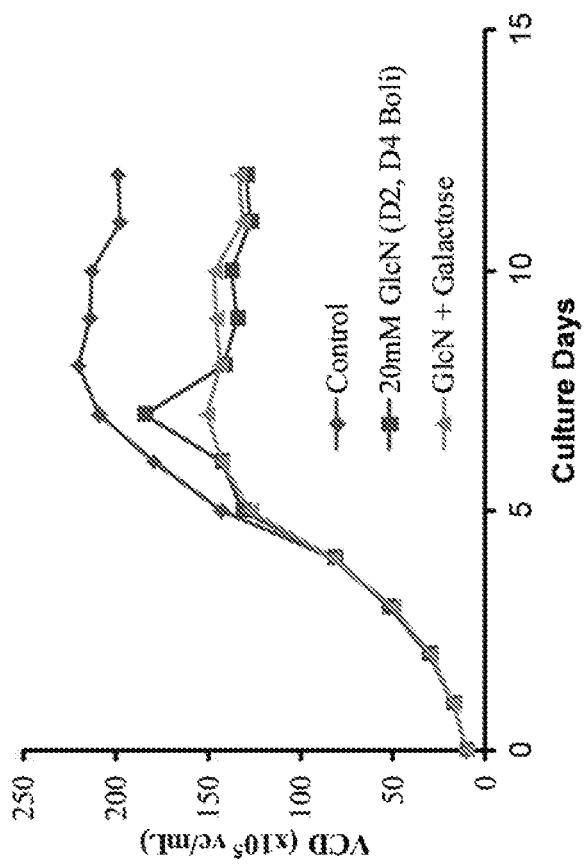
FIG. 1A
FIG. 1B

CONTROL OF PROTEIN GLYCOSYLATION BY CULTURE MEDIUM SUPPLEMENTATION AND CELL CULTURE PROCESS PARAMETERS

This application is a continuation application of U.S. application Ser. No. 15/000,522, filed Jan. 19, 2016 which is a continuation application of U.S. application Ser. No. 14/625,559, filed Feb. 18, 2015 and a continuation-in-part application of International Application No. PCT/US2014/051727, filed Aug. 19, 2014, said International Application No. PCT/US2014/051727 claims the benefit of U.S. Provisional Application No. 61/867,592, filed Aug. 19, 2013, all of which are herein incorporated by reference.

BACKGROUND OF THE INVENTION

Field of the Invention

The present invention pertains to a cell culture medium comprising media supplements that are shown to control recombinant protein glycosylation and/or cell culture in a controlled or modulated (shifted) temperature to control recombinant protein glycosylation, and/or cell culture with a controlled or modulated seed density, and methods of using thereof. The present invention further pertains to a method of controlling or manipulating glycosylation of a recombinant protein of interest in a large scale cell culture, comprising supplementing the cell culture with additives, such as mycophenolic acid, mycophenolic acid acyl glucuronide, insulin, copper II sulfate, glucosamine, galactose, guanine, hypoxanthine, thymidine, or mixtures thereof, and/or controlling or modulating (shifting) the cell culture temperature, and/or controlling or modulating the cell culture seed density, or a combination thereof.

Background Art

Over the last few decades, much research has focused on the production of therapeutic recombinant proteins, e.g., monoclonal antibodies, and the work has taken a variety of angles. While much work in the literature has utilized media containing sera or hydrolysates, chemically defined media were also developed in order to eliminate the problematic lot-to-lot variation of complex components (Luo and Chen, *Biotechnology and Bioengineering* 97(6):1654-1659 (2007)). An improved understanding of the cell culture has permitted a shift to chemically defined medium without compromising on growth, viability, titer, etc. To date optimized chemically defined processes have been reported with titers as high as 7.5-10 g/L (Huang et al., *Biotechnology Progress* 26(5):1400-1410 (2010); Ma et al., *Biotechnology Progress* 25(5):1353-1363 (2009); Yu et al., *Biotechnology and Bioengineering* 108(5):1078-1088 (2011)). In general, the high titer chemically defined processes are fed batch processes with cultivation times of 11-18 days. The process intensification has been achieved without compromising product quality while maintaining relatively high viabilities.

Achievement of a robust, scalable production process includes more than increasing the product titer while maintaining high product quality. The process must also predictably require the main carbohydrate source remain constant, such that the feeding strategy does not need to change across scales. As many processes use glucose as the main carbohydrate, and have lactate and ammonium as the main byproducts, the time course of these three critical chemicals should also scale.

A number of reports have demonstrated mammalian host cell-specific processing of N-glycans associated with recombinant proteins (James et al., Bio/Technology, 13:592-596 (1995); Lifely et al., Glycobiology, 5:813-822 (1995)). These differences may be important for therapeutic proteins as they can directly alter the antigenicity, rate of clearance in vivo, and stability of recombinant proteins (Jenkins et al., Nature Biotechnol. 14:975-981 (1996)). Thus, it is important not only to be able to characterize glycans bound to a therapeutic recombinant protein to predict the consequences for in vivo safety and efficacy, but also to understand the cellular controls underpinning glycan processing in a potential host cell enabling the implementation of appropriate strategies to control cellular glycosylation (Grabenhosrt et al., Glycoconjug. J., 16:81-97 (1999); James and Baker, Encyclopedia of bioprocess technology: Fermentation, biocatalysis and bioseparation. New York: John Wiley & Sons. p. 1336-1349 (1999)).

Thus, there is a need in the art for identification of methods that can predictably control glycosylation of proteins of interest.

BRIEF SUMMARY OF THE INVENTION

The present invention pertains to a method of altering the glycosylation pattern of a recombinant glycoprotein produced in cell culture comprising: culturing eukaryotic cells engineered to express a recombinant glycoprotein of interest in a cell culture medium, wherein the cell culture medium is supplemented with an additive comprising one or more of mycophenolic acid, mycophenolic acid acyl glucuronide, insulin, copper (II) sulfate, hypoxanthine, thymidine, guanine, glucosamine, or galactose; wherein the glycosylation pattern of the recombinant glycoprotein of interest is altered relative to the same recombinant glycoprotein produced by the same cells in the same cell culture medium without the additive.

In another embodiment, the present invention pertains to a method of altering the glycosylation pattern of a recombinant glycoprotein produced in cell culture comprising: culturing eukaryotic cells engineered to express a recombinant glycoprotein of interest in a cell culture medium, wherein the cell culture medium is supplemented with an additive comprising one or more of mycophenolic acid, mycophenolic acid acyl glucuronide, insulin, copper (II) sulfate, hypoxanthine, thymidine, guanine, glucosamine, or galactose; wherein the glycosylation pattern of the recombinant glycoprotein of interest is altered to better resemble the glycosylation pattern of a reference sample of the glycoprotein.

In a further embodiment, the present invention pertains to a method of altering the glycosylation pattern of a recombinant glycoprotein produced in cell culture comprising: supplementing the culture medium of a cell culture of eukaryotic cells engineered to express a recombinant glycoprotein of interest with an additive comprising one or more of mycophenolic acid, mycophenolic acid acyl glucuronide, insulin, copper (II) sulfate, hypoxanthine, thymidine, guanine, glucosamine, or galactose; wherein the glycosylation pattern of the recombinant glycoprotein of interest is altered relative to the same recombinant glycoprotein produced by the same cells in the same cell culture medium without the additive.

In another embodiment, the present invention pertains to a method of altering the glycosylation pattern of a recombinant glycoprotein produced in cell culture comprising: supplementing the culture medium of a cell culture of eukaryotic cells engineered to express a recombinant glycoprotein of interest with an additive comprising one or more of mycophenolic acid, mycophenolic acid acyl glucuronide, insulin, copper (II) sulfate, hypoxanthine, thymidine, guanine, glucosamine, or galactose; wherein the glycosylation pattern of the recombinant glycoprotein of interest is altered to better resemble the glycosylation pattern of a reference sample of the glycoprotein.

In another embodiment, the present invention pertains to a method of altering the glycosylation pattern of a recombinant glycoprotein produced in cell culture comprising: controlling or modulating the cell culture temperature. In one embodiment, the method comprises increasing the cell culture temperature. In another embodiment, the method comprising decreasing the cell culture temperature. In one embodiment the method of altering the glycosylation pattern of a recombinant glycoprotein produced in cell culture comprising controlling or modulating cell culture temperature together with supplementing the culture medium of a cell culture of eukaryotic cells engineered to express a recombinant glycoprotein of interest with an additive comprising one or more of mycophenolic acid, mycophenolic acid acyl glucuronide, insulin, copper (II) sulfate, hypoxanthine, thymidine, guanine, glucosamine, or galactose.

In another embodiment, the present invention pertains to a method of altering the glycosylation pattern of a recombinant glycoprotein produced in cell culture comprising: controlling or modulating the cell culture seed density. In one embodiment, the method comprises increasing the cell culture seed density. In another embodiment, the method comprising decreasing the cell culture seed density. In one embodiment the method of altering the glycosylation pattern of a recombinant glycoprotein produced in cell culture comprising controlling or modulating cell culture seed density together with supplementing the culture medium of a cell culture of eukaryotic cells engineered to express a recombinant glycoprotein of interest with an additive comprising one or more of mycophenolic acid, mycophenolic acid acyl glucuronide, insulin, copper (II) sulfate, hypoxanthine, thymidine, guanine, glucosamine, or galactose.

In one embodiment, the present invention pertains to a method of altering the glycosylation pattern of a recombinant glycoprotein produced in cell culture comprising: controlling or modulating cell culture temperature together with supplementing the culture medium with mycophenolic acid.

In another embodiment, the present invention pertains to a method of altering the glycosylation pattern of a recombinant glycoprotein produced in cell culture comprising: controlling or modulating cell culture temperature together with supplementing the culture medium with mycophenolic acid acyl glucuronide.

In another embodiment, the present invention pertains to a method of altering the glycosylation pattern of a recombinant glycoprotein produced in cell culture comprising: controlling or modulating cell culture seed density together with supplementing the culture medium with mycophenolic acid.

In another embodiment, the present invention pertains to a method of altering the glycosylation pattern of a recombinant glycoprotein produced in cell culture comprising: controlling or modulating cell culture seed density together with supplementing the culture medium with mycophenolic acid acyl glucuronide.

In another embodiment, the present invention pertains to further recovering the recombinant glycoprotein of interest from the cell culture.

In another embodiment, the alteration of the glycosylation pattern of the recombinant glycoprotein of interest comprises one or more of a reduced level of afucosylation, a reduced level of galactosylation, a reduced level of galactose-alpha-1,3-galactose ($\alpha$-gal), a reduced level of N-glycolylneuraminic acid (NGNA), reduced Fc$\gamma$RIIIa binding, reduced antibody-dependent cell-mediated cytotoxicity, or an increased N-glycan charge. In another embodiment, the alteration of the glycosylation pattern of the recombinant glycoprotein of interest comprises reduced level of afucosylation.

In another embodiment, the alteration of the glycosylation pattern of the recombinant glycoprotein of interest comprises one or more of increased level of afucosylation, an increased level of galactosylation, an increased level of galactose-alpha-1,3-galactose ($\alpha$-gal), an increased level of N-glycolylneuraminic acid (NGNA), increased Fc$\gamma$RIIIa binding, increased antibody-dependent cell-mediated cytotoxicity, or an increased N-glycan charge. In one embodiment, the alteration of the glycosylation pattern of the recombinant glycoprotein of interest comprises increased level of afucosylation.

In one embodiment, the alteration of the glycosylation pattern of the recombinant glycoprotein of interest is achieved while minimizing one or more undesirable side effects.

In a preferred embodiment, the present invention pertains to a method of altering the glycosylation pattern of a recombinant glycoprotein produced in cell culture comprising: supplementing the culture medium with mycophenolic acid (MPA), or supplementing the culture medium with mycophenolic acid and insulin, or supplementing the culture medium with mycophenolic acid and galactose, supplementing the culture medium with mycopphenolic acid, insulin and galactose, or mycophenolic acid acyl glucuronide (acMPAG), or supplementing the culture medium with mycophenolic acid and insulin, or supplementing the culture medium with mycophenolic acid acyl glucuronide and galactose, supplementing the culture medium with mycophenolic acid acyl glucuronide, insulin and galactose, or supplementing the culture medium with copper (II) sulfate, or supplementing the culture medium with copper (II) sulfate, galactose and hypoxanthine, or supplementing the culture medium with glucosamine and galactose, or modulated cell culture temperature and supplementing the culture medium with mycophenolic acid, or modulated seed density and supplementing the culture medium with mycophenolic acid, or modulated cell culture temperature and supplementing the culture medium with mycophenolic acid acyl glucuronide, or modulated seed density and supplementing the culture medium with mycophenolic acid acyl glucuronide.

BRIEF DESCRIPTION OF THE DRAWINGS/FIGURES

FIG. 1A and FIG. 1B. Effect of glucosamine and galactose on the growth (FIG. 1A) and viability (FIG. 1B) of fed-batch shake flask cultures. Glucosamine was delivered as two 10 mM boli, each on Day 2 and Day 4 in both the glucosamine alone condition and the glucosamine/galactose combination condition. In the combination condition, galactose was delivered as part of the 5x-concentrated DMEM/F12 feed media at a concentration of 20 g/L in the feed. The Day 14 final concentration of galactose was 6 g/L, due to 30% feeding.

Figure 2A:
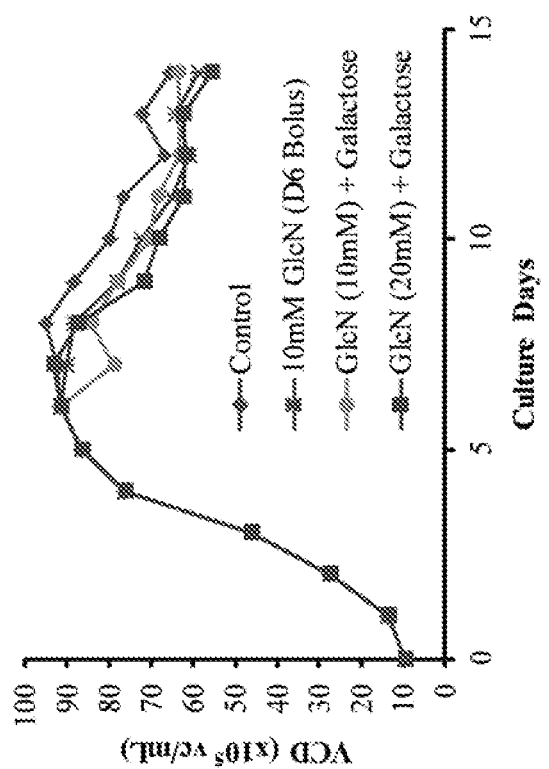

FIG. 2A and FIG. 2B. Effect of glucosamine and galactose on the growth (FIG. 2A) and viability (FIG. 2B) of fed-batch shake flask cultures of immunoadhesin-expressing CHO cells. Glucosamine was delivered as 10 mM boli on Day 6 for the 10 mM conditions and again on Day 8 for the 20 mM condition. In the glucosamine and galactose combination conditions, galactose was delivered as part of the 5×-concentrated DMEM/F12 feed media at a concentration of 20 g/L in the feed. The Day 14 final concentration of galactose was 4 g/L, due to 20% feeding.

Figures 3A, 3B:
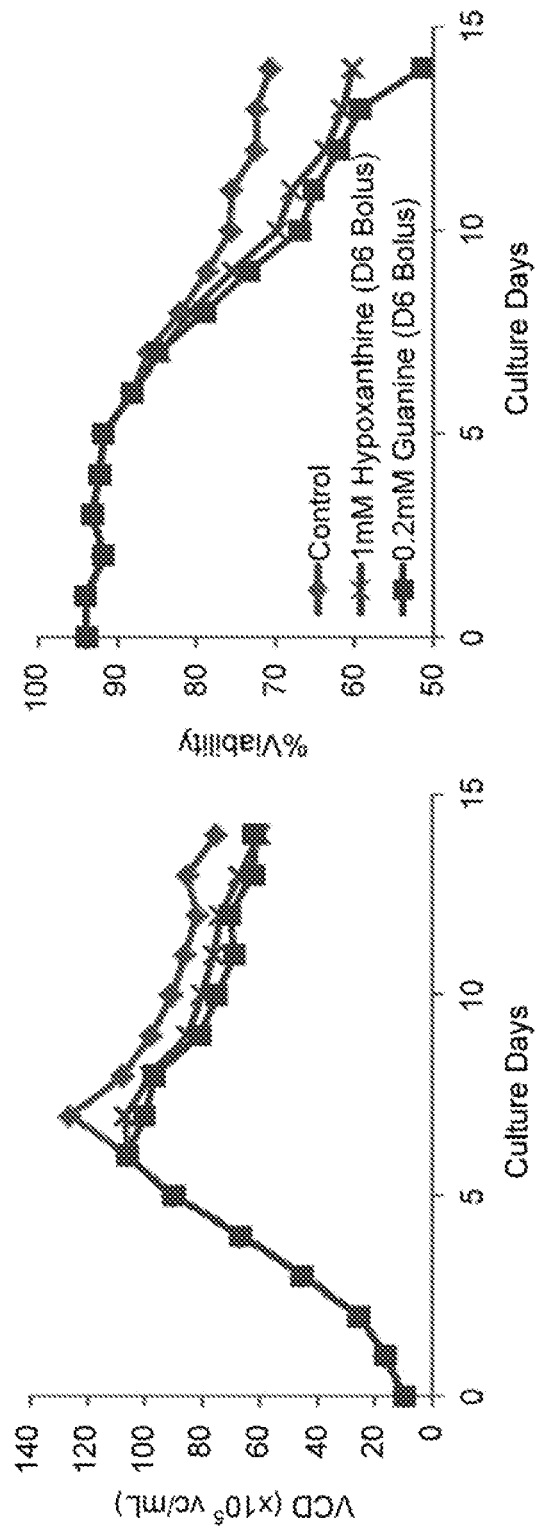

FIG. 3A and FIG. 3B. Effect of hypoxanthine and guanine on the growth (FIG. 3A) and viability (FIG. 3B) of fed-batch shake flask cultures of immunoadhesin-expressing CHO cells. Copper (II) sulfate was delivered as part of the 5×-concentrated DMEM/F12 feed media at a concentration of 1 mM in the feed media. The Day 14 final concentration of $CuSO_4$ in the culture was 0.2 mM due to 20% feeding. Hypoxanthine was delivered as a 1 mM bolus from a 200 mM stock solution on Day 6 after the temperature shift. Guanine was delivered as a 0.2 mM bolus from a 100 mM stock solution on Day 6 after the temperature shift.

Figure 4A:
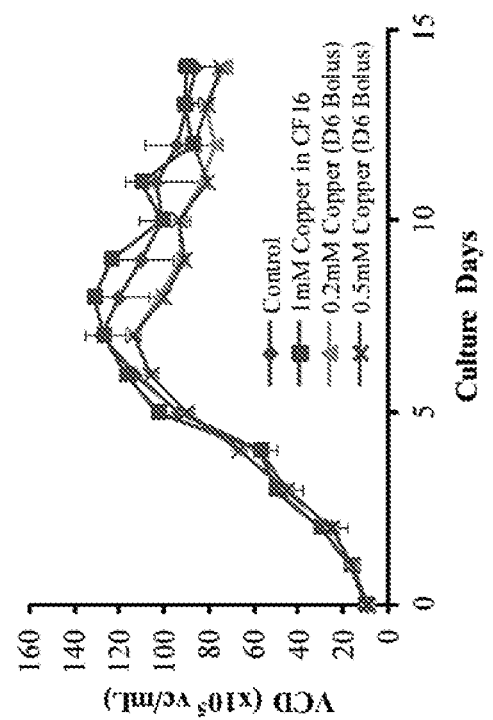
Figure 4B:
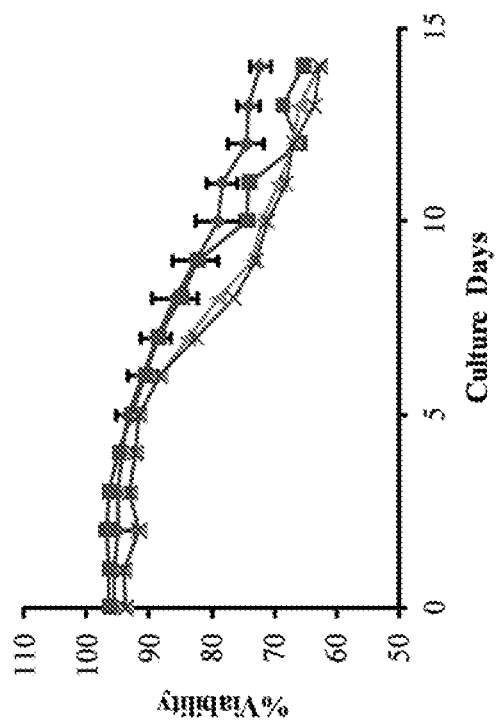

FIG. 4A and FIG. 4B. Effect of copper (II) sulfate on the growth (FIG. 4A) and viability (FIG. 4B) of fed-batch shake flask cultures of immunoadhesin-expressing CHO cells. Copper (II) sulfate was delivered as part of the 5×-concentrated DMEM/F12 feed media at a concentration of 1 mM in the feed media. The Day 14 final concentration of $CuSO_4$ in the culture was 0.2 mM, due to 20% feeding. Alternatively, copper (II) sulfate was delivered as 0.2 mM and 0.5 mM boli on Day 6 from a stock solution.

Figure 5A:
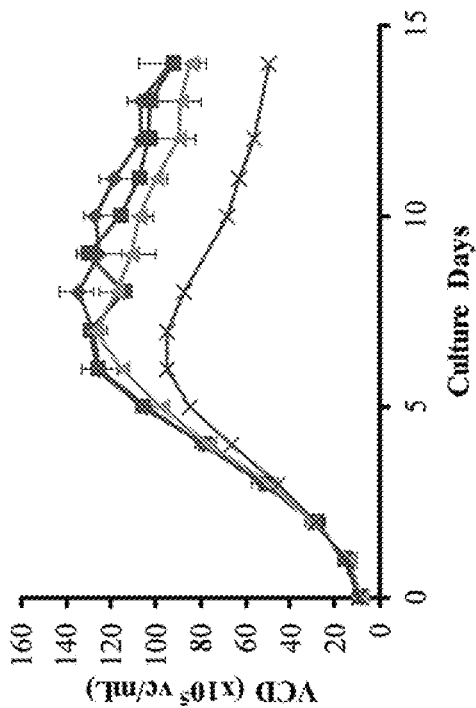
Figure 5B:
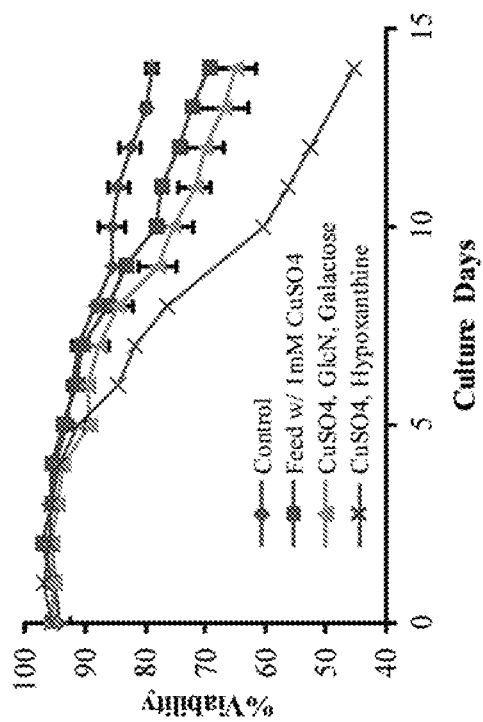

FIG. 5A and FIG. 5B. Effect of copper (II) sulfate, hypoxanthine, glucosamine, and galactose on the growth (FIG. 5A) and viability (FIG. 5B) of 3 L fed-batch bioreactor cultures of immunoadhesin-expressing CHO cells. Copper (II) sulfate was delivered as part of the 5×-concentrated DMEM/F12 feed media at a concentration of 1 mM in the feed media. The Day 14 final concentration of $CuSO_4$ in the culture was 0.25 mM, due to 25% feeding. In the CuSO4, glucosamine, and galactose combination conditions, copper (II) sulfate was delivered as part of the 5×-concentrated DMEM/F12 feed media at a concentration of 1 mM in the feed media. The Day 14 final concentration of $CuSO_4$ in the culture was 0.22 mM, due to 22% feeding. Glucosamine was delivered as two 10 mM boli, each on Day 6 and Day 8. Galactose was delivered as part of the 5×-concentrated DMEM/F12 feed media from Day 6-14 at a concentration of 20 g/L in the feed. The Day 14 final concentration of galactose was 2.4 g/L, due to 12% feeding from Day 6-14. In the $CuSO_4$ and hypoxanthine condition, copper (II) sulfate and hypoxanthine were delivered as part of the 5×-concentrated DMEM/F12 feed media at a concentration of 1 mM and 3 mM, respectively, in the feed media. The Day 14 final concentrations of $CuSO_4$ and hypoxanthine in the culture were 0.23 mM and 0.7 mM, due to 23% feeding.

Figure 6A:
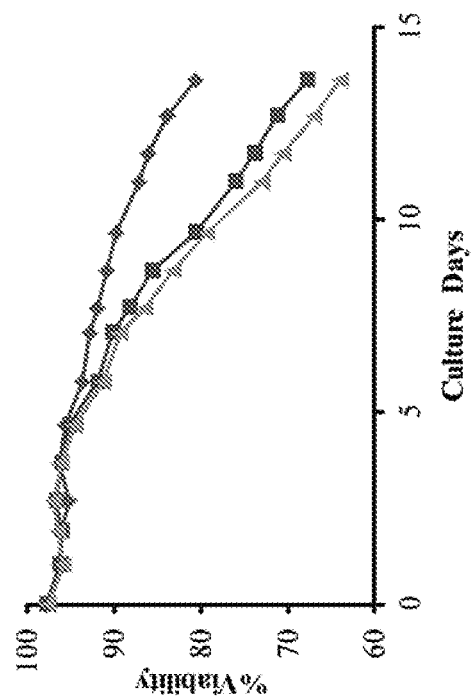
Figure 6B:
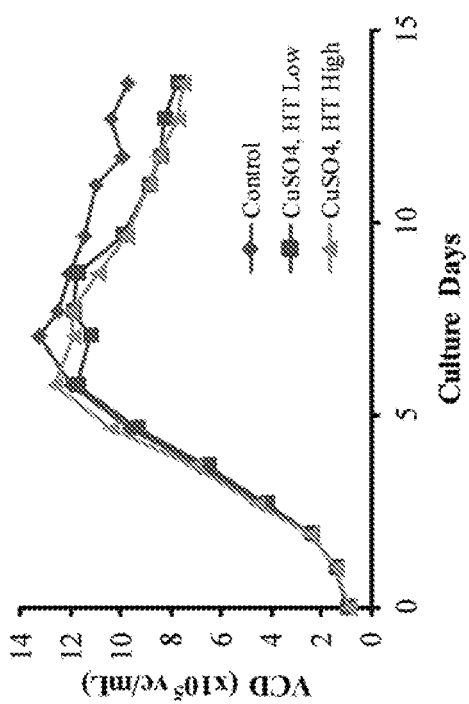

FIG. 6A and FIG. 6B. Effect of copper (II) sulfate and Hypoxanthine-Thymidine (HT) supplement on the growth (FIG. 6A) and viability (FIG. 6B) of immunoadhesin-expressing CHO cells in fed-batch shake flasks. The basal media was glutamine-free CHOM45+10 mg/L insulin and seeded at $9 \times 10^5$ vc/mL. Copper (II) sulfate, hypoxanthine, and thymidine were delivered as part of the 5×-concentrated DMEM/F12 feed media at a concentration of 1 mM, 1 mM, and 0.16 mM respectively in the feed media for the HT Low condition and 1 mM, 3 mM, and 0.5 mM respectively in the feed media for the HT High condition. The Day 14 final concentration of $CuSO_4$, hypoxanthine, and thymidine in the culture was 0.30 mM, 0.30 mM, and 0.05 mM respectively for the HT Low condition and 0.30 mM, 1 mM, and 0.16 mM respectively for the HT High condition due to 30% feeding.

Figure 7A:
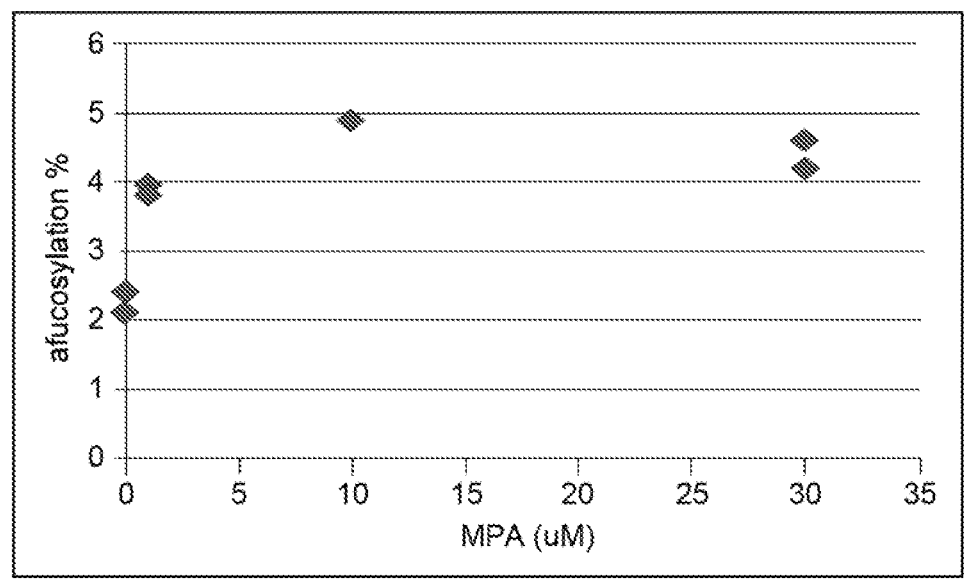
Figure 7B:
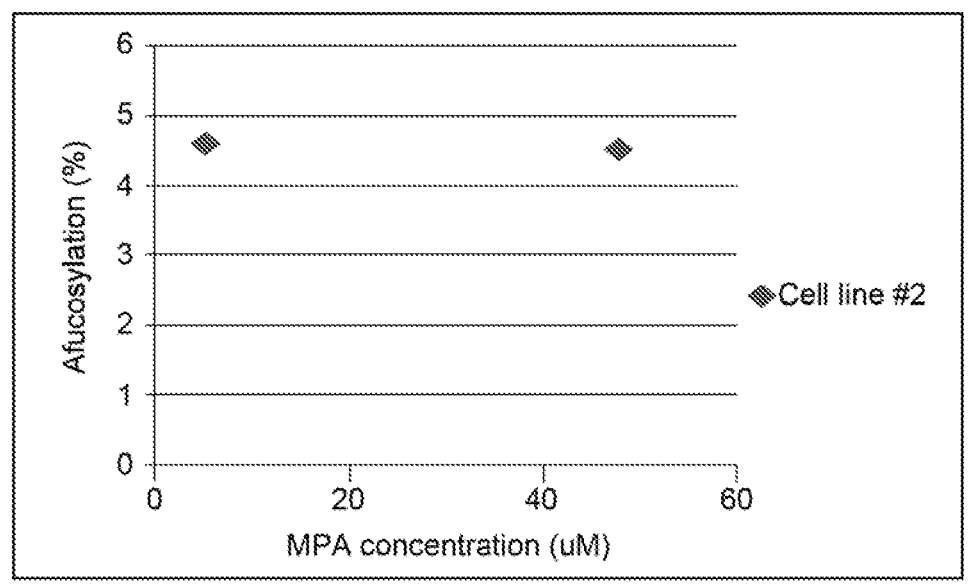

FIG. 7A and FIG. 7B. Impact of Mycophenolic acid (MPA) on afucosylation in cell lines (FIG. 7A and FIG. 7B showing two different cell lines) derived from DUXB11. The cells were cultured in 3 L bioreactor respectively for 7 days following the platform process. On day 7, the cells were divided into several 1 L shake flasks with 200 mL working volume and then dosed with various amounts of MPA (0 µM, 1 µM, 10 µM, 30 µM). After dosing MPA, shake flask fed-batch is conducted until day-3 harvest. Filtered supernatant samples were analyzed for titer and N-glycan analysis for afucosylation level.

Figure 8:
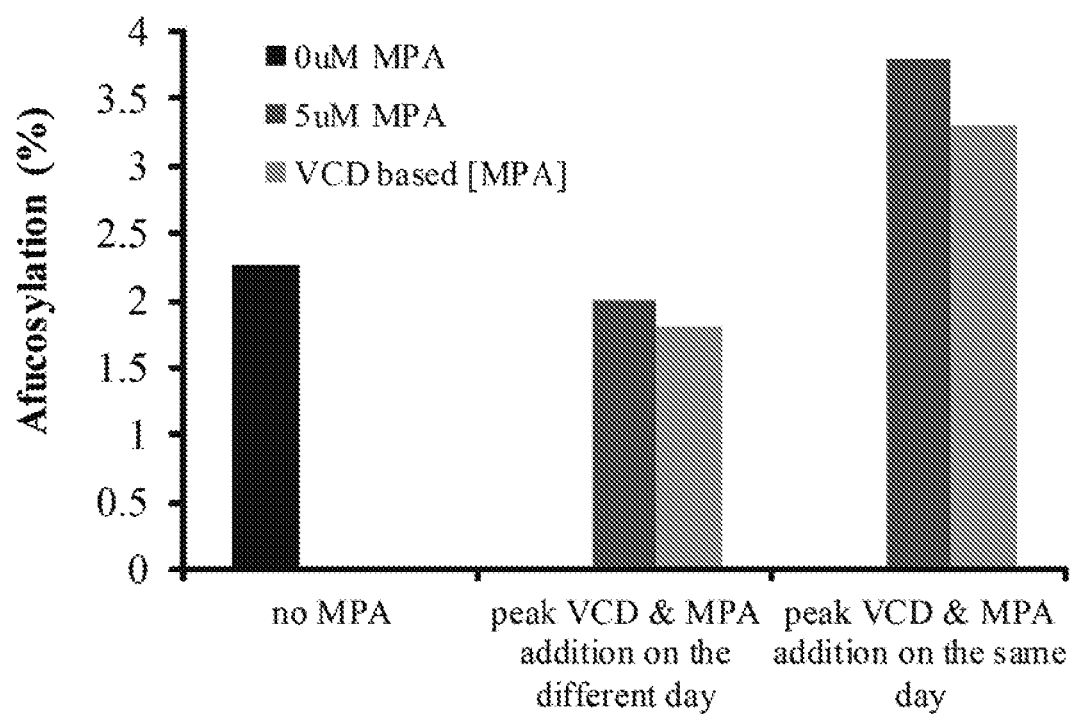

FIG. 8. Impact of the timing of supplementation with Mycophenolic acid (MPA) on afucosylation of DUXB11 cell line in 3 L bioreactors (A, B, C, and D) with the same seed density following the platform process. When the viable cell density (VCD) reached its peak (Day 5 in the study), fixed 5 µM of MPA was added in bioreactor A. At the same time, MPA was added in bioreactor B based on the VCD value to make sure MPA per cell is the same as the platform process to eliminate the possible impact of different cell growth. The next day (one day past peak VCD day, D6 in this study), fixed 5 µM of MPA was added in bioreactor C and MPA was added in bioreactor D based on its D6 VCD value to make sure MPA per cell is the same as the platform process to eliminate the possible impact of different cell growth. All bioreactors were harvested on D13. The filtered supernatant samples were analyzed for titer and N-glycan analysis for afucosylation level.

Figure 9A:
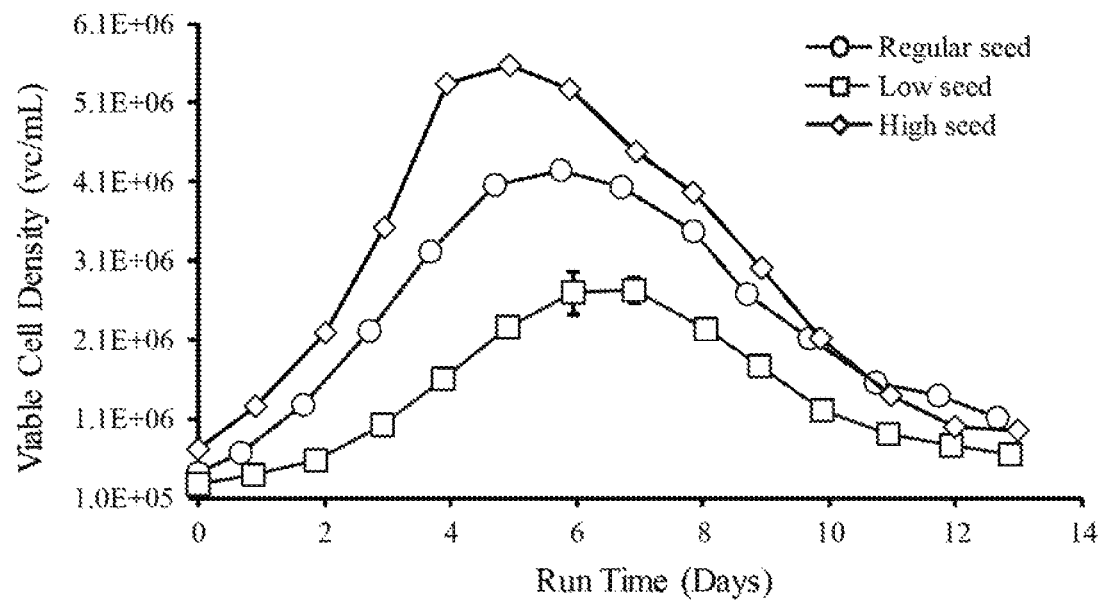
Figure 9B:
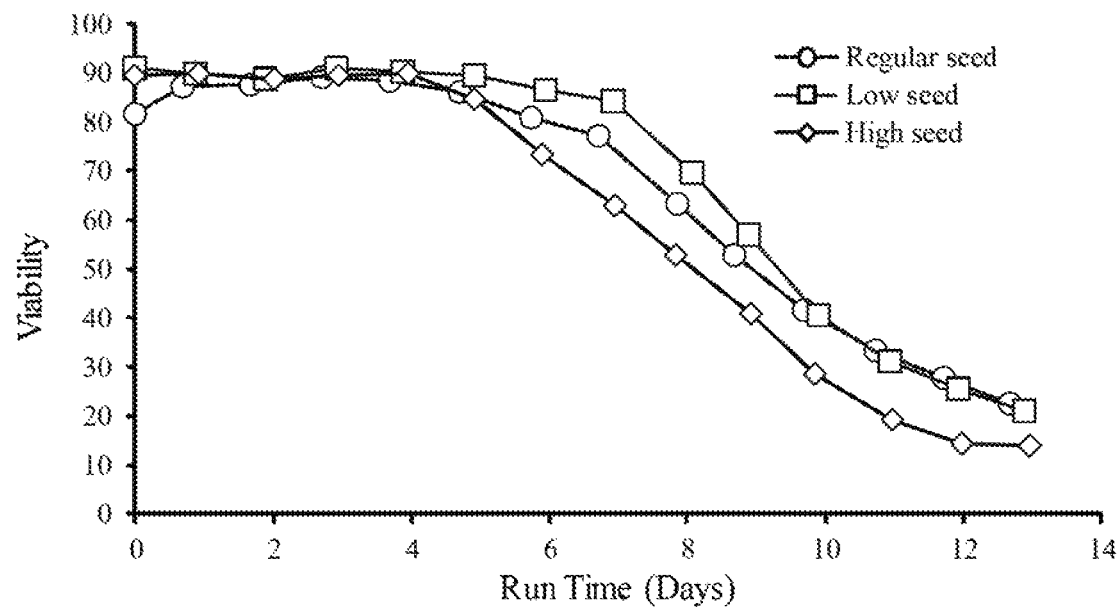

FIG. 9A and FIG. 9B. Impact of seed density growth (FIG. 9A) and viability (FIG. 9B) of DUXB11 cell line that was cultured in 3 L bioreactors. The cells were grown with different seed densities (low, regular, high) following the platform process. Fixed 5 µM of MPA was added on Day 5 in all bioreactors. Different cell performances were observed due to different seed density.

Figure 10:
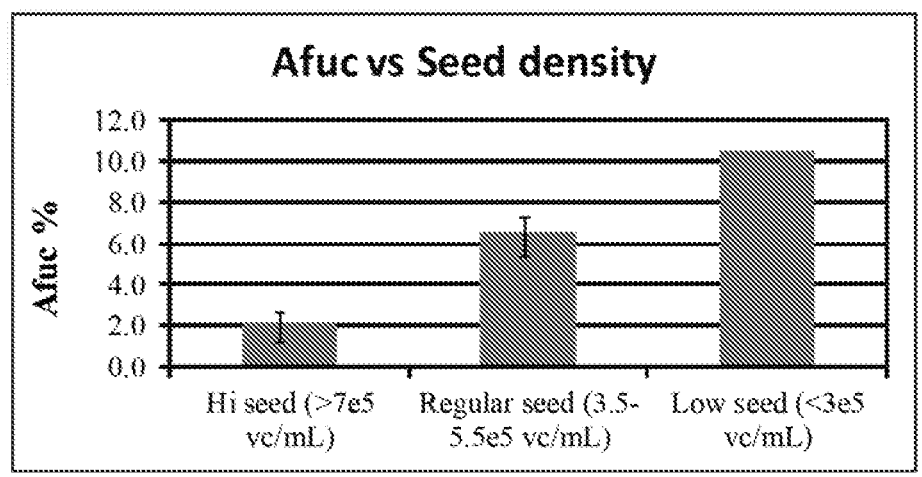

FIG. 10. Impact of seed density on afucosylation in DUXB11 cell line that was cultured in 3 L bioreactors. The cells were grown with different seed densities (low, regular, high) following the platform process. Fixed 5 µM of MPA was added on Day 5 in all bioreactors. Different cell performances were observed due to different seed density. Filtered supernatant samples were analyzed for titer and N-glycan analysis for afucosylation level.

Figure 11:
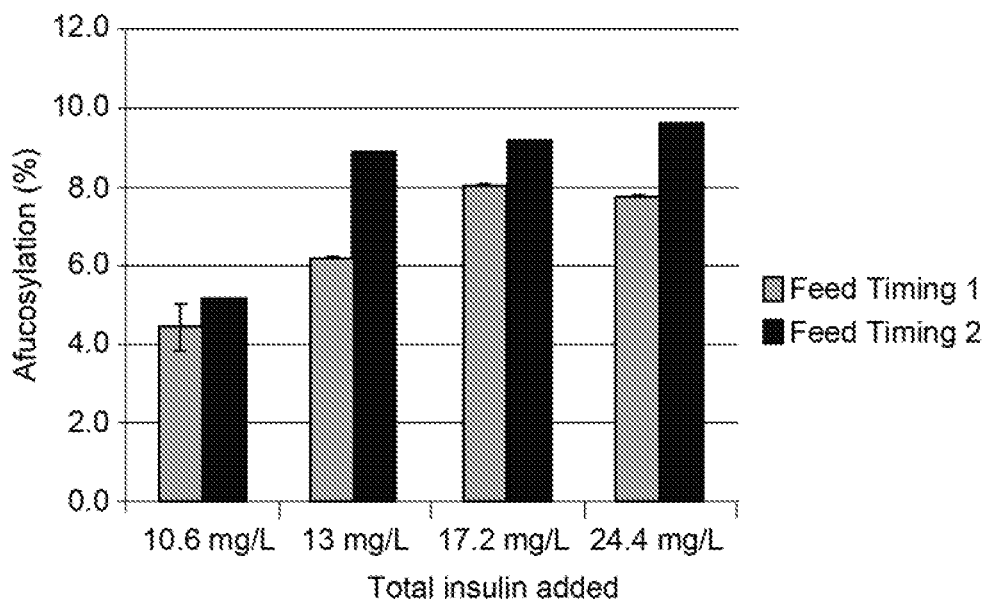

FIG. 11. Impact of insulin on afucosylation on DUXB11 cell line. The cells was cultured in several 3 L bioreactors with the different insulin concentration additions following the platform process. Fixed 5 µM of MPA was added on Day 9 in all bioreactors and harvested on the same day. Filtered supernatant samples were analyzed for titer and N-glycan analysis for afucosylation level.

Figure 12:
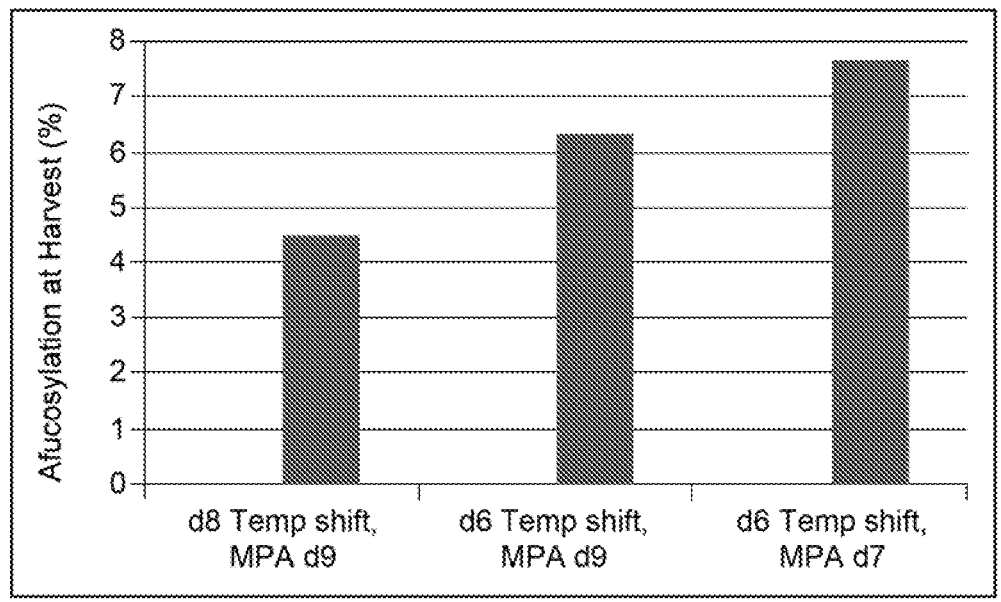

FIG. 12. Impact of timing of temperature shift on afucosylation.

Figure 13:
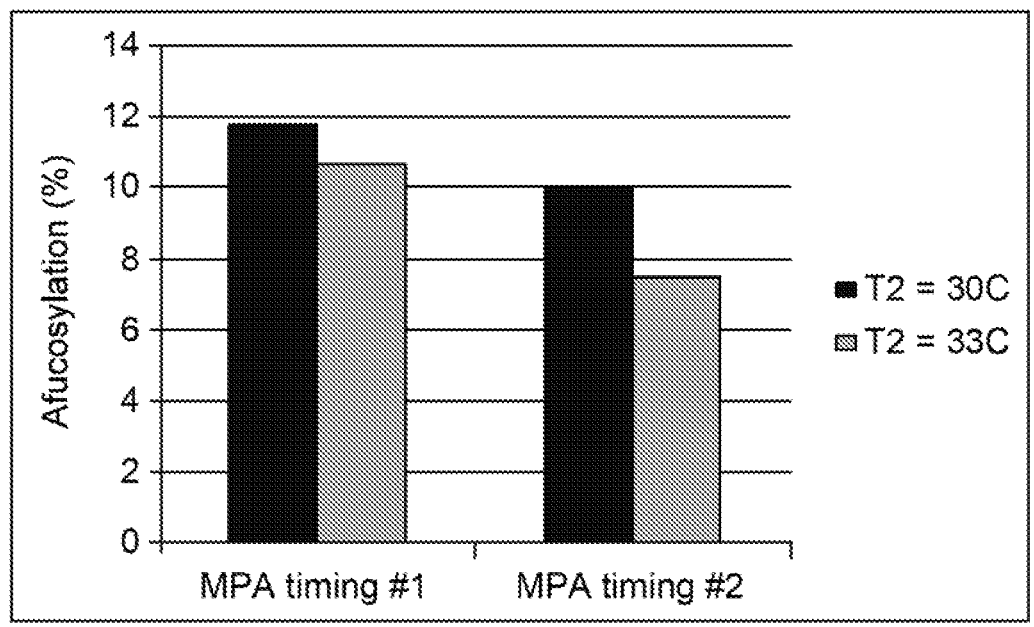

FIG. 13. Impact of timing of temperature shift on afucosylation.

Figure 14A:
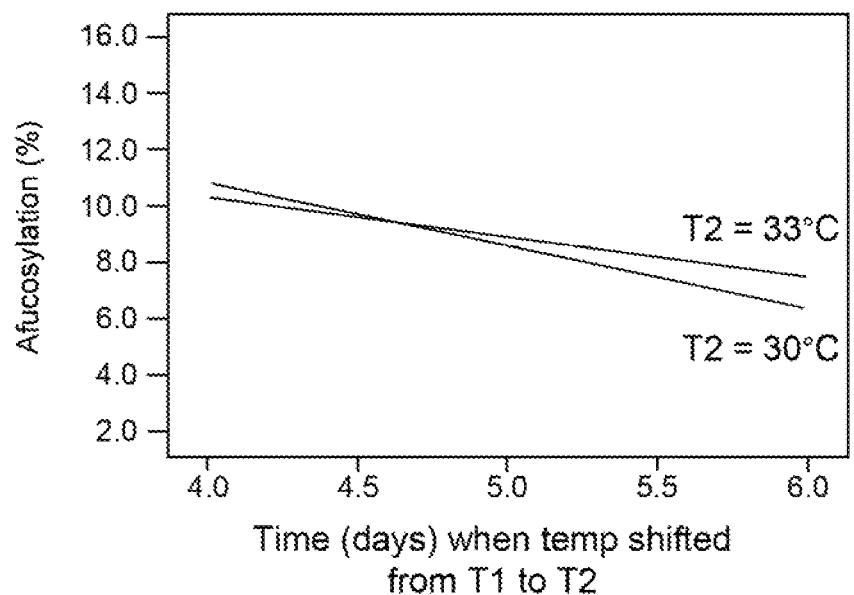
Figure 14B:
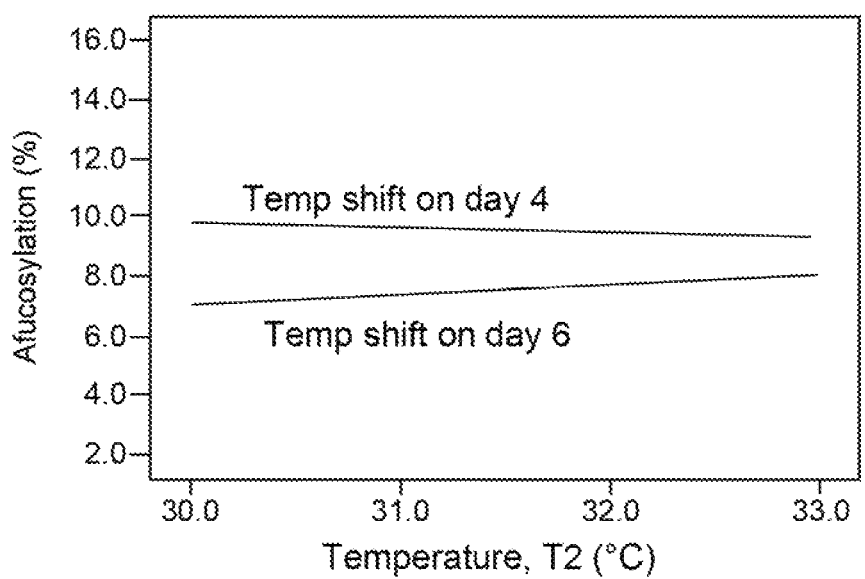
Figure 15A:
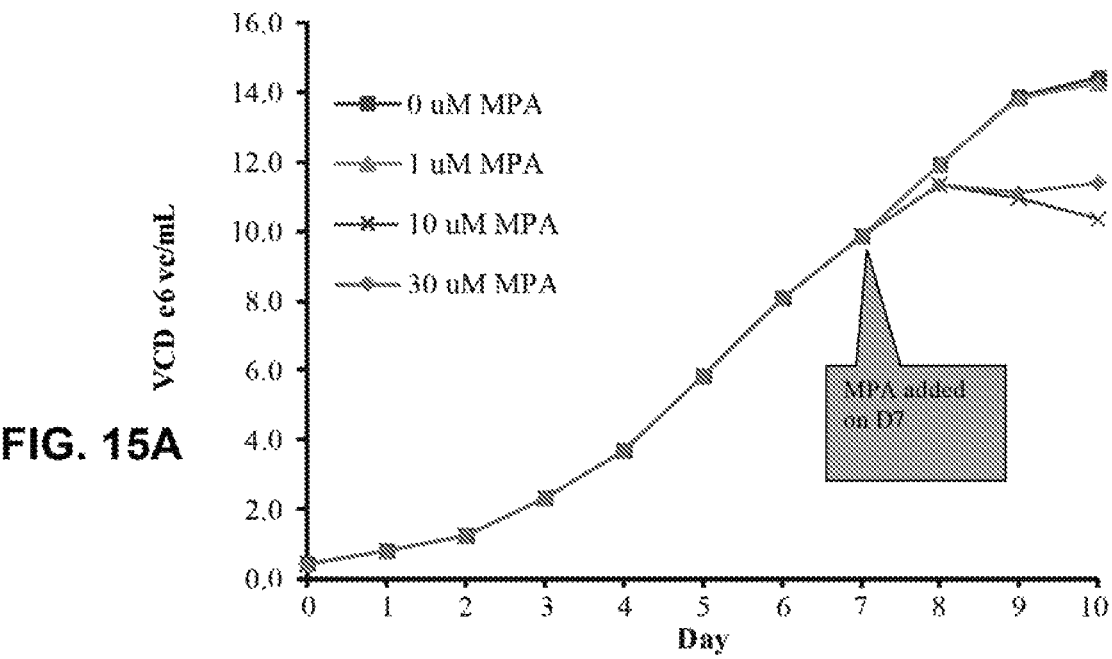
Figure 15B:
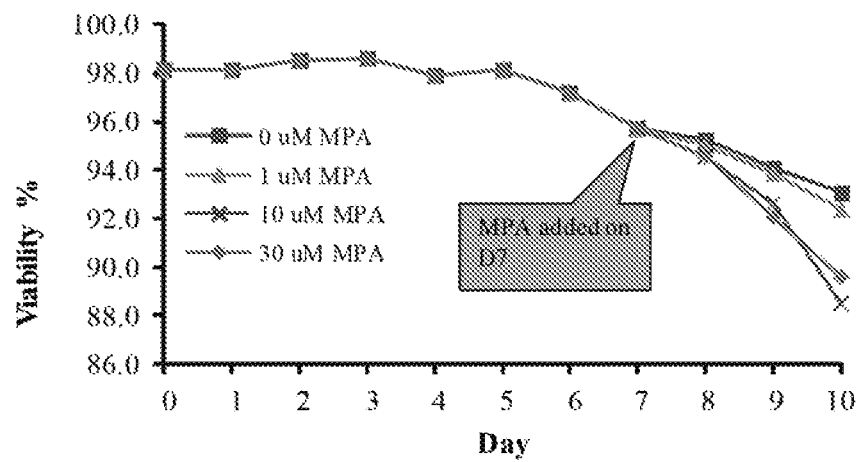
Figure 15C:
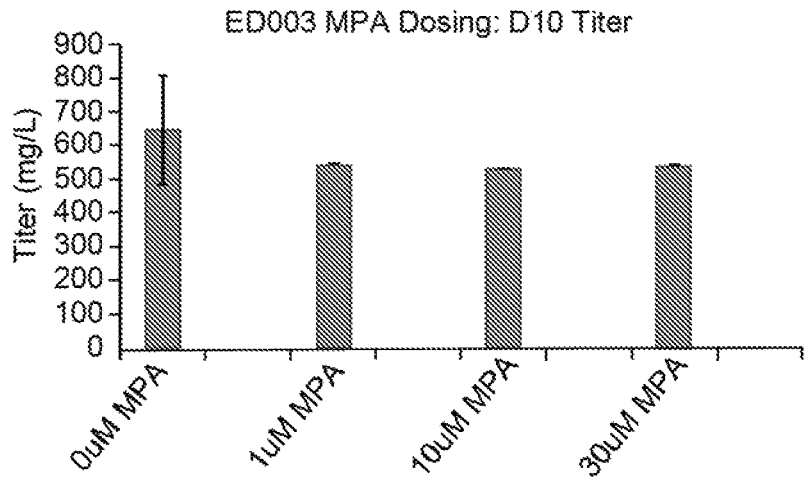
Figure 16A:
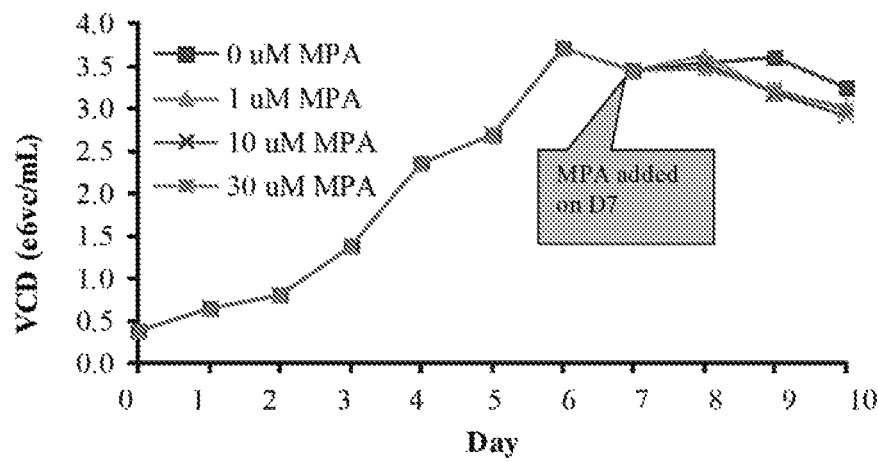
Figure 16B:
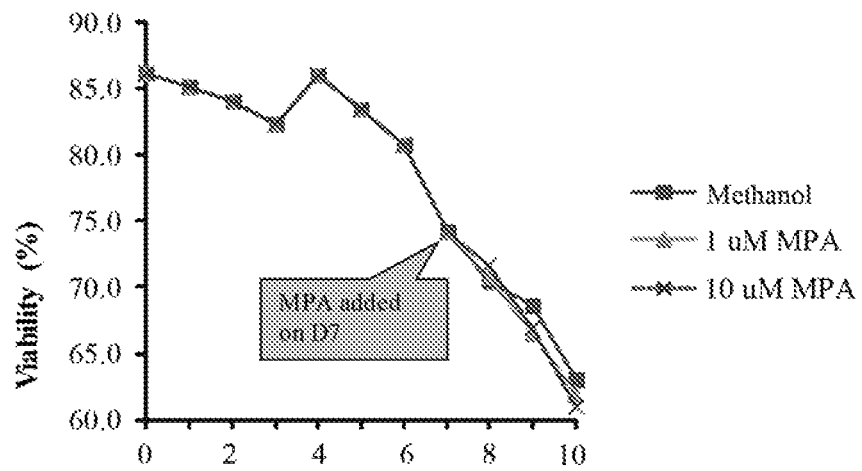
Figure 16C:
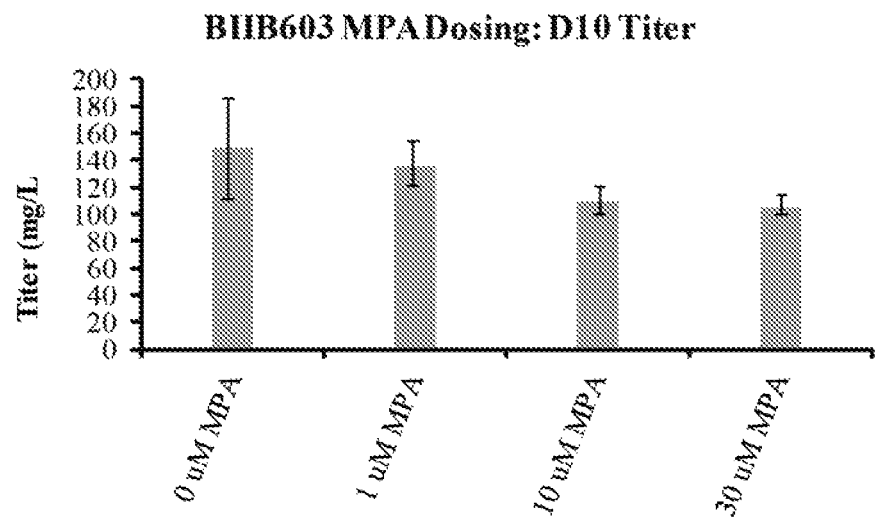

FIG. 14A and FIG. 14B. Factorial DOE study showing impact of timing of temperature shift on afucosylation. FIG. 14A shows afucosylation level after temperature shift on various days. FIG. 14B shows afucosylation level after shifting to various temperatures on days 4 and 6.

FIG. 15A-FIG. 15C and FIG. 16A-FIG. 16C. Impact of Mycophenolic acid (MPA) on growth (FIG. 15A), viability (FIG. 15B), and titer (FIG. 15C) of ED003 cells in a shake flask. Impact of Mycophenolic acid (MPA) on growth (FIG. 16A), viability (FIG. 16B), and titer (FIG. 16C) of BIIB603 cells in a shake flask.

Figure 17A:
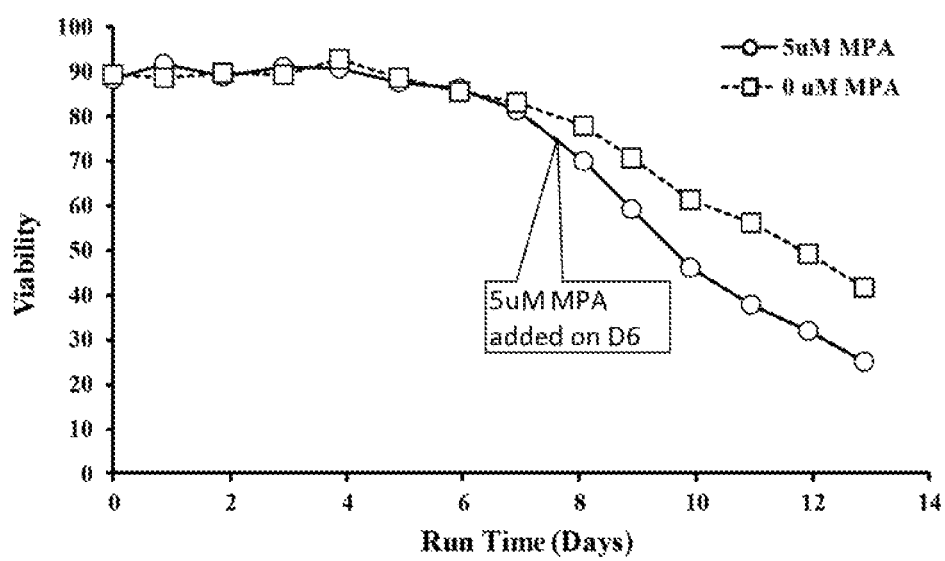
Figure 17B:
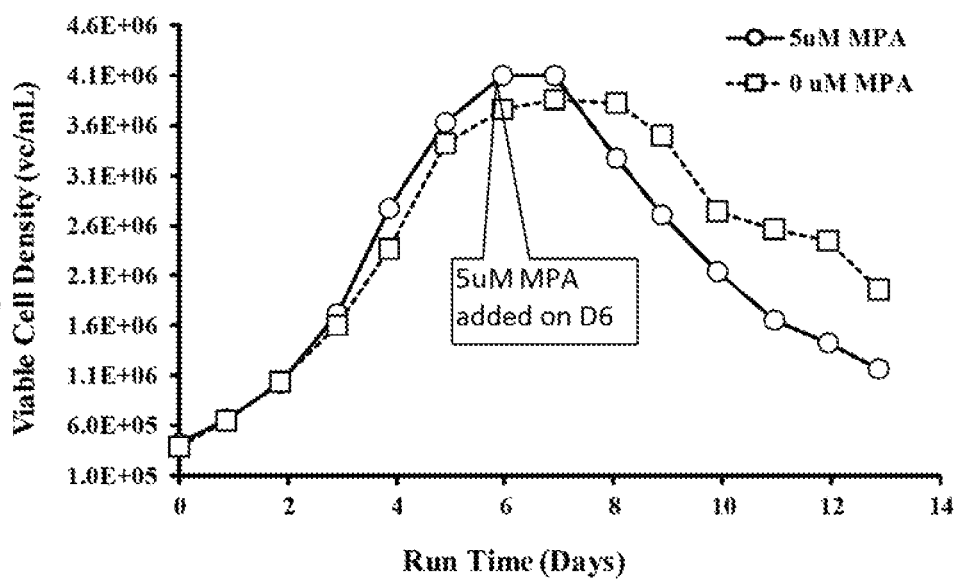
Figure 17C:
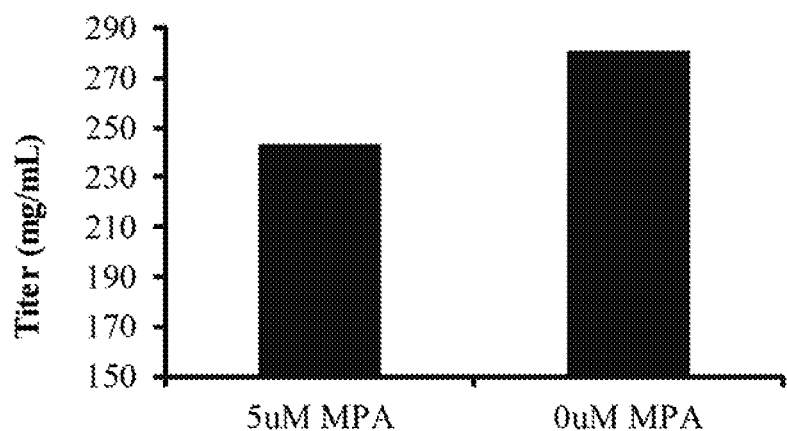

FIG. 17A-FIG. 17C. Impact of Mycophenolic acid (MPA) on viability (FIG. 17A), growth (FIG. 17B), and titer (FIG. 17C) in a bioreactor.

Figure 18:
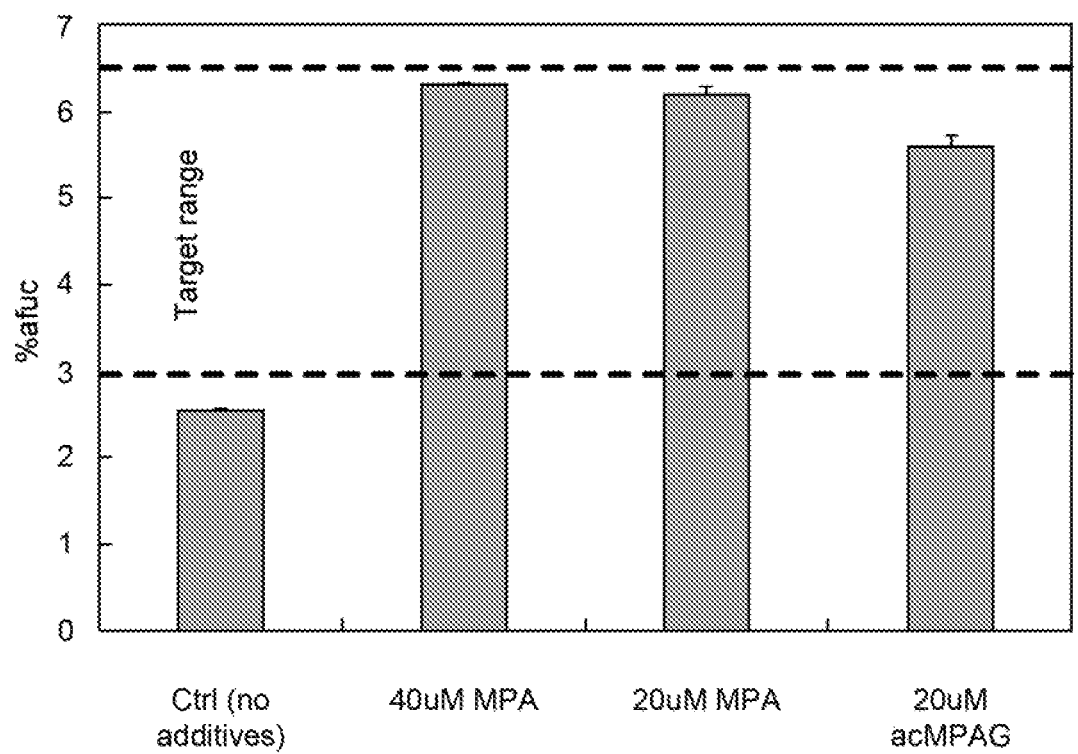

FIG. 18. Impact of Mycophenolic acid (MPA) and Mycophenolic acid acyl glucuronide (acMPAG) on afucosylation in BIIB603 cell line. The cells were scaled up to 5 L BR for fed-batch production process. On day 5, temperature was shifted from 37° C. to 31° C. On day 6, cell culture was drained from the bioreactor and divided into several 500 mL shake flasks with 100 mL working volume and then dosed with various amounts of MPA (0 µM, 20 µM, 40 µM) or acMPAG (20 µM) in duplicates. After dosing, the shake flasks were cultured another 4 days at 31° C., 5% $CO_2$ and 150 rpm with fed-batch process and then harvested. The supernatant was sent for PQ assay (N-glycan analysis) for afucosylation level.

DETAILED DESCRIPTION OF THE INVENTION

The present invention is based on the recognition that cell culture media supplemented with mycophenolic acid, mycophenolic acid acyl glucuronide, insulin, copper (II) sulfate, hypoxanthine, thymidine, guanine, glucosamine (GlcN), galactose, or mixtures thereof provide the ability to control and manipulate the glycolsylation patterns of recombinant glycoproteins produced in eukaryotic cell cultures. The present invention is also based on the recognition that a change in the cell culture temperature or cell culture seed density provides the ability to control and manipulate the glycosylation patterns of recombinant glycoproteins produced in the eukaryotic cell cultures. Such glyclosylation patterns include, without limitation, the level of afucosylation, the level of galactosylation, the level of N-glycan charge, the level of N-glycolylneuraminic acid (NGNA), the level of galactose-alpha-1,3-galactose (α-gal), the level of antibody-dependent cell-mediated cytotoxicity (ADCC), and/or the level of FcγRIIIa binding. As the culture supplements have differential effects on both glycosylation patterns and culture conditions, addition of the various supplements alone or in combination can be used as levers to control and/or manipulate glycosylation patterns while minimizing undesirable side effects, such as detrimental effects on cellular productivity.

The present invention is also applicable to modifying the glycosylation of a recombinant glycoprotein of interest such that it falls within the quality attribute ranges for the desired product. For example, the present invention is applicable to modifying the glycosylation of a recombinant glycoprotein of interest to more closely resemble, match, or substantially match the glycosylation pattern of a reference sample of the same glycoprotein. Differences between various manufacturing processes can result in glycoproteins with identical amino acid sequences having different glycosylation patterns depending on, for example, conditions for growth, cell line used to express the glycoprotein, etc. Provided herein are methods for adjusting, altering, manipulating or changing the glycosylation pattern of a recombinant glycoprotein of interest comprising culturing eukaryotic cells engineered to express the recombinant glycoprotein of interest in cell culture media that has been supplemented with an additive comprising one or more of mycophenolic acid, mycophenolic acid acyl glucuronide, insulin, copper (II) sulfate, hypoxanthine, thymidine, guanine, glucosamine, galactose, or mixtures thereof, or culturing eukaryotic cells engineered to express the recombinant glycoprotein of interest in a cell culture with a controlled or modulated (shifted) temperature, or culturing eukaryotic cells engineered to express the recombinant glycoprotein of interest in a cell culture with a controlled or modulated seed density, or culturing eukaryotic cells engineered to express the recombinant glycoprotein of interest in cell culture with a controlled or modulated (shifted) temperature and a cell culture media that has been supplemented with an additive comprising one or more of mycophenolic acid, mycophenolic acid acyl glucuronide, insulin, copper (II) sulfate, hypoxanthine, thymidine, guanine, glucosamine, galactose, or mixtures thereof, or culturing eukaryotic cells engineered to express the recombinant glycoprotein of interest in cell culture with a controlled or modulated seed density and a cell culture media that has been supplemented with an additive comprising one or more of mycophenolic acid, mycophenolic acid acyl glucuronide, insulin, copper (II) sulfate, hypoxanthine, thymidine, guanine, glucosamine, galactose, or mixtures thereof. According to the methods provided herein, any given cell culture can be adjusted using these components, either alone or in combination as levers to achieve or approach a desired glycosylation pattern while at the same time minimizing undesirable side effects.

I. Definitions

As used in this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

It is understood that wherever embodiments are described with the language "comprising," otherwise analogous embodiments described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various embodiments of the disclosure, which can be had by reference to the specification as a whole. Accordingly, the terms defined immediately below are more fully defined by reference to the specification in its entirety.

The terms "polypeptide" or "protein" as used herein refers a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. If a single polypeptide is the discrete functioning unit and does require permanent physical association with other polypeptides in order to form the discrete functioning unit, the terms "polypeptide" and "protein" as used herein are used interchangeably. If discrete functional unit is comprised of more than one polypeptide that physically associate with one another, the term "protein" as used herein refers to the multiple polypeptides that are physically coupled and function together as the discrete unit.

The term "glycoprotein" refers to a polypeptide or protein coupled to at least one carbohydrate moiety, e.g., a polysaccharide or an oligosaccharide, that is attached to the protein via an oxygen-containing or a nitrogen-containing side chain of an amino acid residue, e.g., a serine or threonine residue ("O-linked") or an asparagine residue ("N-linked"). The term "glycan" refers to a polysaccharide or an oligosaccharide, e.g., a polymer comprised of monosaccharides. Glycans can be homo- or heteropolymers of monosaccharide residues, and can be linear or branched.

As used herein, the "glycosylation pattern" of a recombinant glycoprotein of interest refers to various physical characteristics of the glycoprotein's polysaccharides or oligosaccharides, such as, e.g., the quantity and quality of various monosaccharides present, the degree of branching, and/or the attachment (e.g., N-linked or O-linked). The "glycosylation pattern" of a glycoprotein can also refer to the functional characteristics imparted by the glycoprotein's oligosaccharides and polysaccharides. For example, the extent to which the glycoprotein can bind to FcγRIIIa and induce antibody-dependent cellular cytotoxicity (ADCC).

"Fucosylation" refers to the degree and distribution of fucose residues on polysaccharides and oligosaccharides, for example, N-glycans, 0-glycans and glycolipids. Therapeutic glycoproteins, e.g., antibodies or Fc fusion proteins, with non-fucosylated, or "afucosylated" N-glycans exhibit dramatically enhanced antibody-dependent cellular cytotoxicity (ADCC) due to the enhancement of FcγRIIIa binding capacity without any detectable change in complement-dependent cytotoxicity (CDC) or antigen binding capability. In certain situations, e.g., cancer treatment, non-fucosylated or "afucosylated" antibodies are desirable because they can achieve therapeutic efficacy at low doses, while inducing high cellular cytotoxicity against tumor cells, and triggering high effector function in NK cells via enhanced interaction with FcγRIIIa. In other situations, e.g., treatment of inflammatory or autoimmune diseases, enhanced ADCC and FcγRIIIa binding is not desirable, and accordingly therapeutic glycoproteins with higher levels of fucose residues in their N-glycans can be preferable. As used herein, the term "% afucose" refers to the percentage of non-fucosylated N-glycans present on a recombinant glycoprotein of interest. A higher % afucose denotes a higher number of non-fucosylated N-glycans, and a lower % afucose denotes a higher number of fucosylated N-glycans.

"Sialylation" refers to the type and distribution of sialic acid residues on polysaccharides and oligosaccharides, for example, N-glycans, O-glycans and glycolipids. Sialic acids are most often found at the terminal position of glycans. Sialylation can significantly influence the safety and efficacy profiles of these proteins. In particular, the in vivo half-life of some biopharmaceuticals correlates with the degree of oligosaccharide sialylation. Furthermore, the sialylation pattern can be a very useful measure of product consistency during manufacturing.

The two main types of sialyl residues found in biopharmaceuticals produced in mammalian expression systems are N-acetyl-neuraminic acid (NANA) and N-glycolyl-neuraminic acid (NGNA). These usually occur as terminal structures attached to galactose (Gal) residues at the non-reducing terminii of both N- and O-linked glycans.

"Galactosylation" refers to the type and distribution of galactose residues on polysaccharides and oligosaccharides. Galactose refers to a group of monosaccharides which include open chain and cyclic forms. An important disaccharide form of galactose is galactose-alpha-1,3-galactose (α-gal).

The term "undesirable side effects" refers to certain aspects and results of glycosylation which, under certain circumstances, are to be minimized or avoided. In certain aspects, a side effect to be reduced or avoided is a substantial increase in the level of α-gal. In another aspect a side effect to be reduced or avoided is a substantial reduction in sialic acid levels. In various aspects the methods described herein achieve certain glycosylation patterns without substantially affecting culture density, cell viability level, or both. In certain aspects, a "side effect" which might be undesirable in one glycoprotein, e.g., an decrease in fucose levels (increases ADCC and FcγRIIIa binding) in an antibody used to treat an inflammatory disease, might be desirable in another glycoprotein, e.g., in an antibody used to treat cancer.

The term "antibody" is used to mean an immunoglobulin molecule that recognizes and specifically binds to a target, such as a protein, polypeptide, peptide, carbohydrate, polynucleotide, lipid, or combinations of the foregoing etc., through at least one antigen recognition site within the variable region of the immunoglobulin molecule. As used herein, the term encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, monovalent or monospecific antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively.

As used herein, the term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Recombinantly expressed glycoprotein" and "recombinant glycoprotein" as used herein refer to a glycoprotein expressed from a host cell that has been genetically engineered to express that glycoprotein. The recombinantly expressed glycoprotein can be identical or similar to glycoproteins that are normally expressed in the mammalian host cell. The recombinantly expressed glycoprotein can also foreign to the host cell, i.e. heterologous to peptides normally expressed in the mammalian host cell. Alternatively, the recombinantly expressed glycoprotein can be chimeric in that portions of the glycoprotein contain amino acid sequences that are identical or similar to glycoproteins normally expressed in the mammalian host cell, while other portions are foreign to the host cell. In certain embodiments, the recombinant glycoprotein comprises at least a portion of: an antibody, an immunoadhesin, a Transforming Growth Factor (TGF) beta superfamily signaling molecule, a blood clotting factor, combinations thereof, or fragments thereof. As used herein, the terms "recombinantly expressed glycoprotein" and "recombinant glycoprotein" also encompasses an antibody produced by a hybridoma.

The term "expression" or "expresses" are used herein to refer to transcription and translation occurring within a host cell. The level of expression of a product gene in a host cell can be determined on the basis of either the amount of corresponding mRNA that is present in the cell or the amount of the protein encoded by the product gene that is produced by the cell. For example, mRNA transcribed from a product gene is desirably quantitated by northern hybridization. Sambrook et al., Molecular Cloning: A Laboratory Manual, pp. 7.3-7.57 (Cold Spring Harbor Laboratory Press, 1989). Protein encoded by a product gene can be quantitated either by assaying for the biological activity of the protein or by employing assays that are independent of such activity, such as western blotting or radioimmunoassay using antibodies that are capable of reacting with the protein. Sambrook et al., Molecular Cloning: A Laboratory Manual, pp. 18.1-18.88 (Cold Spring Harbor Laboratory Press, 1989).

"Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 can be performed. Useful effector cells for such assays include peripheral blood mononuclear cells (PBMC) and Natural Killer (NK) cells. Alternatively, or additionally, ADCC activity of a molecule of interest may be assessed in vivo, e.g., in an animal model such as that disclosed in Clynes et al. PNAS (USA) 95:652-656 (1998).

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells and neutrophils. The effector cells may be isolated from a native source thereof, e.g. from blood or PBMCs.

"Fc receptor" or "FcR" describes a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, e.g., as described in Gazzano-Santoro et al., J. Immunol. Methods 202:163 (1996), may be performed. Polypeptide variants with altered Fc region amino acid sequences (polypeptides with a variant Fc region) and increased or decreased C1q binding capability are described, e.g., in U.S. Pat. No. 6,194,551 B1 and WO 1999/51642. See also, e.g., Idusogie et al. J. Immunol. 164: 4178-4184 (2000).

The term "basal media formulation" or "basal media" as used herein refers to any cell culture media used to culture cells that has not been modified either by supplementation, or by selective removal of a certain component.

As used herein, the terms "additive" or "supplement" refer to any supplementation made to a basal medium to achieve the goals described in this disclosure. An "additive" or "supplement" can include a single substance, e.g., mycophenolic acid, mycophenolic acid acyl glucuronide, insulin, copper II sulfate, or can include multiple substances, e.g., copper II sulfate, hypoxanthine, and thymidine; mycophenolic acid and insulin; mycophenolic acid and galactose; mycophenolic acid, galactose, and insulin; mycophenolic acid acyl glucuronide and insulin; mycophenolic acid acyl glucuronide and galactose; or mycophenolic acid acyl glucuronide, galactose, and insulin. The terms "additive" or "supplement" refer to the all of the components added, even though they need not be added at the same time, and they need not be added in the same way. For example, one or more components of an "additive" or "supplement" can be added as a single bolus or two or more boli from a stock solution, while other components of the same "additive" or "supplement" can be added as part of a feed medium. In addition, any one or more components of an "additive" or "supplement" can be present in the basal medium from the beginning of the cell culture.

The terms "culture", "cell culture" and "eukaryotic cell culture" as used herein refer to a eukaryotic cell population, either surface-attached or in suspension that is maintained or grown in a medium (see definition of "medium" below) under conditions suitable to survival and/or growth of the cell population. As will be clear to those of ordinary skill in the art, these terms as used herein can refer to the combination comprising the mammalian cell population and the medium in which the population is suspended.

The terms "media", "medium", "cell culture medium", "culture medium", "tissue culture medium", "tissue culture media", and "growth medium" as used herein refer to a solution containing nutrients which nourish growing cultured eukaryotic cells. Typically, these solutions provide essential and non-essential amino acids, vitamins, energy sources, lipids, and trace elements required by the cell for minimal growth and/or survival. The solution can also contain components that enhance growth and/or survival above the minimal rate, including hormones and growth factors. The solution is formulated to a pH and salt concentration optimal for cell survival and proliferation. The medium can also be a "defined medium" or "chemically defined medium"—a serum-free medium that contains no proteins, hydrolysates or components of unknown composition. Defined media are free of animal-derived components and all components have a known chemical structure. One of skill in the art understands a defined medium can comprise recombinant glycoproteins or proteins, for example, but not limited to, hormones, cytokines, interleukins and other signaling molecules.

The cell culture medium is generally "serum free" when the medium is essentially free of serum, or fractions thereof, from any mammalian source (e.g. fetal bovine serum (FBS)). By "essentially free" is meant that the cell culture medium comprises between about 0-5% serum, preferably between about 0-1% serum, and most preferably between about 0-0.1% serum. Advantageously, serum-free "defined" medium can be used, wherein the identity and concentration of each of the components in the medium is known (i.e., an undefined component such as bovine pituitary extract (BPE) is not present in the culture medium).

The term "cell viability" as used herein refers to the ability of cells in culture to survive under a given set of culture conditions or experimental variations. The term as used herein also refers to that portion of cells which are alive at a particular time in relation to the total number of cells, living and dead, in the culture at that time.

The term "cell density" as used herein refers to that number of cells present in a given volume of medium.

The term "batch culture" as used herein refers to a method of culturing cells in which all the components that will ultimately be used in culturing the cells, including the medium (see definition of "medium" below) as well as the cells themselves, are provided at the beginning of the culturing process. A batch culture is typically stopped at some point and the cells and/or components in the medium are harvested and optionally purified.

The term "fed-batch culture" as used herein refers to a method of culturing cells in which additional components are provided to the culture at some time subsequent to the beginning of the culture process. A fed-batch culture can be started using a basal medium. The culture medium with which additional components are provided to the culture at some time subsequent to the beginning of the culture process is a feed medium. A fed-batch culture is typically stopped at some point and the cells and/or components in the medium are harvested and optionally purified.

The term "perfusion culture" as used herein refers to a method of culturing cells in which additional components are provided continuously or semi-continuously to the culture subsequent to the beginning of the culture process. The provided components typically comprise nutritional supplements for the cells which have been depleted during the culturing process. A portion of the cells and/or components in the medium are typically harvested on a continuous or semi-continuous basis and are optionally purified.

The term "bioreactor" as used herein refers to any vessel used for the growth of a mammalian cell culture. The bioreactor can be of any size so long as it is useful for the culturing of mammalian cells. Typically, the bioreactor will be at least 1 liter and can be 10, 50, 100, 250, 500, 1000, 2000, 2500, 3000, 5000, 8000, 10,000, 12,0000, 15,000, 20,000, 30,000 liters or more, or any volume in between. For example, a bioreactor will be 10 to 5,000 liters, 10 to 10,000 liters, 10 to 15,000 liters, 10 to 20,000 liters, 10 to 30,000 liters, 50 to 5,000 liters, 50 to 10,000 liters, 50 to 15,000 liters, 50 to 20,000 liters, 50 to 30,000 liters, 1,000 to 5,000 liters, or 1,000 to 3,000 liters. A bioreactor can be a stirred-tank bioreactor or a shake flask. The internal conditions of the bioreactor, for example, but not limited to pH and temperature, are typically controlled during the culturing period. The bioreactor can be composed of any material that is suitable for holding mammalian cell cultures suspended in media under the culture conditions of the present invention, including glass, plastic or metal. The term "production bioreactor" as used herein refers to the final bioreactor used in the production of the glycoprotein or protein of interest. The volume of the large-scale cell culture production bioreactor is typically at least 500 liters and can be 1000, 2000, 2500, 5000, 8000, 10,000, 12,0000, 15,000 liters or more, or any volume in between. For example, the large scale cell culture reactor will be between about 500 liters and about 20,000 liters, about 500 liters and about 10,000 liters, about 500 liters and about 5,000 liters, about 1,000 liters and about 30,000 liters, about 2,000 liters and about 30,000 liters, about 3,000 liters and about 30,000 liters, about 5,000 liters and about 30,000 liters, or about 10,000 liters and about 30,000 liters, or a large scale cell culture reactor will be at least about 500 liters, at least about 1,000 liters, at least about 2,000 liters, at least about 3,000 liters, at least about 5,000 liters, at least about 10,000 liters, at least about 15,000 liters, or at least about 20,000 liters. One of ordinary skill in the art will be aware of and will be able to choose suitable bioreactors for use in practicing the present invention.

The term "stirred-tank bioreactor" as used herein refers to any vessel used for the growth of a mammalian cell culture that has an impeller.

The term "shake flask" as used herein refers to any vessel used for the growth of a mammalian cell culture that does not have an impeller.

The term "seeding" as used herein refers to the process of providing a cell culture to a bioreactor or another vessel. In one embodiment, the cells have been propagated previously in another bioreactor or vessel. In another embodiment, the cells have been frozen and thawed immediately prior to providing them to the bioreactor or vessel. The term refers to any number of cells, including a single cell.

"Growth phase" of the cell culture refers to the period of exponential cell growth (the log phase) where cells are generally rapidly dividing. During this phase, cells are cultured for a period of time, usually between 1-4 days, and under such conditions that cell growth is maximized. The determination of the growth cycle for the host cell can be determined for the particular host cell envisioned without undue experimentation. "Period of time and under such conditions that cell growth is maximized" and the like, refer to those culture conditions that, for a particular cell line, are determined to be optimal for cell growth and division. During the growth phase, cells are cultured in nutrient medium containing the necessary additives generally at about 25°–40° C., in a humidified, controlled atmosphere, such that optimal growth is achieved for the particular cell line. Cells are maintained in the growth phase for a period of about between one and seven days, e.g., between two to six days, e.g., six days. The length of the growth phase for the particular cells can be determined without undue experimentation. For example, the length of the growth phase will be the period of time sufficient to allow the particular cells to reproduce to a viable cell density within a range of about 20%-80% of the maximal possible viable cell density if the culture was maintained under the growth conditions.

"Production phase" or "protein production phase" of the cell culture refers to the period of time during which cell growth has plateaued. During the production phase, logarithmic cell growth has ended and protein production is primary. During this period of time the medium is generally supplemented to support continued protein production and to achieve the desired glycoprotein product. The production phase is typically between about three and about ten days, e.g., between about five and about eight days, e.g., six days.

The term "hybridoma" as used herein refers to a cell created by fusion of an immortalized cell derived from an immunologic source and an antibody-producing cell. The resulting hybridoma is an immortalized cell that produces antibodies. The individual cells used to create the hybridoma can be from any mammalian source, including, but not limited to, rat, pig, rabbit, sheep, pig, goat, and human. The term also encompasses trioma cell lines, which result when progeny of heterohybrid myeloma fusions, which are the product of a fusion between human cells and a murine myeloma cell line, are subsequently fused with a plasma cell. Furthermore, the term is meant to include any immortalized hybrid cell line that produces antibodies such as, for example, quadromas (See, e.g., Milstein et al., *Nature*, 537:3053 (1983)).

The term "osmolality" is a measure of the osmotic pressure of dissolved solute particles in an aqueous solution. The solute particles include both ions and non-ionized molecules. Osmolality is expressed as the concentration of osmotically active particles (i.e., osmoles) dissolved in 1 kg of water (1 mOsm/kg $H_2O$ at 38° C. is equivalent to an osmotic pressure of 19 mm Hg). "Osmolarity" refers to the number of solute particles dissolved in 1 liter of solution. Solutes which can be added to the culture medium so as to increase the osmolality thereof include proteins, peptides, amino acids, non-metabolized polymers, vitamins, ions, salts, sugars, metabolites, organic acids, lipids, etc. In the preferred embodiment, the concentration of amino acids and NaCl in the culture medium is increased in order to achieve the desired osmolality ranges set forth herein. When used herein, the abbreviation "mOsm" means "milliosmoles/kg $H_2O$".

The term "titer" as used herein refers to the total amount of recombinantly expressed glycoprotein or protein produced by a cell culture divided by a given amount of medium volume. Titer is typically expressed in units of milligrams of glycoprotein or protein per milliliter of medium or in units of grams of glycoprotein or protein per liter of medium.

The terms "Protein A" and "ProA" are used interchangeably herein and encompasses Protein A recovered from a native source thereof, Protein A produced synthetically (e.g. by peptide synthesis or by recombinant techniques), and variants thereof which retain the ability to bind proteins which have a CH2/CH3 region, such as an Fc region. Protein A can be purchased commercially from Repligen, Pharmacia and Fermatech. Protein A is generally immobilized on a solid phase support material. The term "ProA" also refers to an affinity chromatography resin or column containing chromatographic solid support matrix to which is covalently attached Protein A.

The term "chromatography" refers to the process by which a solute of interest in a mixture is separated from other solutes in a mixture as a result of differences in rates at which the individual solutes of the mixture migrate through a stationary medium under the influence of a moving phase, or in bind and elute processes.

The term "affinity chromatography" and "protein affinity chromatography" are used interchangeably herein and refer to a protein separation technique in which a protein of interest or antibody of interest is reversibly and specifically bound to a biospecific ligand. Preferably, the biospecific ligand is covalently attached to a chromatographic solid phase material and is accessible to the protein of interest in solution as the solution contacts the chromatographic solid phase material. The protein of interest (e.g., antibody, enzyme, or receptor protein) retains its specific binding affinity for the biospecific ligand (antigen, substrate, cofactor, or hormone, for example) during the chromatographic steps, while other solutes and/or proteins in the mixture do not bind appreciably or specifically to the ligand. Binding of the protein of interest to the immobilized ligand allows contaminating proteins or protein impurities to be passed through the chromatographic medium while the protein of interest remains specifically bound to the immobilized ligand on the solid phase material. The specifically bound protein of interest is then removed in active form from the immobilized ligand with low pH, high pH, high salt, competing ligand, and the like, and passed through the chromatographic column with the elution buffer, free of the contaminating proteins or protein impurities that were earlier allowed to pass through the column. Any component can be used as a ligand for purifying its respective specific binding protein, e.g. antibody.

The terms "non-affinity chromatography" and "non-affinity purification" refer to a purification process in which affinity chromatography is not utilized. Non-affinity chromatography includes chromatographic techniques that rely on non-specific interactions between a molecule of interest (such as a protein, e.g. antibody) and a solid phase matrix.

A "cation exchange resin" refers to a solid phase which is negatively charged, and which thus has free cations for exchange with cations in an aqueous solution passed over or through the solid phase. A negatively charged ligand attached to the solid phase to form the cation exchange resin may, e.g., be a carboxylate or sulfonate. Commercially available cation exchange resins include carboxy-methyl-cellulose, sulphopropyl (SP) immobilized on agarose (e.g. SP-SEPHAROSE FAST FLOW™ or SP-SEPHAROSE HIGH PERFORMANCE™, from Pharmacia) and sulphonyl immobilized on agarose (e.g. S-SEPHAROSE FAST FLOW™ from Pharmacia). A "mixed mode ion exchange resin" refers to a solid phase which is covalently modified with cationic, anionic, and hydrophobic moieties. A commercially available mixed mode ion exchange resin is BAKERBOND ABX™ (J.T. Baker, Phillipsburg, N.J.) containing weak cation exchange groups, a low concentration of anion exchange groups, and hydrophobic ligands attached to a silica gel solid phase support matrix.

The term "anion exchange resin" is used herein to refer to a solid phase which is positively charged, e.g. having one or more positively charged ligands, such as quaternary amino groups, attached thereto. Commercially available anion exchange resins include DEAE cellulose, QAE SEPHADEX™ and FAST Q SEPHAROSE™ (Pharmacia).

A "buffer" is a solution that resists changes in pH by the action of its acid-base conjugate components. Various buffers which can be employed depending, for example, on the desired pH of the buffer are described in Buffers. A Guide for the Preparation and Use of Buffers in Biological Systems, Gueffroy, D., ed. Calbiochem Corporation (1975). In one embodiment, the buffer has a pH in the range from about 2 to about 9, alternatively from about 3 to about 8, alternatively from about 4 to about 7 alternatively from about 5 to about 7. Non-limiting examples of buffers that will control the pH in this range include IVIES, MOPS, MOPSO, Tris, HEPES, phosphate, acetate, citrate, succinate, and ammonium buffers, as well as combinations of these.

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., cellular viability). The difference between said two values is, for example, less than about 50%, less than about 40%, less than about 30%, less than about 20%, and/or less than about 10% as a function of the reference/comparator value.

The phrase "substantially reduced," or "substantially different," as used herein with regard to amounts or numerical values (and not as reference to the chemical process of reduction), denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., cellular viability). The difference between said two values is, for example, greater than about 10%, greater than about 20%, greater than about 30%, greater than about 40%, and/or greater than about 50% as a function of the value for the reference/comparator molecule.

II. Supplementation of Cell Culture Medium to Alter Glycosylation Patterns

Provided herein are methods to culture eukaryotic cells engineered to express a recombinant glycoprotein of interest. Specifically this disclosure provides methods for altering the glycosylation patterns of a recombinant glycoprotein of interest by supplementing a tissue culture medium in which the cells are growing and/or producing the recombinant glycoprotein of interest with an additive, or culturing eukaryotic cells engineered to express a glycoprotein of interest in a tissue culture medium which has been supplemented with such an additive. In certain embodiments, glycoproteins produced by the methods provided are recovered. The methods are based on the recognition that growth of cells expressing a recombinant glycoprotein of interest in cell culture medium supplemented with an additive comprising one or more of mycophenolic acid, mycophenolic acid acyl glucuronide, insulin, copper (II) sulfate, hypoxanthine, thymidine, guanine, glucosamine (GlcN), galactose or mixtures thereof can result in alterations to eukaryotic cell glycosylation patterns, such as the level of afucosylation, galactosylation, N-glycan charge, N-glycolylneuraminic acid (NGNA), and FcγRIIIa binding. In certain embodiments, the alteration of the glycosylation pattern of the recombinant glycoprotein of interest comprises one or more of a reduced level of afucosylation, a reduced level of galactosylation, a reduced level of galactose-alpha-1,3-galactose (α-gal), a reduced level of N-glycolylneuraminic acid (NGNA), reduced FcγRIIIa binding, reduced antibody-dependent cell-mediated cytotoxicity, or an increased N-glycan charge. In certain embodiments, the alteration of the glycosylation pattern of the recombinant glycoprotein of interest comprises a reduced level of afucosylation. In certain embodiments, the alteration of the glycosylation pattern of the recombinant glycoprotein of interest comprises a increased level of afucosylation.

As the additives described herein have differential effects on both glycosylation and culture conditions, addition of a given additive can be used to control and/or manipulate glycosylation patterns while minimizing one or more undesirable side effects, e.g., side effects affecting cellular productivity. For example, in certain embodiments a desirable glycosylation pattern is achieved (e.g., a reduced percentage of afucosylated N-glycans) without substantially increasing the levels of α-gal, which in some instances can be an undesirable side effect. In other embodiments, desirable glycosylation patterns are achieved without substantially reducing sialic acid levels, which can be an undesirable side effect. The desirability of each additive or additive combination depends on the application. If a product quality attribute is prioritized over another product quality attribute affected by the side effect of an additive or additive combination, then providing the additive or additive combination would still be desirable.

For example, as discussed in more detail below, if reducing afucosylation is a priority and cell titer is less important, then an additive comprising copper (II) sulfate plus hypoxanthine can be desirable because it can generate a dramatic effect on afucosylation. However, if titer is of greatest importance, then a more desirable solution becomes an additive comprising copper (II) sulfate without hypoxanthine, because some reduction in afucosylation is achieved without substantially affecting cell titer. Further, if increasing afucosylation is of a greater importance and cell viability, viable cell density, and titer are of less importance, then an additive comprising mycophenolic acid or mycophenolic acid acyl glucuronide can be desirable. However, if cell viability and viable cell density and titer are also important, then an additive comprising mycophenolic acid and insulin can be desirable. In other words, the various possible additive components can be used as levers to achieve the most desirable balance between approaching a particular glycosylation pattern and minimizing side effects.

The present invention is also applicable to altering, manipulating, or controlling the glycosylation pattern of a recombinant glycoprotein of interest to match, substantially match, approach, or more closely resemble the glycosylation pattern of the same glycoprotein, but produced in a different cell culture system. Recombinant glycoproteins of interest can be produced according to the invention using various different cell culture systems, e.g., a batch culture, fed-batch culture a perfusion culture, a shake flask, and/or a bioreactor. In one embodiment, cells expressing a recombinant glycoprotein of interest are cultured in basal medium to which the additive is introduced as a bolus, or two or more boli, from a stock solution. In another embodiment, the additive is introduced as a component of a feed medium. In certain embodiments the cell culture comprises a growth phase and a protein production phase, and the additive is introduced into the culture medium before, or at the same time as, or at some point after the initiation of the protein production phase.

In one embodiment, a medium described herein is a serum-free medium, animal protein-free medium or a chemically-defined medium. In a specific embodiment, a medium described herein is a chemically-defined medium.

In certain embodiments, the additive comprises glucosamine (GlcN). In certain related embodiments the additive comprises GlcN plus galactose. An additive comprising GlcN or GlcN plus galactose can be used in a culture medium, for example, to reduce the level of afucosylation (e.g., maintain sufficient levels of fucosylated N-glycans), to reduce the levels α-gal, or to reduce the levels of NGNA of a recombinant glycoprotein of interest. In certain embodiments, the use of an additive comprising GlcN or GlcN plus galactose must be balanced with possible side effects, e.g., a slight reduction in cell density and viability, a reduced level of total sialic acid, or the appearance of unknown sialylated species.

In certain embodiments the additive comprises GlcN, which can be added to the culture medium in one bolus or two or more boli from a stock solution to achieve a GlcN concentration in the culture medium of between about 1 mM and about 100 mM. For example sufficient GlcN is added to achieve a GlcN concentration in the culture medium of between about 1 mM and about 90 mM, about 1 mM and about 80 mM, about 1 mM and about 70 mM, about 1 mM and about 60 mM, about 5 mM and about 50 mM, about 5 mM and about 40 mM, about 5 mM and about 30 mM, about 5 mM and about 20 mM, or about 5 mM and about 10 mM. In certain embodiments GlcN is added to achieve a GlcN concentration in the culture medium of about 10 mM, added as a single 10 mM bolus, or about 20 mM added as two 10 mM boli, either on the same day or on separate days. In certain embodiments the additive comprises GlcN, e.g., at the concentrations listed above, and further comprises galactose, which can be added as a component of a feed medium, to achieve a galactose concentration in the culture medium of between about 1 g/L to about 50 g/L, for example, between about 1 g/L and about 40 g/L, about 1 g/L and about 30 g/L, about 1 g/L and about 20 g/L, about 1 g/L and about 10 g/L, or about 2 g/L and about 6 g/L. In certain embodiments galactose is added to achieve a final concentration in the cell culture medium of about 2 g/L, about 3 g/L, about 4 g/L, about 5 g/L, or about 6 g/L. In certain embodiments the additive comprises GlcN, added to achieve a final concentration of about 10 mM or about 20 mM and galactose, added to achieve a final concentration of about 2 g/L, about 4 g/L, or about 6 g/L.

In certain embodiments, the additive comprises mycophenolic acid (MPA). Mycophenolic acid is known to inhibit the enzyme inosine monophosphate dehydrogenase (IMPDH) that is involved in the synthesis of guanine nucleotides (GMP) (Huang et al., Leukemia Research 32:131-141 (2008)) and to cause alterations in the formation of endothelial or surface glycoproteins (Bertalanffy et al., Clin. Chem. Lab. Med., 37(3):259-264 (1999)). The inventors have found that MPA increases the level of afucosylation of a recombinant protein produced in cell culture.

In certain related embodiments, the additive comprises MPA plus insulin, or MPA plus galactose, or MPA plus insulin and galatose. An additive comprising MPA or MPA plus galactose can be used in a culture medium, for example, to increase the level of afucosylation. In certain embodiments, the use of an additive comprising MPA or MPA plus galactose must be balanced with possible side effects, e.g., a reduction in cell density and viability, a reduced titer, or a shift in the glycan ratios.

As the supplementation of cell culture medium with mycophenolic acid has differential effects on both glycosylation and culture conditions, mycophenolic acid can be used to control and/or manipulate glycosylation patterns. In certain embodiments, the mycophenolic acid is used as a supplement in the cell culture medium to increase afucosylation level of the recombinant protein.

In certain embodiments the additive comprises MPA, which can be added to the culture medium in one bolus or two or more boli from a stock solution to achieve a MPA concentration in the culture medium of between about 1 μM and about 50 μM. For example sufficient MPA is added to achieve a MPA concentration in the culture medium of between about 1 μM and about 45 μM, about 1 μM and about 40 μM, about 1 μM and about 30 μM, about 1 μM and about 25 μM, about 5 μM and about 40 μM, about 5 and about 35 μM, about 5 μM and about 30 μM, about 5 μM and about 25 μM, or about 5 and about 20 μM. In certain embodiments MPA is added to achieve a MPA concentration in the culture medium of about 1 μM, about 2.5 μM, about 5 μM, about 7.5 μM, about 10 μM, about 15 μM, about 20 μM, about 25 μM, about 30 μM, about 35 μM, about 40 μM, about 45 μM, about 48 μM, or about 50 μM. In certain embodiments, MPA is added as a single bolus or as two or more boli, either on the same day or on separate days. In certain embodiments the additive comprises MPA, e.g., at the concentrations listed above, and further comprises galactose, which can be added as a component of a feed medium, to achieve a galactose concentration in the culture medium of between about 1 g/L to about 50 g/L, for example, between about 1 g/L and about 40 g/L, about 1 g/L and about 30 g/L, about 1 g/L and about 20 g/L, about 1 g/L and about 10 g/L, or about 1 g/L and about 5 g/L, or about or about 2 g/L and about 50 g/L or 2 g/L and about 40 g/L, or about 2 g/L and about 30 g/L, or about 2 g/L and about 20 g/L, about 2 g/L and about 10 g/L, or 5 g/L and about 50 g/L, or about 5 g/L and about 40 g/L, or about 5 g/L and about 30 g/L, or about 5 g/L and about 20 g/L, or about 5 g/L and about 10 g/L. In certain embodiments galactose is added to achieve a final concentration in the cell culture medium of about 2 g/L, about 3 g/L, about 4 g/L, about 5 g/L, or about 6 g/L, or about 10 g/L, or about 15 g/L, or about 20 g/L, or about 25 g/L, or about 30 g/L, or about 35 g/L, or about 40 g/L, or about 45 g/L, or about 50 g/L.

In certain embodiments, the additive comprises mycophenolic acid acyl glucuronide (acMPAG). Mycophenolic acid acyl glucuronide is a glucuronidation metabolite of mycophenolic acid. The inventors have found that acMPAG increases the level of afucosylation of a recombinant protein produced in cell culture.

In certain related embodiments, the additive comprises acMPAG plus insulin, or acMPAG plus galactose, or acMPAG plus insulin and galatose. An additive comprising acMPAG or acMPAG plus galactose can be used in a culture medium, for example, to increase the level of afucosylation. In certain embodiments, the use of an additive comprising acMPAG or acMPAG plus galactose must be balanced with possible side effects, e.g., a reduction in cell density and viability, a reduced titer, or a shift in the glycan ratios.

As the supplementation of cell culture medium with mycophenolic acid acyl glucuronide has differential effects on both glycosylation and culture conditions, mycophenolic acid acyl glucuronide can be used to control and/or manipulate glycosylation patterns. In certain embodiments, the mycophenolic acid acyl glucuronide is used as a supplement in the cell culture medium to increase afucosylation level of the recombinant protein.

In certain embodiments the additive comprises acMPAG, which can be added to the culture medium in one bolus or two or more boli from a stock solution to achieve acMPAG concentration in the culture medium of between about 1 μM and about 50 μM. For example sufficient acMPAG is added to achieve acMPAG concentration in the culture medium of between about 1 μM and about 45 μM, about 1 μM and about 40 μM, about 1 μM and about 30 μM, about 1 μM and about 25 μM, about 5 μM and about 40 μM, about 5 μM and about 35 μM, about 5 μM and about 30 μM, about 5 μM and about 25 μM, or about 5 μM and about 20 μM. In certain embodiments acMPAG is added to achieve acMPAG concentration in the culture medium of about 1 μM, about 2.5 μM, about 5 μM, about 7.5 μM, about 10 μM, about 15 μM, about 20 μM, about 25 μM, about 30 μM, about 35 μM, about 40 μM, about 45 μM, about 48 μM, or about 50 μM. In certain embodiments, acMPAG is added as a single bolus or as two or more boli, either on the same day or on separate days. In certain embodiments the additive comprises acMPAG, e.g., at the concentrations listed above, and further comprises galactose, which can be added as a component of a feed medium, to achieve a galactose concentration in the culture medium of between about 1 g/L to about 50 g/L, for example, between about 1 g/L and about 40 g/L, about 1 g/L and about 30 g/L, about 1 g/L and about 20 g/L, about 1 g/L and about 10 g/L, or about 1 g/L and about 5 g/L, or about or about 2 g/L and about 50 g/L or 2 g/L and about 40 g/L, or about 2 g/L and about 30 g/L, or about 2 g/L and about 20 g/L, about 2 g/L and about 10 g/L, or 5 g/L and about 50 g/L, or about 5 g/L and about 40 g/L, or about 5 g/L and about 30 g/L, or about 5 g/L and about 20 g/L, or about 5 g/L and about 10 g/L. In certain embodiments galactose is added to achieve a final concentration in the cell culture medium of about 2 g/L, about 3 g/L, about 4 g/L, about 5 g/L, or about 6 g/L, or about 10 g/L, or about 15 g/L, or about 20 g/L, or about 25 g/L, or about 30 g/L, or about 35 g/L, or about 40 g/L, or about 45 g/L, or about 50 g/L.

In certain embodiments, the additive comprises insulin. Insulin is known to stimulate the transport and phosphorylation of pyrimidine ribonucleotides in isolated bone cells (Peck et al, J. Biol. Chem., 245(10):2722-2729 (1970)). The inventors have found that insulin increases afucosylation level of a recombinant glycoprotein produced in cell culture.

In certain related embodiments the additive comprises insulin plus mycophenolic acid (MPA) and/or mycophenolic acid acyl glucuronide (acMPAG). An additive comprising insulin or insulin plus MPA and/or acMPAG can be used in a culture medium, for example, to increase the level of afucosylation (e.g., maintain sufficient levels of fucosylated N-glycans). In certain embodiments, the use of an additive comprising insulin or insulin plus MPA and/or acMPAG must be balanced with possible side effects, e.g., a slight reduction in cell density and viability.

As the supplementation of cell culture medium with insulin has differential effects on both glycosylation and culture conditions, insulin can be used to control and/or manipulate glycosylation patterns without having any undesirable side effects, e.g., side effects affecting cellular productivity. In certain embodiments, the insulin is used as a supplement in the cell culture medium to increase afucosylation level of the recombinant protein.

In certain embodiments the additive comprises insulin, which can be added to the culture medium in one bolus or two or more boli from a stock solution to achieve an insulin concentration in the culture medium of between about 1 mg/L and about 50 mg/L. For example sufficient insulin is added to achieve an insulin concentration in the culture medium of between about 1 mg/L and about 40 mg/L, or 1 mg/L and about 30 mg/L, or about 1 mg/L and about 25 mg/L, 1 mg/L and about 22.5 mg/L, or about 1 mg/L and about 20 mg/L, or 1 mg/L and about 15 mg/L, or about 1 mg/L and about 15 mg/L, or about 1 mg/L and about 10 mg/L, or about 5 mg/L and about 50 mg/L, or about 5 mg/L and about 40 mg/L, or about 5 mg/L and about 30 mg/L, or about 5 mg/L and about 25 mg/L, or about 5 mg/L and about 20 mg/L, or about 5 mg/L and about 15 mg/L, or about 5 mg/L and about 10 mg/L, or about 10 mg/L and about 50 mg/L, or about 10 mg/L and about 40 mg/L, or about 10 mg/L and about 30 mg/L, or about 10 mg/L and about 25 mg/L, or about 10 mg/L and about 20 mg/L, or about 10 mg/L and about 15 mg/L, or about 15 mg/L and about 25 mg/L, or about 15 mg/L and about 20 mg/L, or about 17 mg/L and about 25 mg/L, or about 17 mg/L and about 20 mg/L, or about 17 mg/L and about 24 mg/L. In certain embodiments insulin is added to achieve an insulin concentration in the culture medium of about 10.6 mg/L, about 13 mg/L, about 17.2 mg/L, or about 24.4 mg/L added as a single bolus, or as two or more boli, either on the same day or on separate days. In certain embodiments the additive comprises insulin, e.g., at the concentrations listed above, and further comprises mycophenolic acid (MPA) and/or mycophenolic acid acyl glucuronide (acMPAG), which can be added as a component of a feed medium, to achieve a MPA and/or acMPAG concentration in the culture medium of between about 1 μM and about 50 μM, for example, between about 1 μM and about 45 μM, about 1 μM and about 40 μM, about 1 μM and about 30 μM, about 1 μM and about 25 μM, about 5 μM and about 40 μM, about 5 μM and about 35 μM, about 5 μM and about 30 μM, about 5 μM and about 25 μM, or about 5 μM and about 20 μM. In certain embodiments MPA and/or acMPAG is added to achieve a final concentration in the cell culture medium of about 1 μM, about 2.5 μM, about 5 μM, about 7.5 μM, about 10 μM, about 15 μM, about 20 μM, about 25 μM, about 30 μM, about 35 μM, about 40 μM, about 45 μM, about 48 μM, or about 50 μM. In certain embodiments the additive comprises insulin, added to achieve a final concentration of about 10.6 mg/L, about 13 mg/L, about 17.2 mg/L, or about 24.4 mg/L and galactose, added to achieve a final concentration of about 2 g/L, about 4 g/L, or about 6 g/L, or about 10 g/L.

In certain embodiments, the additive comprises copper (II) sulfate ($CuSO_4$). In certain embodiments the additive comprises $CuSO_4$ and further comprises GlcN and/or galactose. In certain embodiments the additive comprises $CuSO_4$ and further comprises hypoxanthine. In certain embodiments the additive comprises $CuSO_4$ and hypoxanthine, and further comprises thymidine. An additive comprising $CuSO_4$, $CuSO_4$, GlcN, and galactose, $CuSO_4$ and hypoxanthine, or $CuSO_4$, hypoxanthine, and thymidine, can be used in a culture medium, for example, to reduce the level of afucosylation (e.g., maintain sufficient levels of fucosylated N-glycans), to reduce the level of galactosylation, and/or to increase the level of charged N-glycans of a recombinant glycoprotein of interest. In certain embodiments, the use of an additive comprising $CuSO_4$, $CuSO_4$, GlcN, and galactose, $CuSO_4$ and hypoxanthine, or $CuSO_4$, hypoxanthine, and thymidine must be balanced with possible side effects, e.g., a slight reduction in cell density and viability, or a reduced level of total sialic acid.

In certain embodiments the additive comprises $CuSO_4$, which can be added to the culture medium in one bolus or two or more boli from a stock solution to, or be added as a component of a feed medium achieve a $CuSO_4$ concentration in the culture medium of between about 0.05 mM and about 10 mM $CuSO_4$. In certain embodiments the additive comprises $CuSO_4$, which can be added to the culture medium in one bolus or two or more boli from a stock solution to, or be added as a component of a feed medium achieve a $CuSO_4$ concentration in the culture medium between about 0.1 mM and about 10 mM, about 0.2 mM and about 5 mM, about 0.2 mM and about 4 mM, about 0.2 mM and about 3 mM, about 0.2 mM and about 2 mM, about 0.2 mM and about 1 mM, or about 0.2 mM and about 0.5 mM.

In certain embodiments the additive comprises $CuSO_4$, e.g., at the concentrations listed above, and further comprises GlcN and galactose, which can be added as one bolus or two or more boli of a stock solution or as a component of a feed medium to achieve GlcN concentrations between about 1 mM and about 100 mM, about 1 mM and about 90 mM, about 1 mM and about 80 mM, about 1 mM and about 70 mM, about 1 mM and about 60 mM, about 5 mM and about 50 mM, about 5 mM and about 40 mM, about 5 mM and about 30 mM, about 5 mM and about 20 mM, or about 5 mM and about 10 mM; and a galactose concentration of between about 1 g/L to about 50 g/L, for example, between about 1 g/L and about 40 g/L, about 1 g/L and about 30 g/L, about 1 g/L and about 20 g/L, about 1 g/L and about 10 g/L, or about 2 g/L and about 6 g/L. In certain embodiments galactose is added to achieve a final concentration in the cell culture medium of about 2 g/L, about 3 g/L, about 4 g/L, about 5 g/L, or about 6 g/L. In certain embodiments the additive comprises GlcN, added to achieve a final concentration of about 10 mM or about 20 mM and galactose, added to achieve a final concentration of about 2 g/L, about 4 g/L, or about 6 g/L. In certain embodiments the additive comprises $CuSO_4$, e.g., at about 0.2 mM or about 0.5 mM, and further comprises GlcN and galactose to achieve a GlcN concentration in the culture medium of about 10 mM or about 20 mM and a galactose concentration of about 2 g/L, about 4 g/L, or about 6 g/L.

In certain embodiments the additive comprises $CuSO_4$, e.g., at the concentrations listed above, and further comprises hypoxanthine, which can be added either as a single bolus or two or more boli from a stock solution or can be added as a component of a feed medium, to achieve a hypoxanthine concentration of between about 0.1 mM and about 10 mM, about 0.3 mM and about 5 mM, about 0.3 mM and about 4 mM, about 0.3 mM and about 3 mM, about 0.3 mM and about 2 mM, about 0.3 mM and to about 1 mM, about 0.5 mM and about 0.9 mM, about 0.5 mM and about 0.8 mM, or about 0.5 mM and about 0.7 mM. In certain embodiments, the additive comprises $CuSO_4$ and hypoxanthine to achieve a final concentration in the cell culture medium of about 0.23 mM $CuSO_4$ and about 0.7 mM hypoxanthine.

In certain embodiments the additive comprises $CuSO_4$ and hypoxanthine, e.g., at the concentrations listed above, and further comprises thymidine, which can be added as a component of a feed medium or as a single bolus or two or more boli from a stock solution, to achieve a final concentration in the cell culture medium of between about 0.005 mM and about 5 mM, about 0.005 mM and about 1 mM about 0.005 mM and about 0.5 mM, about 0.01 mM and about 0.1 mM, about 0.01 mM and about 0.05 mM, about 0.01 mM and about 0.2 mM, or about 0.05 mM and about 0.2 mM. In certain embodiments, the additive comprises $CuSO_4$, hypoxanthine, and thymidine to achieve final concentrations in the cell culture medium of about 0.3 mM $CuSO_4$, about 0.3 mM hypoxanthine, and about 0.05 mM thymidine, or about 0.3 mM $CuSO_4$, about 1 mM hypoxanthine, and about 0.16 mM thymidine.

In certain embodiments, the additive comprises hypoxanthine, which can be added either as a single bolus or two or more boli from a stock solution or can be added as a component of a feed medium, to achieve a hypoxanthine concentration in the cell culture medium of between about 0.1 mM and about 10 mM, about 0.3 mM and about 5 mM, about 0.3 mM and about 4 mM, about 0.3 mM and about 3 mM, about 0.3 mM and about 2 mM, about 0.3 mM and to about 1 mM, about 0.5 mM and about 0.9 mM, about 0.5 mM and about 0.8 mM, or about 0.5 mM and about 0.7 mM. In certain embodiments the additive comprises hypoxanthine to achieve a hypoxanthine concentration in the cell culture medium of about 1 mM. In certain embodiments the additive comprises guanine, which can be added either as a single bolus or two or more boli from a stock solution or can be added as a component of a feed medium, to achieve a guanine concentration in the cell culture medium of between about 0.1 mM and about 10 mM, about 0.3 mM and about 5 mM, about 0.3 mM and about 4 mM, about 0.3 mM and about 3 mM, about 0.3 mM and about 2 mM, about 0.3 mM and to about 1 mM, about 0.5 mM and about 0.9 mM, about 0.5 mM and about 0.8 mM, or about 0.5 mM and about 0.7 mM. In certain embodiments the additive comprises guanine to achieve a guanine concentration in the cell culture medium of about 0.2 mM. An additive comprising hypoxanthine or guanine can be used in a culture medium, for example, to reduce the level of afucosylation (e.g., maintain sufficient levels of fucosylated N-glycans) or to reduce the levels of FcγRIIIa binding. In certain embodiments, the use of an additive comprising hypoxanthine or guanine must be balanced with possible side effects, e.g., a slight reduction in cell density and viability.

III. Control or Modulation of Cell Culture Temperature to Alter Glycosylation Pattern Provided herein are methods to culture eukaryotic cells engineered to express a recombinant glycoprotein of interest. Specifically, this disclosure provides methods for altering the glycosylation patterns of a recombinant glycoprotein of interest by controlling or modulating (shifting) temperature of a cell culture in which the cells are growing and/or producing the recombinant glycoprotein of interest or culturing eukaryotic cells engineered to express a glycoprotein of interest in a cell culture that has a controlled or modulated (shifted) temperature.

In certain embodiments, glycoproteins produced by the methods provided are recovered. The methods are based on the recognition that growth of cells expressing a recombinant glycoprotein of interest in cell culture medium with a controlled or modulated (shifted) temperature can result in alterations to eukaryotic cell glycosylation patterns, such as the level of afucosylation, galactosylation, N-glycan charge, N-glycolylneuraminic acid (NGNA), and FcγRIIIa binding. In certain embodiments, the alteration of the glycosylation pattern of the recombinant glycoprotein of interest comprises one or more of a reduced level of afucosylation, a reduced level of galactosylation, a reduced level of galactose-alpha-1,3-galactose (α-gal), a reduced level of N-glycolylneuraminic acid (NGNA), reduced FcγRIIIa binding, reduced antibody-dependent cell-mediated cytotoxicity, or an increased N-glycan charge. In certain embodiments, the alteration of the glycosylation pattern of the recombinant glycoprotein of interest comprises an increased level of afucosylation.

As the temperature of the cell culture has differential effects on both glycosylation and culture conditions, temperature can be used to control or modulate (shift) glycosylation patterns while minimizing one or more undesirable side effects, e.g., side effects affecting cellular productivity. In certain embodiments, the control or modulation of cell culture temperature comprises a reduction in the temperature to result in an increased levels of afucosylation. In certain embodiments, the modulation of cell culture temperature comprises a reduction in the temperature to result in a decreased levels of afucosylation. In other embodiments, the control or modulation of cell culture temperature comprises an increase in the temperature to result in an increased levels of afucosylation. In certain embodiments, the modulation of cell culture temperature comprises an increase in the temperature to result in a decreased levels of afucosylation.

In certain embodiments, the disclosure provides methods for altering the glycosylation patterns of a recombinant glycoprotein of interest by supplementing a culture medium in which the cells are growing with an additive and controlling or modulating (shifting) the temperature of the cell culture. In certain embodiments, the disclosure provides methods for producing the recombinant glycoprotein of interest with an additive in a culture medium that has controlled or modulated (shifted) cell culture temperature, or culturing eukaryotic cells engineered to express a glycoprotein of interest in a tissue culture medium that has been supplemented with an additive and has a controlled or modulated (shifted) temperature. For example, in certain embodiments a desirable glycosylation pattern is achieved (e.g., a reduced percentage of afucosylated N-glycans) without substantially increasing the levels of α-gal, which in some instances can be an undesirable side effect. In other embodiments, desirable glycosylation patterns are achieved without substantially reducing sialic acid levels, which can be an undesirable side effect. The desirability of each combination depends on the application. If a product quality attribute is prioritized over the product quality attribute affected by the corresponding side effect, then providing the additive would still be desirable.

In certain embodiments, the disclosure provides methods for altering the glycosylation patterns of a recombinant glycoprotein of interest by supplementing the medium in which the cells are growing with mycophenolic acid as an additive and modifying the cell culture temperature. In certain embodiments, the disclosure provides methods for altering the glycosylation patterns of a recombinant glycoprotein of interest by supplementing the medium in which the cells are growing with mycophenolic acid acyl glucuronide as an additive and modifying the cell culture temperature. In certain embodiments, the disclosure provides methods for producing the recombinant glycoprotein of interest with mycophenolic acid as an additive in a culture medium that has controlled or manipulated cell culture temperature, or culturing eukaryotic cells engineered to express a glycoprotein of interest in a tissue culture medium that has been supplemented with mycophenolic acid as an additive and has a controlled or modulated (shifted) temperature. In certain embodiments, the disclosure provides methods for producing the recombinant glycoprotein of interest with mycophenolic acid acyl glucuronide as an additive in a culture medium that has controlled or manipulated cell culture temperature, or culturing eukaryotic cells engineered to express a glycoprotein of interest in a tissue culture medium that has been supplemented with mycophenolic acid acyl glucuronide as an additive and has a controlled or modulated (shifted) temperature.

In certain embodiments, controlling or modulating (shifting) the temperature of the cell culture plus supplementing the culture medium with an additive comprising mycophenolic acid can be desirable. In certain embodiments, controlling or modulating (shifting) the temperature of the cell culture plus supplementing the culture medium with an additive comprising mycophenolic acid acyl glucuronide can be desirable. In certain embodiments, controlling or modulating (shifting) the temperature of the cell culture plus supplementing the culture medium with an additive comprising insulin can be desirable. In other words, the various possible additive components can be used as levers to achieve the most desirable balance between approaching a particular glycosylation pattern and minimizing side effects. The present invention is also applicable to altering, manipulating, or controlling the glycosylation pattern of a recombinant glycoprotein of interest to match, substantially match, approach, or more closely resemble the glycosylation pattern of the same glycoprotein, but produced in a different cell culture system. Recombinant glycoproteins of interest can be produced according to the invention using various different cell culture systems, e.g., a batch culture, fed-batch culture a perfusion culture, a shake flask, and/or a bioreactor. In one embodiment, cells expressing a recombinant glycoprotein of interest are cultured in basal medium to which the additive is introduced as a bolus, or two or more boli, from a stock solution. In another embodiment, the additive is introduced as a component of a feed medium.

In certain embodiments the cell culture comprises a growth phase and a protein production phase, and the cell culture temperature is controlled or modulated (shifted) before, or at the same time as, or at some point after the initiation of the protein production phase. In certain embodiments, the additive is introduced into the culture medium before, or at the same time as, or at some point after the initiation of the protein production phase. In certain embodiments, the additive is introduced and the temperature is controlled or modulated (shifted) at the same time. In certain embodiments, the additive is introduced and the cell culture temperature is controlled or modulated (shifted) at different times.

In one embodiment, a medium described herein is a serum-free medium, animal protein-free medium or a chemically-defined medium. In a specific embodiment, a medium described herein is a chemically-defined medium.

In certain embodiments, the controlling or modulating (shifting) of cell culture temperature comprises decreasing the culture temperature up to 25° C. In certain embodiments, the controlling or modulating (shifting) of cell culture temperature comprises increasing the culture temperature up to 42° C. In certain embodiments, the cell culture temperature is controlled or modulated (shifted) to about 25° C., about 25.5° C., about 26° C., about 26.5° C., about 27° C., about 27.5° C., about 28° C., about 28.5° C., about 29° C., about 29.5° C., about 30° C., about 30.5° C., about 31° C., about 31.5° C., about 32° C., about 32.5° C., about 33° C., about 33.5° C., about 34° C., about 34.5° C., about 35° C., about 35.5° C., about 36° C., about 36.5° C., about 37° C., about 37.5° C., about 38° C., about 38.5° C., about 39° C., about 39.5° C., about 40° C., about 40.5° C., about 41° C., about 41.5° C., or about 42° C.

IV. Control or Modulation of Seed Density to Alter Glycosylation Pattern

Provided herein are methods to culture eukaryotic cells engineered to express a recombinant glycoprotein of interest. Specifically, this disclosure provides methods for altering the glycosylation patterns of a recombinant glycoprotein of interest by controlling or modulating seed density of a cell culture and/or producing the recombinant glycoprotein of interest or culturing eukaryotic cells engineered to express a glycoprotein of interest in a cell culture that has a controlled or modulated seed density.

In certain embodiments, glycoproteins produced by the methods provided are recovered. The methods are based on the recognition that growth of cells expressing a recombinant glycoprotein of interest in cell culture medium with a controlled or modulated seed density can result in alterations to eukaryotic cell glycosylation patterns, such as the level of afucosylation, galactosylation, N-glycan charge, N-glycolylneuraminic acid (NGNA), and FcγRIIIa binding. In certain embodiments, the alteration of the glycosylation pattern of the recombinant glycoprotein of interest comprises one or more of a reduced level of afucosylation, a reduced level of galactosylation, a reduced level of galactose-alpha-1,3-galactose (α-gal), a reduced level of N-glycolylneuraminic acid (NGNA), reduced FcγRIIIa binding, reduced antibody-dependent cell-mediated cytotoxicity, or an increased N-glycan charge. In certain embodiments, the alteration of the glycosylation pattern of the recombinant glycoprotein of interest comprises an increased level of afucosylation.

As the seed density of the cell culture has differential effects on both glycosylation and culture conditions, seed density can be used to control or modulate glycosylation patterns and one or more undesirable side effects. In certain embodiments, the control or modulation of cell culture seed density comprises a reduction in the seed density to result in an increased levels of afucosylation. In certain embodiments, the modulation of cell culture seed density comprises an increase in the seed density to result in a decreased levels of afucosylation.

In certain embodiments, the disclosure provides methods for altering the glycosylation patterns of a recombinant glycoprotein of interest by supplementing a culture medium in which the cells are growing with an additive and controlling or modulating the seed density of the cell culture. In certain embodiments, the disclosure provides methods for producing the recombinant glycoprotein of interest with an additive in a culture medium that has controlled or modulated cell culture seed density, or culturing eukaryotic cells engineered to express a glycoprotein of interest in a tissue culture medium that has been supplemented with an additive and has a controlled or modulated seed density. For example, in certain embodiments a desirable glycosylation pattern is achieved (e.g., a reduced percentage of afucosylated N-glycans) without substantially increasing the levels of α-gal, which in some instances can be an undesirable side effect. In other embodiments, desirable glycosylation patterns are achieved without substantially reducing sialic acid levels, which can be an undesirable side effect. The desirability of each combination depends on the application. If a product quality attribute is prioritized over the product quality attribute affected by the corresponding side effect, then providing the additive would still be desirable.

In certain embodiments, the disclosure provides methods for altering the glycosylation patterns of a recombinant glycoprotein of interest by supplementing the medium in which the cells are growing with mycophenolic acid and/or mycophenolic acid acyl glucuronide as an additive and modifying the cell culture seed density. In certain embodiments, the disclosure provides methods for producing the recombinant glycoprotein of interest with mycophenolic acid and/or mycophenolic acid acyl glucuronide as an additive in a culture medium that has controlled or manipulated cell culture seed density, or culturing eukaryotic cells engineered to express a glycoprotein of interest in a tissue culture medium that has been supplemented with mycophenolic acid and/or mycophenolic acid acyl glucuronide as an additive and has a controlled or modulated seed density.

In certain embodiments, the disclosure provides methods for altering the glycosylation patterns of a recombinant glycoprotein of interest by supplementing the medium in which the cells are growing with insulin as an additive and modifying the cell culture seed density. In certain embodiments, the disclosure provides methods for producing the recombinant glycoprotein of interest with insulin as an additive in a culture medium that has controlled or manipulated cell culture seed density, or culturing eukaryotic cells engineered to express a glycoprotein of interest in a tissue culture medium that has been supplemented with insulin as an additive and has a controlled or modulated seed density.

In certain embodiments, the disclosure provides methods for altering the glycosylation patterns of a recombinant glycoprotein of interest by modifying the cell culture seed density and temperature. In certain embodiments, the disclosure provides methods for producing the recombinant glycoprotein of interest in a culture medium that has controlled or manipulated cell culture seed density and temperature, or culturing eukaryotic cells engineered to express a glycoprotein of interest in a tissue culture medium that has a controlled or modulated cell culture seed density and temperature. In other words, the various possible additive components can be used as levers to achieve the most desirable balance between approaching a particular glycosylation pattern and minimizing side effects.

The present invention is also applicable to altering, manipulating, or controlling the glycosylation pattern of a recombinant glycoprotein of interest to match, substantially match, approach, or more closely resemble the glycosylation pattern of the same glycoprotein, but produced in a different cell culture system. Recombinant glycoproteins of interest can be produced according to the invention using various different cell culture systems, e.g., a batch culture, fed-batch culture a perfusion culture, a shake flask, and/or a bioreactor. In one embodiment, cells expressing a recombinant glycoprotein of interest are cultured in basal medium to which the additive is introduced as a bolus, or two or more boli, from a stock solution. In another embodiment, the additive is introduced as a component of a feed medium.

In one embodiment, a medium described herein is a serum-free medium, animal protein-free medium or a chemically-defined medium. In a specific embodiment, a medium described herein is a chemically-defined medium.

In certain embodiments, the controlling or modulating of cell culture seed density comprises having the culture seed density less than regular seed density ("low seed density"). In certain embodiments, the controlling or modulating of cell culture seed density comprises having the culture seed density to more than regular seed density ("high seed density"). For example, the cell culture seed density comprises regular seed density of 3.5-5.5e5 vc/mL for DUXB11 cell line; the cell culture seed density comprises low seed density of <3e5 vc/mL for DUXB11 cell line; and the cell culture seed density comprises high seed density of >7e5 vc/mL for DUXB11 cell line. A person of ordinary skill in the art can determine a high seed density, a low seed density and a regular seed density for other cell lines.

The present invention further provides a cell culture composition comprising a medium described herein and cells, produced by the methods provided herein.

In one embodiment, a cell culture composition produced by the provided methods can be a batch culture, fed-batch culture or a perfusion culture. In a specific embodiment, a cell culture composition of the invention is a fed batch culture.

In one embodiment, a cell culture composition produced by the provided methods comprises mammalian cells selected from the group consisting of CHO cells, HEK cells, NSO cells, PER.C6 cells, 293 cells, HeLa cells, and MDCK cells. In a specific embodiment, a cell culture composition described herein comprises CHO cells. In another specific embodiment, a cell culture composition described herein comprises HEK cells. In another specific embodiment, a cell culture composition described herein comprises hybridoma cells.

A cell culture composition produced by the provided methods can comprise cells that have been adapted to grow in serum free medium, animal protein free medium or chemically defined medium. Or it can comprise cells that have been genetically modified to increase their life-span in culture. In one embodiment, the cells have been modified to express an anti-apoptotic gene. In a specific embodiment, the cells have been modified to express the bcl-xL antiapoptotic gene. Additional anti-apoptotic genes that can be used in accordance with the present invention include, but are not limited to, E1B-9K, Aven, Mcl.

The present invention provides a method of culturing cells, comprising contacting the cells with a medium disclosed herein, supplementing the medium as described above, or culturing cells in a medium supplemented as described above.

Cell cultures can be cultured in a batch culture, fed batch culture or a perfusion culture. In one embodiment, a cell culture according to a method of the present invention is a batch culture. In another embodiment, a cell culture according to a method of the present invention is a fed batch culture. In a further embodiment, a cell culture according to a method of the present invention is a perfusion culture. In certain embodiments the cell culture is maintained in a shake flask, in certain embodiments the cell culture is maintained in a bioreactor.

In one embodiment, a cell culture according to a method of the present invention is a serum-free culture. In another embodiment, a cell culture according to a method of the present invention is a chemically defined culture. In a further embodiment, a cell culture according to a method of the present invention is an animal protein free culture.

In one embodiment, a cell culture produced by the provided methods is contacted with a medium described herein during the growth phase of the culture. In another embodiment, a cell culture is contacted with a medium described herein during the production phase of the culture.

In one embodiment, a cell culture produced by the provided methods is contacted with a feed medium described herein during the production phase of the culture. In one embodiment, the culture is supplemented with the feed medium between about 1 and about 25 times during the second time period. In another embodiment, a culture is supplemented with the feed medium between about 1 and about 20 times, between about 1 and about 15 times, or between about 1 and about 10 times during the first time period. In a further embodiment, a culture is supplemented with the feed medium at least once, at least twice, at least three times, at least four times, at least five times, at least 6 times, at least 7 times, at least 8 times, at least 9 times, at least 10 times, at least 1 times, at least 12 times, at least 13 times, at least 14 times, at least 15 times, at least 20 times, at least 25 times. In a specific embodiment, the culture is a fed batch culture. In another specific embodiment, the culture is a perfusion culture.

A culture produced by the provided methods can be contacted with a feed medium described herein at regular intervals. In one embodiment, the regular interval is about once a day, about once every two days, about once every three days, about once every 4 days, or about once every 5 days. In a specific embodiment, the culture is a fed batch culture. In another specific embodiment, the culture is a perfusion culture.

A culture produced by the provided methods can be contacted with a feed medium described herein on an as needed basis based on the metabolic status of the culture. In one embodiment, a metabolic marker of a fed batch culture is measured prior to supplementing the culture with a feed medium described herein. In one embodiment, the metabolic marker is selected from the group consisting of: lactate concentration, ammonium concentration, alanine concentration, glutamine concentration, glutamate concentration, cell specific lactate production rate to the cell specific glucose uptake rate ratio (LPR/GUR ratio), and Rhodamine 123 specific cell fluorescence. In one embodiment, an LPR/GUR value of >0.1 indicates the need to supplement the culture with a feed medium described herein. In a further specific embodiment, a lactate concentration of >3 g/L indicates the need to supplement the culture with a feed medium described herein. In another embodiment, a culture according to the present invention is supplemented with a feed medium described herein when the LPR/GUR value of the culture is >0.1 or when the lactate concentration of the culture is >3 g/L. In a specific embodiment, the culture is a fed batch culture. In another specific embodiment, the culture is a perfusion culture.

In one embodiment, a medium described herein is a feed medium for a fed batch cell culture. A skilled artisan understands that a fed batch cell culture can be contacted with a feed medium more than once. In one embodiment, a fed batch cell culture is contacted with a medium described herein only once. In another embodiment, a fed batch cell culture is contacted with a medium described herein more than once, for example, at least twice, at least three times, at least four times, at least five times, at least six times, at least seven times, or at least ten times.

In accordance with the present invention, the total volume of feed medium added to a cell culture should optimally be kept to a minimal amount. For example, the total volume of the feed medium added to the cell culture can be 1, 2, 3, 4, 5, 6, 7, 8, 9, 10, 15, 20, 25, 30, 35, 40, 45 or 50% of the volume of the cell culture prior to adding the feed medium.

Cell cultures produced by the provided methods can be grown to achieve a particular cell density, depending on the needs of the practitioner and the requirement of the cells themselves, prior to being contacted with a medium described herein. In one embodiment, the cell culture is contacted with a medium described herein at a viable cell density of 1, 5, 10, 15, 20, 25, 30, 35, 40, 45, 50, 55, 60, 65, 70, 75, 80, 85, 90, 95 or 99 percent of maximal viable cell density. In a specific embodiment, the medium is a feed medium.

Cell cultures produced by the provided methods can be allowed to grow for a defined period of time before they are contacted with a medium described herein. In one embodiment, the cell culture is contacted with a medium described herein at day 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the cell culture. In another embodiment, the cell culture is contacted with a medium described herein at week 1, 2, 3, 4, 5, 6, 7, or 8 of the cell culture. In a specific embodiment, the medium is a feed medium.

Cell cultures produced by the provided methods can be cultured in the production phase for a defined period of time. In one embodiment, the cell culture is contacted with a feed medium described herein at day 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the production phase.

A culture produced by the provided methods can be maintained in production phase for between about 1 day and about 30 days. In one embodiment, a culture is maintained in production phase for between about 1 day and about 30 days, between about 1 day and about 25 days, between about 1 day and about 20 days, about 1 day and about 15 days, about 1 day and about 14 days, about 1 day and about 13 days, about 1 day and about 12 days, about 1 day and about 11 days, about 1 day and about 10 days, about 1 day and about 9 days, about 1 day and about 8 days, about 1 day and about 7 days, about 1 day and about 6 days, about 1 day and about 5 days, about 1 day and about 4 days, about 1 day and about 3 days, about 2 days and about 25 days, about 3 days and about 25 days, about 4 days and about 25 days, about 5 days and about 25 days, about 6 days and about 25 days, about 7 days and about 25 days, about 8 days and about 25 days, about 9 days and about 25 days, about 10 days and about 25 days, about 15 days and about 25 days, about 20 days and about 25 days, about 2 days and about 30 days, about 3 days and about 30 days, about 4 days and about 30 days, about 5 days and about 30 days, about 6 days and about 30 days, about 7 days and about 30 days, about 8 days and about 30 days, about 9 days and about 30 days, about 10 days and about 30 days, about 15 days and about 30 days, about 20 days and about 30 days, or about 25 days and about 30 days. In another embodiment, a culture is maintained in production phase for at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 15 days, at least about 20 days, at least about 25 days, or at least about 30 days. In a further embodiment, a culture is maintained in production phase for about 1 day, about 2 days, about 3 days, about 4 days, about 5 days, about 6 days, about 7 days, about 8 days, about 9 days, about 10 days, about 11 days, about 12 days, about 15 days, about 20 days, about 25 days, or about 30 days.

The present invention further provides a method of producing a recombinant glycoprotein interest, comprising culturing cells engineered to express the recombinant glycoprotein of interest in a culture comprising a medium described herein; and recovering or isolating the recombinant glycoprotein of interest from the culture. In certain embodiments, the recombinant glycoprotein of interest is an enzyme, receptor, antibody, immunoadhesin, hormone, regulatory factor, antigen, coagulation factor, or binding agent. In a specific embodiment, the recombinant glycoprotein of interest is an antibody. In another embodiment, the recombinant glycoprotein of interest is an immunoadhesin. In another embodiment, the recombinant glycoprotein of interest is a coagulation factor.

In a specific embodiment, a method of producing a recombinant glycoprotein of interest according to the present invention produces a maximum glycoprotein titer of at least about 0.05 g/L, at least about 0.1 g/L, at least about 0.25 g/L, at least about 0.5 g/L, at least about 0.75 g/L, at least about 1.0 g/L, at least about 1.5 g/L, at least about 2 g/liter, at least about 2.5 g/liter, at least about 3 g/liter, at least about 3.5 g/liter, at least about 4 g/liter, at least about 4.5 g/liter, at least about 5 g/liter, at least about 6 g/liter, at least about 7 g/liter, at least about 8 g/liter, at least about 9 g/liter, or at least about 10 g/liter. In another embodiment, the method according to the present invention produces a maximum glycoprotein titer of between about 1 g/liter and about 10 g/liter, about 1.5 g/liter and about 10 g/liter, about 2 g/liter and about 10 g/liter, about 2.5 g/liter and about 10 g/liter, about 3 g/liter and about 10 g/liter, about 4 g/liter and about 10 g/liter, about 5 g/liter and about 10 g/liter, about 1 g/liter and about 5 g/liter, about 1 g/liter and about 4.5 g/liter, or about 1 g/liter and about 4 g/liter. In a specific embodiment, the glycoprotein is an antibody. In another embodiment, the glycoprotein is a blood clotting factor.

The invention further provides a conditioned cell culture medium produced by a method described herein.

In one embodiment, a conditioned cell culture medium produced according to the provided methods comprises a recombinant glycoprotein of interest. In a specific embodiment, a conditioned cell culture medium according to the invention comprises a recombinant glycoprotein of interest at a titer of at least about 2 g/liter, at least about 2.5 g/liter, at least about 3 g/liter, at least about 3.5 g/liter, at least about 4 g/liter, at least about 4.5 g/liter, at least about 5 g/liter, at least about 6 g/liter, at least about 7 g/liter, at least about 8 g/liter, at least about 9 g/liter, or at least about 10 g/liter, or a titer of between about 1 g/liter and about 10 g/liter, about 1.5 g/liter and about 10 g/liter, about 2 g/liter and about 10 g/liter, about 2.5 g/liter and about 10 g/liter, about 3 g/liter and about 10 g/liter, about 4 g/liter and about 10 g/liter, about 5 g/liter and about 10 g/liter, about 1 g/liter and about 5 g/liter, about 1 g/liter and about 4.5 g/liter, or about 1 g/liter and about 4 g/liter. In another embodiment, a conditioned cell culture medium according to the invention comprises a recombinant glycoprotein at a higher titer than the titer obtained without the use of a medium described herein. In a specific embodiment, the protein or polypeptide is an antibody.

Glycoproteins

Any glycoprotein that is expressible in a host cell can be produced in accordance with the present invention. The glycoprotein can be expressed from a gene that is endogenous to the host cell, or from a gene that is introduced into the host cell through genetic engineering. The glycoprotein can be one that occurs in nature, or can alternatively have a sequence that was engineered or selected by the hand of man. An engineered glycoprotein can be assembled from other glycoprotein segments that individually occur in nature, or can include one or more segments that are not naturally occurring.

Glycoproteins that can desirably be expressed by the methods provided herein will often be selected on the basis of an interesting biological or chemical activity. For example, the present invention can be employed to express any pharmaceutically or commercially relevant enzyme, receptor, antibody, immunoadhesin, hormone, regulatory factor, antigen, binding agent, etc.

Antibodies

Given the large number of antibodies currently in use or under investigation as pharmaceutical or other commercial agents, production of antibodies is of particular interest in accordance with the present invention. Antibodies are proteins that have the ability to specifically bind a particular antigen. Any antibody that can be expressed in a host cell can be used in accordance with the present invention. In one embodiment, the antibody to be expressed is a monoclonal antibody.

Particular antibodies can be made, for example, by preparing and expressing synthetic genes that encode the recited amino acid sequences or by mutating human germline genes to provide a gene that encodes the recited amino acid sequences. Moreover, these antibodies can be produced, e.g., using one or more of the following methods.

Numerous methods are available for obtaining antibodies, particularly human antibodies. One exemplary method includes screening protein expression libraries, e.g., phage or ribosome display libraries. Phage display is described, for example, U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; and WO 90/02809. The display of Fab's on phage is described, e.g., in U.S. Pat. Nos. 5,658,727; 5,667,988; and 5,885,793.

In addition to the use of display libraries, other methods can be used to obtain an antibody. For example, a protein or a peptide thereof can be used as an antigen in a non-human animal, e.g., a rodent, e.g., a mouse, hamster, or rat.

In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity can be produced and selected. See, e.g., XENOMOUSE™, Green et al. (1994) *Nature Genetics* 7:13-21, U.S. 2003-0070185, WO 96/34096, and WO 96/33735.

In another embodiment, a monoclonal antibody is obtained from the non-human animal, and then modified, e.g., humanized or deimmunized. Winter describes an exemplary CDR-grafting method that can be used to prepare humanized antibodies described herein (U.S. Pat. No. 5,225,539). All or some of the CDRs of a particular human antibody can be replaced with at least a portion of a non-human antibody. In one embodiment, it is only necessary to replace the CDRs required for binding or binding determinants of such CDRs to arrive at a useful humanized antibody that binds to an antigen.

Humanized antibodies can be generated by replacing sequences of the Fv variable region that are not directly involved in antigen binding with equivalent sequences from human Fv variable regions. General methods for generating humanized antibodies are provided by Morrison, S. L. (1985) *Science* 229:1202-1207, by Oi et al. (1986) *BioTechniques* 4:214, and by U.S. Pat. Nos. 5,585,089; 5,693,761; 5,693,762; 5,859,205; and 6,407,213. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, can be obtained from a hybridoma producing an antibody against a predetermined target, as described above, from germline immunoglobulin genes, or from synthetic constructs. The recombinant DNA encoding the humanized antibody can then be cloned into an appropriate expression vector. In one embodiment, the expression vector comprises a polynucleotide encoding a glutamine synthetase polypeptide. (See, e.g., Porter et al., *Biotechnol Prog* 26(5):1446-54 (2010).)

The antibody can include a human Fc region, e.g., a wild-type Fc region or an Fc region that includes one or more alterations. In one embodiment, the constant region is altered, e.g., mutated, to modify the properties of the antibody (e.g., to increase or decrease one or more of: Fc receptor binding, antibody glycosylation, the number of cysteine residues, effector cell function, or complement function). For example, the human IgG1 constant region can be mutated at one or more residues, e.g., one or more of residues 234 and 237. Antibodies can have mutations in the CH2 region of the heavy chain that reduce or alter effector function, e.g., Fc receptor binding and complement activation. For example, antibodies can have mutations such as those described in U.S. Pat. Nos. 5,624,821 and 5,648,260. Antibodies can also have mutations that stabilize the disulfide bond between the two heavy chains of an immunoglobulin, such as mutations in the hinge region of IgG4, as disclosed in the art (e.g., Angal et al. (1993) *Mol. Immunol.* 30:105-08). See also, e.g., U.S. 2005-0037000.

In other embodiments, the antibody can be modified to have an altered glycosylation pattern (i.e., altered from the original or native glycosylation pattern). As used in this context, "altered" means having one or more carbohydrate moieties deleted, and/or having one or more glycosylation sites added to the original antibody. Addition of glycosylation sites to the presently disclosed antibodies can be accomplished by altering the amino acid sequence to contain glycosylation site consensus sequences; such techniques are well known in the art. Another means of increasing the number of carbohydrate moieties on the antibodies is by chemical or enzymatic coupling of glycosides to the amino acid residues of the antibody. These methods are described in, e.g., WO 87/05330, and Aplin and Wriston (1981) *CRC Crit. Rev. Biochem.* 22:259-306. Removal of any carbohydrate moieties present on the antibodies can be accomplished chemically or enzymatically as described in the art (Hakimuddin et al. (1987) *Arch. Biochem. Biophys.* 259:52; Edge et al. (1981) *Anal. Biochem.* 118:131; and Thotakura et al. (1987) *Meth. Enzymol.* 138:350). See, e.g., U.S. Pat. No. 5,869,046 for a modification that increases in vivo half-life by providing a salvage receptor binding epitope.

The antibodies can be in the form of full length antibodies, or in the form of fragments of antibodies, e.g., Fab, F(ab')$_2$, Fd, dAb, and scFv fragments. Additional forms include a protein that includes a single variable domain, e.g., a camel or camelized domain. See, e.g., U.S. 2005-0079574 and Davies et al. (1996) *Protein Eng.* 9(6):531-7.

In one embodiment, the antibody is an antigen-binding fragment of a full length antibody, e.g., a Fab, F(ab')2, Fv or a single chain Fv fragment. Typically, the antibody is a full length antibody. The antibody can be a monoclonal antibody or a mono-specific antibody.

In another embodiment, the antibody can be a human, humanized, CDR-grafted, chimeric, mutated, affinity matured, deimmunized, synthetic or otherwise in vitro-generated antibody, and combinations thereof.

The heavy and light chains of the antibody can be substantially full-length. The protein can include at least one, and preferably two, complete heavy chains, and at least one, and preferably two, complete light chains) or can include an antigen-binding fragment (e.g., a Fab, F(ab')2, Fv or a single chain Fv fragment). In yet other embodiments, the antibody has a heavy chain constant region chosen from, e.g., IgG1, IgG2, IgG3, IgG4, IgM, IgA1, IgA2, IgD, and IgE; particularly, chosen from, e.g., IgG1, IgG2, IgG3, and IgG4, more particularly, IgG1 (e.g., human IgG1). Typically, the heavy chain constant region is human or a modified form of a human constant region. In another embodiment, the antibody has a light chain constant region chosen from, e.g., kappa or lambda, particularly, kappa (e.g., human kappa).

Receptors

Another class of polypeptides that have been shown to be effective as pharmaceutical and/or commercial agents includes receptors. Receptors are typically trans-membrane glycoproteins that function by recognizing an extra-cellular signaling ligand. Receptors typically have a protein kinase domain in addition to the ligand recognizing domain, which initiates a signaling pathway by phosphorylating target intracellular molecules upon binding the ligand, leading to developmental or metabolic changes within the cell. In one embodiment, the receptors of interest are modified so as to remove the transmembrane and/or intracellular domain(s), in place of which there can optionally be attached an Ig-domain. In one embodiment, receptors to be produced in accordance with the present invention are receptor tyrosine kinases (RTKs). The RTK family includes receptors that are crucial for a variety of functions numerous cell types (see, e.g., Yarden and Ullrich, *Ann. Rev. Biochem.* 57:433-478, 1988; Ullrich and Schlessinger, *Cell* 61:243-254, 1990, incorporated herein by reference). Non-limiting examples of RTKs include members of the fibroblast growth factor (FGF) receptor family, members of the epidermal growth factor receptor (EGF) family, platelet derived growth factor (PDGF) receptor, tyrosine kinase with immunoglobulin and EGF homology domains-1 (TIE-1) and TIE-2 receptors (Sato et al., *Nature* 376(6535):70-74 (1995), incorporated herein by reference) and c-Met receptor, some of which have been suggested to promote angiogenesis, directly or indirectly (Mustonen and Alitalo, *J. Cell Biol.* 129:895-898, 1995). Other non-limiting examples of RTK's include fetal liver kinase 1 (FLK-1) (sometimes referred to as kinase insert domain-containing receptor (KDR) (Terman et al., *Oncogene* 6:1677-83, 1991) or vascular endothelial cell growth factor receptor 2 (VEGFR-2)), fms-like tyrosine kinase-1 (Flt-1) (DeVries et al. *Science* 255; 989-991, 1992; Shibuya et al., *Oncogene* 5:519-524, 1990), sometimes referred to as vascular endothelial cell growth factor receptor 1 (VEGFR-1), neuropilin-1, endoglin, endosialin, and Ax1. Those of ordinary skill in the art will be aware of other receptors that can be expressed in accordance with the present invention.

Growth Factors and Other Signaling Molecules

Another class of polypeptides that have been shown to be effective as pharmaceutical and/or commercial agents includes growth factors and other signaling molecules. Growth factors are typically glycoproteins that are secreted by cells and bind to and activate receptors on other cells, initiating a metabolic or developmental change in the receptor cell.

Non-limiting examples of mammalian growth factors and other signaling molecules include cytokines; epidermal growth factor (EGF); platelet-derived growth factor (PDGF); fibroblast growth factors (FGFs) such as aFGF and bFGF; transforming growth factors (TGFs) such as TGF-alpha and TGF-beta, including TGF-beta 1, TGF-beta 2, TGF-beta 3, TGF-beta 4, or TGF-beta 5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; tumor necrosis factor (TNF) alpha and beta; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin, hemopoietic growth factor; enkephalinase; RANTES (regulated on activation normally T-cell expressed and secreted); human macrophage inflammatory protein (MIP-1-alpha); mullerian-inhibiting substance; relaxin A-chain; relaxin B-chain; prorelaxin; mouse gonadotropin-associated peptide; neurotrophic factors such as bone-derived neurotrophic factor (BDNF), neurotrophin-3, -4, -5, or -6 (NT-3, NT-4, NT-5, or NT-6), or a nerve growth factor such as NGF-beta. One of ordinary skill in the art will be aware of other growth factors or signaling molecules that can be expressed in accordance with the present invention.

G-Protein Coupled Receptors

Another class of polypeptides that have been shown to be effective as pharmaceutical and/or commercial agents includes growth factors and other signaling molecules. G-protein coupled receptors (GPCRs) are proteins that have seven transmembrane domains. Upon binding of a ligand to a GPCR, a signal is transduced within the cell which results in a change in a biological or physiological property of the cell.

GPCRs, along with G-proteins and effectors (intracellular enzymes and channels which are modulated by G-proteins), are the components of a modular signaling system that connects the state of intracellular second messengers to extracellular inputs. These genes and gene-products are potential causative agents of disease.

The GPCR protein superfamily now contains over 250 types of paralogues, receptors that represent variants generated by gene duplications (or other processes), as opposed to orthologues, the same receptor from different species. The superfamily can be broken down into five families: Family I, receptors typified by rhodopsin and the beta2-adrenergic receptor and currently represented by over 200 unique members; Family II, the recently characterized parathyroid hormone/calcitonin/secretin receptor family; Family III, the metabotropic glutamate receptor family in mammals; Family IV, the cAMP receptor family, important in the chemotaxis and development of D. discoideum; and Family V, the fungal mating pheromone receptors such as STE2.

Cells

Any eukaryotic cell or cell type susceptible to cell culture can be utilized in accordance with the present invention. For example, plant cells, yeast cells, animal cells, insect cells, avian cells or mammalian cells can be utilized in accordance with the present invention. In one embodiment, the eukaryotic cells are capable of expressing a recombinant protein or are capable of producing a recombinant or reassortant virus.

Non-limiting examples of mammalian cells that can be used in accordance with the present invention include BALB/c mouse myeloma line (NSO/1, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); baby hamster kidney cells (BHK, ATCC CCL 10); Chinese hamster ovary cells ±DHFR (CHO, Urlaub and Chasin, *Proc. Natl. Acad. Sci.* USA, 77:4216 (1980)); mouse sertoli cells (TM4, Mather, *Biol. Reprod.*, 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL5 1); TRI cells (Mather et al., *Annals N.Y. Acad. Sci.,* 383:44-68 (1982)); MRC 5 cells; FS4 cells; and a human hepatoma line (Hep G2). In one embodiment, the present invention is used in the culturing of and expression of polypeptides from CHO cell lines. In a specific embodiment, the CHO cell line is the DG44 CHO cell line. In a specific embodiment, the CHO cell line is the DUXB11 CHO cell line. In a specific embodiment, the CHO cell line comprises a vector comprising a polynucleotide encoding a glutamine synthetase polypeptide. In a further specific embodiment, the CHO cell line expresses an exogenous glutamine synthetase gene. (See, e.g., Porter et al., *Biotechnol Prog* 26(5):1446-54 (2010).)

Additionally, any number of commercially and non-commercially available hybridoma cell lines that express polypeptides or proteins can be utilized in accordance with the present invention. One skilled in the art will appreciate that hybridoma cell lines might have different nutrition requirements and/or might require different culture conditions for optimal growth and polypeptide or protein expression, and will be able to modify conditions as needed.

The eukaryotic cells according to the present invention can be selected or engineered to produce high levels of protein or polypeptide, or to produce large quantities of virus. Often, cells are genetically engineered to produce high levels of protein, for example by introduction of a gene encoding the recombinant glycoprotein of interest and/or by introduction of control elements that regulate expression of the gene (whether endogenous or introduced) encoding the recombinant glycoprotein of interest.

The eukaryotic cells can also be selected or engineered to survive in culture for extended periods of time. For example, the cells can be genetically engineered to express a polypeptide or polypeptides that confer extended survival on the cells. In one embodiment, the eukaryotic cells comprise a transgene encoding the Bcl-2 polypeptide or a variant thereof. See, e.g., U.S. Pat. No. 7,785,880. In a specific embodiment, the cells comprise a polynucleotide encoding the bcl-xL polypeptide. See, e.g., Chiang G G, Sisk W P. 2005. *Biotechnology and Bioengineering* 91(7): 779-792.

The eukaryotic cells can also be selected or engineered to modify its posttranslational modification pathways. In one embodiment, the cells are selected or engineered to modify a protein glycolsylation pathway. In a specific embodiment, the cells are selected or engineered to express an aglycosylated protein, e.g., an aglycosylated recombinant antibody. In another specific embodiment, the cells are selected or engineered to express an afucosylated protein, e.g., an afucosylated recombinant antibody.

The eukaryotic cells can also be selected or engineered to allow culturing in serum free medium.

Media

The cell culture of the present invention is prepared in any medium suitable for the particular cell being cultured. In some embodiments, the medium contains e.g., inorganic salts, carbohydrates (e.g., sugars such as glucose, galactose, maltose or fructose), amino acids, vitamins (e.g., B group vitamins (e.g., B12), vitamin A vitamin E, riboflavin, thiamine and biotin), fatty acids and lipids (e.g., cholesterol and steroids), proteins and peptides (e.g., albumin, transferrin, fibronectin and fetuin), serum (e.g., compositions comprising albumins, growth factors and growth inhibitors, such as, fetal bovine serum, newborn calf serum and horse serum), trace elements (e.g., zinc, copper, selenium and tricarboxylic acid intermediates), hydrolysates (hydrolyzed proteins derived from plant or animal sources), and combinations thereof. Commercially available media such as 5×-concentrated DMEM/F12 (Invitrogen), CD OptiCHO feed (Invitrogen), CD EfficientFeed (Invitrogen), Cell Boost (HyClone), BalanCD CHO Feed (Irvine Scientific), BD Recharge (Becton Dickinson), Cellvento Feed (EMD Millipore), Ex-cell CHOZN Feed (Sigma-Aldrich), CHO Feed Bioreactor Supplement (Sigma-Aldrich), SheffCHO (Kerry), Zap-CHO (Invitria), ActiCHO (PAA/GE Healthcare), Ham's F10 (Sigma), Minimal Essential Medium ([MEM], Sigma), RPMI-1640 (Sigma), and Dulbecco's Modified Eagle's Medium ([DMEM], Sigma) are exemplary nutrient solutions. In addition, any of the media described in Ham and Wallace, (1979) *Meth. Enz.,* 58:44; Barnes and Sato, (1980) *Anal. Biochem.,* 102:255; U.S. Pat. Nos. 4,767, 704; 4,657,866; 4,927,762; 5,122,469 or 4,560,655; International Publication Nos. WO 90/03430; and WO 87/00195; the disclosures of all of which are incorporated herein by reference, can be used as culture media. Any of these media can be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as gentamycin), trace elements (defined as inorganic compounds usually present at final concentrations in the micromolar range) lipids (such as linoleic or other fatty acids) and their suitable carriers, and glucose or an equivalent energy source. In some embodiments the nutrient media is serum-free media, a protein-free media, or a chemically defined media. Any other necessary supplements can also be included at appropriate concentrations that would be known to those skilled in the art.

In one embodiment, the mammalian host cell is a CHO cell and a suitable medium contains a basal medium component such as a DMEM/HAM F-12 based formulation (for composition of DMEM and HAM F12 media, see culture media formulations in American Type Culture Collection Catalogue of Cell Lines and Hybridomas, Sixth Edition, 1988, pages 346-349) with modified concentrations of some components such as amino acids, salts, sugar, and vitamins, recombinant human insulin, hydrolyzed peptone, such as Primatone HS or Primatone RL (Sheffield, England), or the equivalent; a cell protective agent, such as Pluronic F68 or the equivalent pluronic polyol; gentamycin; and trace elements.

The present invention provides a variety of media formulations that, when used in accordance with other culturing steps described herein, minimize or prevent decreases in cellular viability in the culture while retaining the ability to manipulate, alter, or change glycosylation of a recombinant glycoprotein of interest.

A media formulation of the present invention that has been shown to be to useful in manipulating glycosylation, while not having greatly negative impacts on metabolic balance, cell growth and/or viability or on expression of polypeptide or protein comprises the media supplements described herein. One of ordinary skill in the art will understand that the media formulations of the present invention encompass both defined and non-defined media.

Cell Culture Processes

Various methods of preparing mammalian cells for production of proteins or polypeptides by batch and fed-batch culture are well known in the art. A nucleic acid sufficient to achieve expression (typically a vector containing the gene encoding the polypeptide or protein of interest and any operably linked genetic control elements) can be introduced into the host cell line by any number of well-known techniques. Typically, cells are screened to determine which of the host cells have actually taken up the vector and express the polypeptide or protein of interest. Traditional methods of detecting a particular polypeptide or protein of interest expressed by mammalian cells include but are not limited to immunohistochemistry, immunoprecipitation, flow cytometry, immunofluorescence microscopy, SDS-PAGE, Western blots, enzyme-linked immunosorbentassay (ELISA), high performance liquid chromatography (HPLC) techniques, biological activity assays and affinity chromatography. One of ordinary skill in the art will be aware of other appropriate techniques for detecting expressed polypeptides or proteins. If multiple host cells express the polypeptide or protein of interest, some or all of the listed techniques can be used to determine which of the cells expresses that polypeptide or protein at the highest levels.

Once a cell that expresses the polypeptide or protein of interest has been identified, the cell is propagated in culture by any of the variety of methods well-known to one of ordinary skill in the art. The cell expressing the polypeptide of interest is typically propagated by growing it at a temperature and in a medium that is conducive to the survival, growth and viability of the cell. The initial culture volume can be of any size, but is often smaller than the culture volume of the production bioreactor used in the final production of the polypeptide or protein of interest, and frequently cells are passaged several times in bioreactors of increasing volume prior to seeding the production bioreactor. The cell culture can be agitated or shaken to increase oxygenation of the medium and dispersion of nutrients to the cells. Alternatively or additionally, special sparging devices that are well known in the art can be used to increase and control oxygenation of the culture. In accordance with the present invention, one of ordinary skill in the art will understand that it can be beneficial to control or regulate certain internal conditions of the bioreactor, including but not limited to pH, temperature, oxygenation, etc.

The cell density useful in the methods of the present invention can be chosen by one of ordinary skill in the art. In accordance with the present invention, the cell density can be as low as a single cell per culture volume. In some embodiments of the present invention, starting cell densities (seed density) can range from about $2 \times 10^2$ viable cells per mL to about $2 \times 10^3$, $2 \times 10^4$, $2 \times 10^5$, $2 \times 10^6$, $5 \times 10^6$ or $10 \times 10^6$ viable cells per mL and higher.

In accordance with the present invention, a cell culture size can be any volume that is appropriate for production of polypeptides. In one embodiment, the volume of the cell culture is at least 500 liters. In other embodiments, the volume of the production cell culture is 10, 50, 100, 250, 1000, 2000, 2500, 5000, 8000, 10,000, 12,000 liters or more, or any volume in between. For example, a cell culture will be 10 to 5,000 liters, 10 to 10,000 liters, 10 to 15,000 liters, 50 to 5,000 liters, 50 to 10,000 liters, or 50 to 15,000 liters, 100 to 5,000 liters, 100 to 10,000 liters, 100 to 15,000 liters, 500 to 5,000 liters, 500 to 10,000 liters, 500 to 15,000 liters, 1,000 to 5,000 liters, 1,000 to 10,000 liters, or 1,000 to 15,000 liters. Or a cell culture will be between about 500 liters and about 30,000 liters, about 500 liters and about 20,000 liters, about 500 liters and about 10,000 liters, about 500 liters and about 5,000 liters, about 1,000 liters and about 30,000 liters, about 2,000 liters and about 30,000 liters, about 3,000 liters and about 30,000 liters, about 5,000 liters and about 30,000 liters, or about 10,000 liters and about 30,000 liters, or a cell culture will be at least about 500 liters, at least about 1,000 liters, at least about 2,000 liters, at least about 3,000 liters, at least about 5,000 liters, at least about 10,000 liters, at least about 15,000 liters, or at least about 20,000 liters.

One of ordinary skill in the art will be aware of and will be able to choose a suitable culture size for use in practicing the present invention. The production bioreactor for the culture can be constructed of any material that is conducive to cell growth and viability that does not interfere with expression or stability of the produced polypeptide or protein.

The temperature of the cell culture will be selected based primarily on the range of temperatures at which the cell culture remains viable. For example, during the initial growth phase, CHO cells grow well at 37° C. In general, most mammalian cells grow well within a range of about 25° C. to 42° C.

In one embodiment of the present invention, the temperature of the initial growth phase is maintained at a single, constant temperature. In another embodiment, the temperature of the initial growth phase is maintained within a range of temperatures. For example, the temperature can be steadily increased or decreased during the initial growth phase. Alternatively, the temperature can be increased or decreased by discrete amounts at various times during the initial growth phase. One of ordinary skill in the art will be able to determine whether a single or multiple temperatures should be used, and whether the temperature should be adjusted steadily or by discrete amounts.

The cells can be grown during the initial growth phase for a greater or lesser amount of time, depending on the needs of the practitioner and the requirement of the cells themselves. In one embodiment, the cells are grown for a period of time sufficient to achieve a viable cell density that is a given percentage of the maximal viable cell density that the cells would eventually reach if allowed to grow undisturbed. For example, the cells can be grown for a period of time sufficient to achieve a desired viable cell density of 1, 5, 10, 15, 20, 25, 30, 35, 40, 45, 50, 55, 60, 65, 70, 75, 80, 85, 90, 95 or 99 percent of maximal viable cell density.

In another embodiment the cells are allowed to grow for a defined period of time. For example, depending on the starting concentration of the cell culture, the temperature at which the cells are grown, and the intrinsic growth rate of the cells, the cells can be grown for 0, 1, 2, 3, 4, 5, 6, 7, 8, 9, 10, 11, 12, 13, 14, 15, 16, 17, 18, 19, 20 or more days. In some cases, the cells can be allowed to grow for a month or more. In one embodiment, the growth phase is between about 1 day and about 20 days, about 1 day and about 15 days, about 1 day and about 14 days, about 1 day and about 13 days, about 1 day and about 12 days, about 1 day and about 11 days, about 1 day and about 10 days, about 1 day and about 9 days, about 1 day and about 8 days, about 1 day and about 7 days, about 1 day and about 6 days, about 1 day and about 5 days, about 1 day and about 4 days, about 1 day and about 3 days, about 2 days and about 15 days, about 3 days and about 15 days, about 4 days and about 15 days, about 5 days and about 15 days, about 6 days and about 15 days, about 7 days and about 15 days, about 8 days and about 15 days, about 9 days and about 15 days, about 10 days and about 15 days, about 2 days and about 20 days, about 3 days and about 20 days, about 4 days and about 20 days, about 5 days and about 20 days, about 6 days and about 20 days, about 7 days and about 20 days, about 8 days and about 20 days, about 9 days and about 20 days, about 10 days and about 20 days, or about 10 days and about 20 days. In another embodiment, the growth phase is at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 15 days, or at least about 20 days. In a further embodiment, the growth phase is about 1 day, about 2 days, about 3 days, about 4 days, about 5 days, about 6 days, about 7 days, about 8 days, about 9 days, about 10 days, about 11 days, about 12 days, about 15 days, or about 20 days.

The cells would be grown for 0 days in the production bioreactor if their growth in a seed bioreactor, at the initial growth phase temperature, was sufficient that the viable cell density in the production bioreactor at the time of its inoculation is already at the desired percentage of the maximal viable cell density. The practitioner of the present invention will be able to choose the duration of the initial growth phase depending on polypeptide or protein production requirements and the needs of the cells themselves.

The cell culture can be agitated or shaken during the initial culture phase in order to increase oxygenation and dispersion of nutrients to the cells. In accordance with the present invention, one of ordinary skill in the art will understand that it can be beneficial to control or regulate certain internal conditions of the bioreactor during the initial growth phase, including but not limited to pH, temperature, oxygenation, etc. For example, pH can be controlled by supplying an appropriate amount of acid or base and oxygenation can be controlled with sparging devices that are well known in the art.

In one embodiment, at the end of the initial growth phase, at least one of the culture conditions is shifted so that a second set of culture conditions is applied. The shift in culture conditions can be accomplished by a change in the temperature, pH, osmolality or chemical inductant level of the cell culture. In one embodiment, the culture conditions are shifted by shifting the temperature of the culture.

When shifting the temperature of the culture, the temperature shift can be relatively gradual. For example, it can take several hours or days to complete the temperature change. Alternatively, the temperature shift can be relatively abrupt. For example, the temperature change can be complete in less than several hours. Given the appropriate production and control equipment, such as is standard in the commercial large-scale production of polypeptides or proteins, the temperature change can even be complete within less than an hour.

The temperature of the cell culture in the subsequent growth phase will be selected based primarily from the range of temperatures at which the cell culture remains viable and expresses recombinant polypeptides or proteins at commercially adequate levels with the desired level of glycosylation. In general, most mammalian cells remain viable and express recombinant polypeptides or proteins at commercially adequate levels within a range of about 25° C. to 42° C. In one embodiment, mammalian cells remain viable and express recombinant polypeptides or proteins at commercially adequate levels within a range of about 25° C. to 35° C. Those of ordinary skill in the art will be able to select appropriate temperature or temperatures in which to grow cells, depending on the needs of the cells and the production requirements of the practitioner.

In accordance with the present invention, once the conditions of the cell culture have been shifted as discussed above, the cell culture is maintained for a subsequent production phase under a second set of culture conditions conducive to the survival and viability of the cell culture and appropriate for expression of the desired polypeptide or protein at commercially adequate levels.

As discussed above, the culture can be shifted by shifting one or more of a number of culture conditions including, but not limited to, temperature, pH, osmolality, and sodium butyrate levels. In one embodiment, the temperature of the culture is shifted. According to this embodiment, during the subsequent production phase, the culture is maintained at a temperature or temperature range that is lower than the temperature or temperature range of the initial growth phase. For example, during the subsequent production phase, CHO cells express recombinant polypeptides and proteins well within a range of 25° C. to 35° C.

In accordance with the present invention, the cells can be maintained in the subsequent production phase until a desired cell density or production titer is reached. In one embodiment, the cells are maintained in the subsequent production phase until the titer to the recombinant polypeptide or protein reaches a maximum. In other embodiments, the culture can be harvested prior to this point, depending on the production requirement of the practitioner or the needs of the cells themselves. For example, the cells can be maintained for a period of time sufficient to achieve a viable cell density of 1, 5, 10, 15, 20, 25, 30, 35, 40, 45, 50, 55, 60, 65, 70, 75, 80, 85, 90, 95 or 99 percent of maximal viable cell density. In some cases, it is desirable to allow the viable cell density to reach a maximum, and then allow the viable cell density to decline to some level before harvesting the culture. In an extreme example, it can be desirable to allow the viable cell density to approach or reach zero before harvesting the culture.

In another embodiment of the present invention, the cells are allowed to grow for a defined period of time during the subsequent production phase. For example, depending on the concentration of the cell culture at the start of the subsequent growth phase, the temperature at which the cells are grown, and the intrinsic growth rate of the cells, the cells can be grown for 1, 2, 3, 4, 5, 6, 7, 8, 9, 10, 11, 12, 13, 14, 15, 16, 17, 18, 19, 20 or more days. In some cases, the cells can be allowed to grow for a month or more. The practitioner of the present invention will be able to choose the duration of the subsequent production phase depending on polypeptide or protein production requirements and the needs of the cells themselves.

In certain cases, it can be beneficial or necessary to supplement the cell culture during the growth and/or subsequent production phase with nutrients or other medium components that have been depleted or metabolized by the cells. For example, it might be advantageous to supplement the cell culture with nutrients or other medium components observed to have been depleted. Alternatively or additionally, it can be beneficial or necessary to supplement the cell culture prior to the subsequent production phase. As non-limiting examples, it can be beneficial or necessary to supplement the cell culture with hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, or glucose or other energy source.

These supplementary components, including the amino acids, can all be added to the cell culture at one time, or they can be provided to the cell culture in a series of additions. In one embodiment of the present invention, the supplementary components are provided to the cell culture at multiple times in proportional amounts. In another embodiment, it can be desirable to provide only certain of the supplementary components initially, and provide the remaining components at a later time. In yet another embodiment of the present invention, the cell culture is fed continually with these supplementary components.

In accordance with the present invention, the total volume added to the cell culture should optimally be kept to a minimal amount. For example, the total volume of the medium or solution containing the supplementary components added to the cell culture can be 1, 2, 3, 4, 5, 6, 7, 8, 9, 10, 15, 20, 25, 30, 35, 40, 45 or 50% of the volume of the cell culture prior to providing the supplementary components.

The cell culture can be agitated or shaken during the subsequent production phase in order to increase oxygenation and dispersion of nutrients to the cells. In accordance with the present invention, one of ordinary skill in the art will understand that it can be beneficial to control or regulate certain internal conditions of the bioreactor during the subsequent growth phase, including but not limited to pH, temperature, oxygenation, etc. For example, pH can be controlled by supplying an appropriate amount of acid or base and oxygenation can be controlled with sparging devices that are well known in the art.

In certain embodiments of the present invention, the practitioner can find it beneficial or necessary to periodically monitor particular conditions of the growing cell culture. Monitoring cell culture conditions allows the practitioner to determine whether the cell culture is producing recombinant polypeptide or protein at suboptimal levels or whether the culture is about to enter into a suboptimal production phase.

In order to monitor certain cell culture conditions, it will be necessary to remove small aliquots of the culture for analysis. One of ordinary skill in the art will understand that such removal can potentially introduce contamination into the cell culture, and will take appropriate care to minimize the risk of such contamination.

As non-limiting example, it can be beneficial or necessary to monitor temperature, pH, cell density, cell viability, integrated viable cell density, lactate levels, ammonium levels, osmolarity, or titer of the expressed polypeptide or protein. Numerous techniques are well known in the art that will allow one of ordinary skill in the art to measure these conditions. For example, cell density can be measured using a hemacytometer, a Coulter counter, or Cell density examination (CEDEX). Viable cell density can be determined by staining a culture sample with Trypan blue. Since only dead cells take up the Trypan blue, viable cell density can be determined by counting the total number of cells, dividing the number of cells that take up the dye by the total number of cells, and taking the reciprocal. HPLC can be used to determine the levels of lactate, ammonium or the expressed polypeptide or protein. Alternatively, the level of the expressed polypeptide or protein can be determined by standard molecular biology techniques such as coomassie staining of SDS-PAGE gels, Western blotting, Bradford assays, Lowry assays, Biuret assays, and UV absorbance. It can also be beneficial or necessary to monitor the posttranslational modifications of the expressed polypeptide or protein, including phosphorylation and glycosylation.

The practitioner can also monitor the metabolic status of the cell culture, for example, by monitoring the glucose, lactate, ammonium, and amino acid concentrations in the cell culture, as well as by monitoring the oxygen production or carbon dioxide production of the cell culture. For example, cell culture conditions can be analyzed by using NOVA Bioprofile 100 or 400 (NOVA Biomedical, WA).

Additionally, the practitioner can monitor the metabolic state of the cell culture by monitoring the activity of mitochondria. In embodiment, mitochondrial activity can be monitored by monitoring the mitochondrial membrane potential using Rhodamine 123. Johnson L V, Walsh M L, Chen L B. 1980. *Proceedings of the National Academy of Sciences* 77(2):990-994.

Isolation of Expressed Polypeptide

In general, it will typically be desirable to isolate and/or purify proteins or polypeptides expressed according to the present invention. In one embodiment, the expressed polypeptide or protein is secreted into the medium and thus cells and other solids can be removed, as by centrifugation or filtering for example, as a first step in the purification process.

Alternatively, the expressed polypeptide can be bound to the surface of the host cell. In this embodiment, the media is removed and the host cells expressing the polypeptide or protein are lysed as a first step in the purification process. Lysis of mammalian host cells can be achieved by any number of means well known to those of ordinary skill in the art, including physical disruption by glass beads and exposure to high pH conditions.

The polypeptide can be isolated and purified by standard methods including, but not limited to, chromatography (e.g., ion exchange, affinity, size exclusion, and hydroxyapatite chromatography), gel filtration, centrifugation, or differential solubility, ethanol precipitation or by any other available technique for the purification of proteins (See, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol 182), Academic Press, 1997, all incorporated herein by reference). For immunoaffinity chromatography in particular, the protein can be isolated by binding it to an affinity column comprising antibodies that were raised against that protein and were affixed to a stationary support. Alternatively, affinity tags such as an influenza coat sequence, poly-histidine, or glutathione-S-transferase can be attached to the protein by standard recombinant techniques to allow for easy purification by passage over the appropriate affinity column. Protease inhibitors such as phenyl methyl sulfonyl fluoride (PMSF), leupeptin, pepstatin or aprotinin can be added at any or all stages in order to reduce or eliminate degradation of the polypeptide or protein during the purification process. Protease inhibitors are particularly desired when cells must be lysed in order to isolate and purify the expressed polypeptide or protein. One of ordinary skill in the art will appreciate that the exact purification technique will vary depending on the character of the polypeptide or protein to be purified, the character of the cells from which the polypeptide or protein is expressed, and the composition of the medium in which the cells were grown.

Pharmaceutical Compositions

A polypeptide can be formulated as a pharmaceutical composition for administration to a subject, e.g., to treat or prevent a disorder or disease. Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The composition can include a pharmaceutically acceptable salt, e.g., an acid addition salt or a base addition salt (See e.g., Berge, S. M., et al. (1977) *Pharm. Sci.* 66:1-19). In one embodiment, a pharmaceutical composition is an immunogenic composition comprising a virus produced in accordance with methods described herein.

Pharmaceutical formulation is a well-established art, and is further described, e.g., in Gennaro (ed.), Remington. The Science and Practice of Pharmacy, 20$^{th}$ ed., Lippincott, Williams & Wilkins (2000) (ISBN: 0683306472); Ansel et al., Pharmaceutical Dosage Forms and Drug Delivery Systems, 7$^{th}$ Ed., Lippincott Williams & Wilkins Publishers (1999) (ISBN: 0683305727); and Kibbe (ed.), Handbook of Pharmaceutical Excipients American Pharmaceutical Association, 3$^{rd}$ ed. (2000) (ISBN: 091733096X).

The pharmaceutical compositions can be in a variety of forms. These include, for example, liquid, semi-solid and solid dosage forms, such as liquid solutions (e.g., injectable and infusible solutions), dispersions or suspensions, tablets, pills, powders, liposomes and suppositories. The form can depend on the intended mode of administration and therapeutic application. Typically compositions for the agents described herein are in the form of injectable or infusible solutions.

In one embodiment, the antibody is formulated with excipient materials, such as sodium chloride, sodium dibasic phosphate heptahydrate, sodium monobasic phosphate, and a stabilizer. It can be provided, for example, in a buffered solution at a suitable concentration and can be stored at 2-8° C.

Such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, the methods of preparation are vacuum drying and freeze drying that yield a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the polypeptide can be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., Sustained and Controlled Release Drug Delivery Systems, J. R. Robinson, ed., Marcel Dekker, Inc., New York (1978).

The foregoing description is to be understood as being representative only and is not intended to be limiting. Alternative methods and materials for implementing the invention and also additional applications will be apparent to one of skill in the art, and are intended to be included within the accompanying claims.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., Sambrook et al., ed., Cold Spring Harbor Laboratory Press: (1989); *Molecular Cloning: A Laboratory Manual*, Sambrook et al., ed., Cold Springs Harbor Laboratory, New York (1992), *DNA Cloning*, D. N. Glover ed., Volumes I and II (1985); *Oligonucleotide Synthesis*, M. J. Gait ed., (1984); Mullis et al. U.S. Pat. No. 4,683,195; *Nucleic Acid Hybridization*, B. D. Hames & S. J. Higgins eds. (1984); *Transcription And Translation*, B. D. Hames & S. J. Higgins eds. (1984); *Culture Of Animal Cells*, R. I. Freshney, Alan R. Liss, Inc., (1987); *Immobilized Cells And Enzymes*, IRL Press, (1986); B. Perbal, *A Practical Guide To Molecular Cloning* (1984); the treatise, *Methods In Enzymology*, Academic Press, Inc., N.Y.; *Gene Transfer Vectors For Mammalian Cells*, J. H. Miller and M. P. Calos eds., Cold Spring Harbor Laboratory (1987); *Methods In Enzymology*, Vols. 154 and 155 (Wu et al. eds.); *Immunochemical Methods In Cell And Molecular Biology*, Mayer and Walker, eds., Academic Press, London (1987); *Handbook Of Experimental Immunology*, Volumes I-IV, D. M. Weir and C. C. Blackwell, eds., (1986); *Manipulating the Mouse Embryo*, Cold Spring Harbor Laboratory Press, Cold Spring Harbor, N.Y., (1986); and in Ausubel et al., *Current Protocols in Molecular Biology*, John Wiley and Sons, Baltimore, Md. (1989).

General principles of antibody engineering are set forth in *Antibody Engineering*, 2nd edition, C. A. K. Borrebaeck, Ed., Oxford Univ. Press (1995). General principles of protein engineering are set forth in *Protein Engineering, A Practical Approach*, Rickwood, D., et al., Eds., IRL Press at Oxford Univ. Press, Oxford, Eng. (1995). General principles of antibodies and antibody-hapten binding are set forth in: Nisonoff, A., *Molecular Immunology*, 2nd ed., Sinauer Associates, Sunderland, Mass. (1984); and Steward, M. W., *Antibodies, Their Structure and Function*, Chapman and Hall, New York, N.Y. (1984). Additionally, standard methods in immunology known in the art and not specifically described are generally followed as in *Current Protocols in Immunology*, John Wiley & Sons, New York; Stites et al. (eds), *Basic and Clinical-Immunology* (8th ed.), Appleton & Lange, Norwalk, Conn. (1994) and Mishell and Shiigi (eds), *Selected Methods in Cellular Immunology*, W.H. Freeman and Co., New York (1980).

Standard reference works setting forth general principles of immunology include *Current Protocols in Immunology*, John Wiley & Sons, New York; Klein, J., Immunology: *The Science of Self-Nonself Discrimination*, John Wiley & Sons, New York (1982); Kennett, R., et al., eds., *Monoclonal Antibodies, Hybridoma: A New Dimension in Biological Analyses*, Plenum Press, New York (1980); Campbell, A., "Monoclonal Antibody Technology" in Burden, R., et al., eds., *Laboratory Techniques in Biochemistry and Molecular Biology*, Vol. 13, Elsevere, Amsterdam (1984), *Kuby Immunology* 4$^{th}$ ed. Ed. Richard A. Goldsby, Thomas J. Kindt and Barbara A. Osborne, H. Freemand & Co. (2000); Roitt, I., Brostoff, J. and Male D., Immunology 6th ed. London: Mosby (2001); Abbas A., Abul, A. and Lichtman, A., *Cellular and Molecular Immunology* Ed. 5, Elsevier Health Sciences Division (2005); Kontermann and Dubel, *Antibody Engineering*, Springer Verlan (2001); Sambrook and Russell, *Molecular Cloning: A Laboratory Manual*. Cold Spring Harbor Press (2001); Lewin, Genes VIII, Prentice Hall (2003); Harlow and Lane, *Antibodies: A Laboratory Manual*, Cold Spring Harbor Press (1988); Dieffenbach and Dveksler, *PCR Primer* Cold Spring Harbor Press (2003).

All of the references cited above, as well as all references cited herein, are incorporated herein by reference in their entireties.

EXAMPLES

The following materials and methods are provided for the experiments outlined below.

Cell line: The cell line used in this study produced a growth factor receptor immunoadhesin polypeptide. The cell line was constructed using DG44 adapted to grow in serum-free medium (Prentice, 2007). The cell line DUXB11 was also used in this study.

Cell culture methods: Cells were thawed and maintained as in a previous report (Kshirsagar, et al. 2012 Biotechnol Bioeng, Huang, et al. *Biotechnology Progress* 26(5):1400-1410 (2010)). Basal medium for thaw and passing was the same as in previous reports (Kshirsagar/Huang). Briefly, cells were thawed and maintained in 3 L shake flasks (Corning Life Sciences, Corning, N.Y.) with 1 L working volumes and were passaged every 2-3 days. For maintenance cultures the incubator was controlled at 37° C. and 5% CO2.

Bioreactor culture conditions: Fed batch cultures were performed in 5 L glass Applikon vessels using Finesse TruBio DV controllers (Finesse Solutions, San Jose, Calif.) with an initial working volume between 2-2.5 L. Bioreactors were seeded at constant seed density of 4×10$^5$ cells/ml. Concentrated feed medium was delivered on days 3, 5, and every day or every other day following through harvest. Temperature was maintained at 35° C. or 36° C. and pH was controlled at 7.1+/−0.2 by the addition of either 1 M sodium carbonate or carbon dioxide. Dissolved oxygen was maintained at 30%-40% by air and oxygen sparge using a drilled hole sparger. Agitation was maintained between 200-400 RPM throughout the culture to limit total gas flow, while an overlay was maintained between 0.005 and 0.04 vvm.

Offline analysis: Samples were taken on most days and analyzed with a variety of equipment. Cell density and viability were measured using the standard technique of trypan blue exclusion using a Cedex (Roche Innovatis AG, Germany). Cell viability and growth rate of the various cultures were measured during the culture time course at specific days post-inoculation.

Example 1—Effect of Copper (II) Sulfate, Hypoxanthine, Glucosamine, and Galactose on Cell Culture Performance Copper (II) sulfate, hypoxanthine, guanine, glucosamine, and galactose were delivered to two different immunoadhesin-expressing CHO cell cultures either as part of the feed media or as boli from distinct stock solutions. The typical culture process is a 14-day process that consists of a growth phase from Day 0 to Day 6 at 37° C. and a protein production phase from Day 6 to Day 14 at 30° C.

Addition of these components to cell culture media negatively affected the culture density or viability as compared to the control condition to various degrees (FIG. 1A, FIG. 1B, FIG. 2A, FIG. 2B, FIG. 3A, FIG. 3B, FIG. 4A, FIG. 4B, FIG. 5A, FIG. 5B). The data provided is segregated based on the cell line and format/type of culture vessel used (shake flask versus bioreactor).

Example 2—Effect of Glucosamine and Galactose on the Percentage of Afucose and NGNA The effects of glucosamine and galactose were examined using both CHO-043 cells (Table 1) and CHO-602 (Table 2). In CHO-043 cells, glucosamine alone greatly reduced sialylation from 12 mol/chain to 6 mol/chain. It also reduced the level of α-gal. The combination of glucosamine and galactose generated control-like sialylation levels while significantly reducing % NGNA. The combination did not generate a significant increase in % α-gal compared to control.

TABLE 1

Effect of glucosamine and galactose on CHO-043 % afucose, % α-gal, sialylation, and % NGNA (fed-batch shake flask). N-glycan and sialylation values were obtained from Day 12 samples purified using ProA purification. N-glycans were then enzymatically removed from purified protein and analyzed using HILIC-UPLC. ProG titer values were also obtained from Day 12 harvest samples.

| CHO-043 Fed-batch Shake Flask | % afucose | TSA (mol/chain) | % NGNA | %α-gal | Titer (g/L) |
|---|---|---|---|---|---|
| Comparator polypeptide | <5.1% | No Data | <1% | <1% | No Data |
| CHO-043 Control | 2.79% | 12.3 | 4.6% | 7.2% | 2.0 |
| 20 mM GlcN (D2, D4 Boli) | 1.7% | 6.6 | 3.8% | 2.4% | 1.8 |
| GlcN and Galactose | 2.1% | 12.0 | 2.2% | 8.1% | 1.9 |

In CHO-602, glucosamine alone had little effect on N-glycan parameters such as % afucose and % NGNA. It did, however, reduce sialylation. But when used in concert with galactose, it reduced % afucose and % NGNA (Table 2).

TABLE 2

Effect of glucosamine and galactose on CHO-602 % afucose, %α-gal, sialylation, and % NGNA (fed-batch shake flask format). N-glycan and sialylation values were obtained from Day 12 samples purified using ProA purification. N-glycans were then enzymatically removed from purified protein and analyzed using HILIC-UPLC. ProG titer values were obtained from Day 14 harvest samples.

| CHO-602 Fed-batch Shake Flask | % afucose | TSA (mol/chain) | % NGNA | Titer (g/L) |
|---|---|---|---|---|
| Comparator polypeptide | <5.1% | No Data | <1% | No Data |
| CHO-602 Control | 9.6 ± 0.3 | 11.8 ± 0.4 | 1.6 ± 0.3 | 1.7 ± 0.1 |
| 10 mM GlcN (D6 Bolus) | 8.9% | 11.1 | 1.3% | 1.4 |
| GlcN and Galactose | 7.5% | 11.7 | 1.1% | 1.5 |

Example 3—Effect of Hypoxanthine and Guanine on FcγRIIIa Binding

Addition of hypoxanthine and guanine to fed-batch shake flask cultures brought the levels of FcγRIIIa binding within the range of a comparator polypeptide produced in a different cell type (Table 3). However, there was no change in the % afucose levels.

TABLE 3

Effect of hypoxanthine alone on % FcγRIIIa binding (fed-batch shake flask). Day 14 samples were two-column purified using ProA and hydrophobic interaction chromatography (HIC). The reported percent binding is relative to Enbrel innovator material. ProG titer values were also obtained from Day 14 harvest samples.

| Fed-batch Shake Flask | % afucose | % FcγRIIIa | Titer (g/L) |
|---|---|---|---|
| Comparator polypeptide | <5.1% | 85-120% | No Data |
| ExptA Control | 9.8% | 125% | 1.8 |
| ExptA 1 mM Hypoxanthine (D6 Bolus) | 9.5% | 85% | 1.7 |
| ExptA 0.2 mM Guanine (D6 Bolus) | 10.5% | 92% | 1.5 |
| ExptB Control | 9.6% | 143% | 1.8 |
| ExptB 1 mM Hypoxanthine (D6 Bolus) | 8.3% | 122% | 1.6 |
| ExptB 0.2 mM Guanine (D6 Bolus) | 10.2% | 121% | 1.6 |

Example 4—Effect of Copper (II) Sulfate on N-Linked Glycosylation

Addition of copper (II) sulfate alone moved % afucose, % galactosylation, and % charged levels of N-linked glycosylation toward values associated with a comparator polypeptide produced in a different mammalian cell (Table 4). These data are significant because typically, it is desirable to increase afucose levels as this has a positive effect on bioactive effects such as % FcγRIIIa binding and ADCC.

TABLE 4

Effect of copper (II) sulfate on N-linked glycosylation (fed-batch shake flask). All N- glycan values were obtained from Day 12 samples purified using ProA purification. N-glycans were then enzymatically removed from purified protein and analyzed using HILIC-UPLC. ProG titer values were obtained from Day 14 harvest samples.

| Fed-batch Shake Flask | % afucose | % galactosylation | % charged | Titer (g/L) |
|---|---|---|---|---|
| Comparator polypeptide | <5.1% | <57.6% | >45.7 | No Data |
| Control (n = 4) | 9.6 ± 0.3 | 73.1 ± 2.3 | 36.7 ± 2.5 | 1.7 ± 0.1 |
| Feed supp. w/ 1 mM CuSO$_4$ | 8.4% | 62.7% | 43.7% | 1.8 |
| 0.2 mM CuSO$_4$ (D6 Bolus) | 8.2% | 70.3% | 42.1% | 1.9 |
| 0.5 mM CuSO$_4$ (D6 Bolus) | 8.2% | 68.5% | 42.4% | 1.9 |

Example 5—Effect of Copper (II) Sulfate, Glucosamine, and Galactose on N-Linked Glycosylation Addition of copper (II) sulfate alone in the bioreactor confirmed the shake flask results (Table 5). Furthermore, the combination of copper (II) sulfate, glucosamine, galactose favorably reduced % afucose, but came at the expense of lower % charged levels. Despite the addition of glucosamine, a known inhibitor of sialylation, sialylation (total sialic acid—TSA) was not significantly lower compared to that of the control conditions. The addition of galactose likely compensated for the TSA-reducing effect of the glucosamine.

TABLE 5

Effect of copper (II) sulfate, glucosamine, and galactose on N-linked glycosylation (bioreactor). N-glycan values were obtained from Day 14 samples purified using ProA purification. N-glycans were then enzymatically removed from purified protein and analyzed using HILIC-UPLC. ProG titer values were obtained from Day 14 harvest samples.

| 3 L Fed-batch Bioreactor | % afucose | % galact. | % charged | % α-gal | TSA (mol/chain) | % NGNA | Titer (g/L) |
|---|---|---|---|---|---|---|---|
| Comparator polypeptide | <5.1% | <57.6% | >45.7% | <1% | No Data | <1% | No Data |
| Control (n = 3) | 8.1 ± 0.6 | 71.9 ± 2.4 | 35.9 ± 2.7 | 1.4 ± 0.4 | 13.3 | 0.8% | 2.0 ± 0.1 |
| Feed w/1 mM CuSO$_4$ | 7.1 | 65.4 | 41.9 | 0.4 | 13.5 | 0.7% | 2.0 |
| CuSO4, GlcN, and Galactose (n = 2) | 5.9 ± 0.8 | 62.4 ± 2.3 | 29.0 ± 5.0 | 0.5 | 12.7 ± 0.4 | 0.8% | 2.0 |

Example 6—Effect of Copper (II) Sulfate and Hypoxanthine on N-Linked Glycosylation The combination of copper (II) sulfate and hypoxanthine brought about the most favorable PQ results (Table 6). The combination simultaneously reduced % afucose, % galactosylation, and % α-gal. $CuSO_4$ and hypoxanthine generated an N-glycan profile that was similar to that generated by $CuSO_4$, glucosamine, and galactose (Table 5), but did not generate an undesired increase in % α-gal. However, the combination had a deleterious effect on cell growth, viability, and resultant titer.

TABLE 6

Effect of copper (II) sulfate and hypoxanthine on N-linked glycosylation (bioreactor). N-glycan values were obtained from Day 14 samples purified using ProA purification. N- glycans were then enzymatically removed from purified protein and analyzed using HILIC-UPLC. ProG titer values were obtained from Day 14 harvest samples.

| 3L Fed-batch Bioreactor | % afucose | % galact. | % charged | %α-gal | Titer (g/L) |
|---|---|---|---|---|---|
| Comparator polypeptide | <5.1% | <57.6% | >45.7% | <1% | No Data |
| Control (n = 3) | 8.1 ± 0.6 | 71.9 ± 2.4 | 35.9 ± 2.7 | 1.4 ± 0.4 | 2.0 ± 0.1 |
| $CuSO_4$ and Hypoxanthine | 6.2% | 58.9% | 40.7% | 0.6% | 1.4 |

TABLE 7

Effect of copper (II) sulfate and Hypoxanthine-Thymidine supplement on CHO-602 N-linked glycosylation (fed-batch shake flask). Culture conditions were describe in FIG. 6A and FIG. 6B. N-glycan values were obtained from Day 14 samples purified using ProA purification. N-glycans were then enzymatically removed from purified protein and analyzed using HILIC-UPLC. ProG titer values were obtained from Day 14 harvest samples.

| CHO-602 Fed-batch SF | % afucose | % galact. | % charged | Titer (g/L) |
|---|---|---|---|---|
| Comparator polypeptide | <5.1% | <57.6% | >45.7% | No Data |
| Control | 9.9% | 72.4% | 26.8% | 2.0 g/L |
| $CuSO_4$ and HT Low | 8.4% | 59.5% | 32.7% | 1.9 g/L |
| $CuSO_4$ and HT High | 8.9% | 49.7% | 31% | 1.7 g/L |

Example 7—Manipulation of Glycosylation

The desirability of each supplementation combination depends on the application. If a product quality attribute is prioritized over the product quality attribute affected by the corresponding side effect, then adding the supplement would still be desirable.

For instance, if reducing afucosylation is a priority and a drop in titer is acceptable, then copper+hypoxanthine becomes desirable as that is one of the combinations that generates a dramatic effect on afucosylation. However, if titer is of greatest importance, then the more desirable solution becomes the copper sulfate itself.

In the overall context of minimizing undesired side effects, the order of desirability is as follows:
1. Copper sulfate
2. Copper sulfate+hypoxanthine+thymidine
3. Copper sulfate+hypoxanthine
4. Copper sulfate+glucosamine+galactose
5. Hypoxanthine
6. Glucosamine+galactose
7. Guanine
8. Glucosamine Reduce % Afucosylation

| Supplement | Desirability | Side Effect | Data |
|---|---|---|---|
| GlcN + Galactose | Low | Unknown sialylated species at HILIC elution times of RT29 and RT34 | Table 1, 2 |
| Copper + GlcN + Galactose | Low | Unknown sialylated species at HILIC elution times of RT29 and RT34 | Table 5 |
| Copper | High | None | Table 4, 5 |
| Copper + Hypoxanthine | Medium | Lower titer | Table 6 |
| Copper + Hypoxanthine + Thymidine | Med-High | Slightly lower titer | Table 7 |

Reduce % Galactosylation

| Supplement | Desirability | Side Effect | Data |
|---|---|---|---|
| Copper | High | None | Table 4, 5 |
| Copper + GlcN + Galactose | Low | Unknown peaks | Table 5 |
| Copper + Hypoxanthine | Medium | Lower titer | Table 6 |
| Copper + Hypoxanthine + Thymidine | Med-High | Slightly lower titer | Table 7 |

Increase % Charged

| Supplement | Desirability | Side Effect | Data |
|---|---|---|---|
| Copper | High | None | Table 4, 5 |
| Copper + Hypoxanthine | Medium | Lower titer | Table 6 |
| Copper + Hypoxanthine + Thymidine | Med-High | Slightly lower titer | Table 7 |

Reduce % α-Gal

| Supplement | Desirability | Side Effect | Data |
|---|---|---|---|
| GlcN | Low | Reduce TSA | Table 1 |

Reduce NGNA

| Supplement | Desirability | Side Effect | Data |
|---|---|---|---|
| GlcN + Galactose | High | None | Table 1 |

Example 8—Effect of Mycophenolic Acid (MPA) on Afucosylation (Desired), and Cell Titer and Cell Viability (Side Effect) in Shake Flask DUXB11 cell lines (cell line #1 and #2) were cultured in 3 L bioreactor respectively for 7 days following the platform process. On day 7, the cells were divided into several 1 L shake flasks with 200 mL working volume and then dosed with various amounts of MPA (0 μM, 10 μM, 30 μM). After dosing MPA, shake flask fed-batch is conducted until day-3 harvest. Filtered supernatant samples were analyzed for titer and N-glycan analysis for afucosylation level. The data showed that an increase in MPA dosing concentration caused an increase in the afucosylation level (desired) (see Table 8 below). However, the titer was decreased (side effect) (see Table 8 below and FIG. 7A and FIG. 7B). The impact on viability was not significant because this is a quick screening study happened in shake flask and cells only got 3 days to expose to MPA. The impact on viability became much more significant in bioreactor process (see Example 9 below).

TABLE 8

Effect of mycophenolic acid supplement on DUXB11 afucosylation (shake flask).

| Total MPA added | Afucosylation (%) | Titer (g/L) | Cell viability (%) |
|---|---|---|---|
| 0 μM | 2.25 | 0.15 | 63.1 |
| 1 μM | 3.85 | 0.136 | 62 |
| 10 μM | 4.9 | 0.106 | 61 |
| 30 μM | 4.4 | 0.105 | 62 |

Example 9—Effect of Mycophenolic Acid (MPA) Afucosylation (Desired) and Cell Titer and Cell Viability (Side Effect) in a Bioreactor DUXB11 cell lines were cultured in 3 L bioreactor respectively following the platform process. On day 6, various amounts of MPA were dosed (0 μM and 5 μM). After dosing MPA, bioreactors were kept running until they were harvested on day 13. Filtered supernatant samples were analyzed for titer and N-glycan analysis for afucosylation level. The data showed that MPA dosing addition increased afucosylation level (desired), but decreased the cell viability and the titer (side effect), which is the same trend as that in shake flask study.

TABLE 9

Effect of mycophenolic acid supplement on DUXB11 afucosylation (bioreactor).

| Total MPA added | Afucosylation (%) | Titer (g/L) | Cell viability (%) |
|---|---|---|---|
| 0 μM | 2.7 | 0.24 | 42 |
| 5 μM | 8.3 | 0.28 | 25 |

Example 10—Effect of the Timing of Supplementation with Mycophenolic Acid (MPA)

The culture conditions are described in FIG. 8. The data showed that the addition of MPA on the day of peak variable cell density (VCD) had a significant impact on afucosylation, while the addition of MPA on the different day of peak VCD had non-significant impact on afucosylation. In addition, afucosylation level was increased with peak VCD day MPA addition (fixed 5 μM MPA vs. VCD based MPA addition). Data indicated that MPA dosing time is much more important than dosing amount.

Example 11—Effect of Seed Density on Cell Growth and Afucosylation

The culture conditions are described in FIG. 9A, FIG. 9B, and FIG. 10. The data showed different cell performances due to different seed density (FIG. 9A and FIG. 9B). The data also showed that the seed density could change the MPA impact on afucosylation level even though the same MPA amount was added (FIG. 10). Normally, the seed density and afucosylation are in inverse proportion. The similar study was carried out using another DUXB11 cell line, the same trend was observed.

Example 12—Effect of Insulin on Afucosylation and Titer

The culture conditions are described in FIG. 11. The data showed that increasing insulin concentration, with same MPA supplementation, led to increased afucosylation in fed-batch culture (Table 10A and 10B below, and FIG. 11).

TABLE 10A

Effect of insulin and MPA supplement on DUXB11 afucosylation.

| Total insulin added | Afucosylation (%) | Titer (g/L) |
|---|---|---|
| 11 mg/L | 4.9 | 2.3 |
| 13 mg/L | 6.2 | 2.6 |
| 17 mg/L | 8.1 | 2.8 |
| 24 mg/L | 7.8 | 3.1 |

TABLE 10B

Glycosylation map after insulin and MPA supplement on DUXB11.

| | M3F | G0 | G0F | MS | G1 + G1' | G1F + G1F' | M6 | G2 | G2F | Afucosyl | FcgRIII a binding |
|---|---|---|---|---|---|---|---|---|---|---|---|
| Min | 0.4 | 3.4 | 37.1 | 0.8 | 1.1 | 26.0 | | 0.0 | 2.4 | 5.0 | 79 |
| Max | 4.3 | 5.5 | 54.1 | 3.8 | 4.0 | 42.9 | | 0.9 | 7.8 | 9.6 | 136 |
| 2.5 mg/L ins in feed 1 | 1.0 | 3.9 | 68.1 | 2.2 | 0.9 | 20.2 | 0.90 | 0.0 | 1.8 | 4.9 | 60 |
| 10 mg/L ins in feed 1 | 0.9 | 5.1 | 64.9 | 2.2 | 1.1 | 21.7 | 0.9 | 0.0 | 2.3 | 6.2 | 71 |
| 30 mg/L ins in feed 1 | 0.9 | 6.7 | 62.5 | 2.4 | 1.3 | 21.1 | 1.1 | 0.0 | 2.3 | 8.1 | 100 |
| 60 mg/L ins in feed 1 | 0.8 | 6.4 | 61.4 | 2.5 | 1.4 | 22.9 | 0.9 | 0.0 | 2.6 | 7.8 | 100 |

Example 13—Effect of Temperature on Afucosylation (Desired) and Titer, Viability (Side Effects)

The effect of temperature shift and supplementation with MPA is provided in FIG. 12, FIG. 13, FIG. 14A, and FIG. 14B and Table 11 below.

TABLE 11

Effect of temperature and MPA supplementation (Day 5) on DUXB11 afucosylation.

| Temperature (° C.) | Afucosylation (%) | Titer (g/L) | Cell viability (%) |
|---|---|---|---|
| 35 to 30 | 11.9 | 1.5 | 43 |
| 35 to 33 | 10.7 | 1.8 | 29 |

Example 14—Effect of Seed Density on Cell Growth and Afucosylation

The effect supplementation with MPA on cell growth, cell viability, viable cell density, and titer is provided in FIG. 15A, FIG. 15B, FIG. 15C, FIG. 16A, FIG. 16B, FIG. 16C, FIG. 17A, FIG. 17B, and FIG. 17C.

Example 15—Effect of Mycophenolic Acid (MPA) and Mycophenolic Acid Acyl Glucuronide (acMPAG) on Afucosylation in Shake Flask BIIB603 cell line was scaled up to 5 L BR for fed-batch production process. On day 5, temperature was shifted from 37° C. to 31° C. On day 6, cell culture was drained from the bioreactor and divided into several 500 mL shake flasks with 100 mL working volume and then dosed with various amounts of MPA (0 µM, 20 µM, 40 µM) or acMPAG (20 µM) in duplicates. After dosing, the shake flasks were cultured another 4 days at 31° C., 5% $CO_2$ and 150 rpm with fed-batch process and then harvested. The supernatant was sent for PQ assay (N-glycan analysis) for afucosylation level.

The data showed that an increase in MPA dosing concentration caused an increase in the afucosylation level, and that acMPAG dosing also increased the afucosylation level to similar extent (FIG. 18).

The present invention is not to be limited in scope by the specific embodiments described which are intended as single illustrations of individual aspects of the invention, and any compositions or methods which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

All documents, articles, publications, patents, and patent applications mentioned in this specification are herein incorporated by reference to the same extent as if each individual publication or patent application was specifically and individually indicated to be incorporated by reference.

What is claimed is:

1. A method of altering the glycosylation pattern of a recombinant glycoprotein produced in cell culture comprising:
   culturing eukaryotic cells engineered to express a recombinant glycoprotein of interest in a cell culture medium, wherein the cell culture medium is supplemented with an additive comprising mycophenolic acid;
   wherein the glycosylation pattern of the recombinant glycoprotein of interest is altered relative to the same recombinant glycoprotein produced by the same cells in the same cell culture medium without the additive;
   wherein the recombinant glycoprotein of interest comprises at least a portion of: an antibody, an immunoadhesin, a Transforming Growth Factor (TGF) beta superfamily signaling molecule, a blood clotting factor, antibody against TNFR, antibody against growth factor receptors (HER2), TNFR:Fc, combinations thereof, or fragments thereof.

2. The method of claim 1 wherein the glycosylation pattern of the recombinant glycoprotein of interest is altered to better resemble the glycosylation pattern of a reference sample of the glycoprotein.

3. The method of claim 1, further comprising recovering the recombinant glycoprotein of interest from the cell culture.

4. The method of claim 1, wherein the alteration of the glycosylation pattern of the recombinant glycoprotein of interest comprises an increased level of afucosylation.

5. The method of claim 1, wherein the alteration of the glycosylation pattern is achieved without increasing the level of α-gal.

6. The method of claim 1, wherein the alteration of the glycosylation pattern is achieved without reducing sialic acid levels.

7. The method of claim 1, wherein the cell culture comprises a growth phase and a protein production phase, and wherein the additive is introduced into the culture medium before or at the same time as the initiation of the protein production phase.

8. The method of claim 1, wherein the cell culture is conducted in a shake flask.

9. The method of claim 1, wherein the cell culture is conducted in a stirred-tank bioreactor.

10. The method of claim 9, wherein the bioreactor has a volume of between about 500 liters and about 30,000 liters.

11. The method of claim 1, wherein the eukaryotic cells engineered to express the recombinant glycoprotein of interest are selected from the group consisting of CHO cells, HEK cells, NSO cells, PER.C6 cells, 293 cells, HeLa cells, and MDCK cells.

12. The method of claim 1, wherein the eukaryotic cells engineered to express the recombinant glycoprotein of interest are hybridoma cells.

13. The method of claim 1, wherein the eukaryotic cells engineered to express the recombinant glycoprotein of interest have been adapted to grow in serum free medium, animal protein free medium or chemically defined medium.

14. The method of claim 1, wherein the antibody comprises an antibody Fc region, an antigen-binding domain of an antibody, a full antibody, a chimeric antibody, a humanized antibody or human antibody, or a human IgG1 antibody.

15. The method of claim 1, wherein the immunoadhesin comprises a tumor necrosis factor receptor.

16. The method of claim 1, wherein the total amount of recombinant glycoprotein produced in the additive-supplemented cell culture medium is equal to the total amount of recombinant glycoprotein produced by the corresponding unsupplemented cell culture medium.

17. The method of claim 1, wherein the total amount of recombinant glycoprotein produced in the additive-supplemented cell culture medium is decreased by less than 20% of the total amount of recombinant glycoprotein produced by the corresponding unsupplemented cell culture medium.

18. The method of claim 1, wherein the specific productivity of the engineered eukaryotic cells maintained in the additive-supplemented cell culture medium is equal to the specific productivity of the same cells maintained in the corresponding unsupplemented cell culture medium.

19. The method of claim 1, wherein the cell culture is a perfusion culture.

20. The method of claim 1, wherein the supplemented cell culture medium comprises between 1 μM and 50 μM mycophenolic acid.

21. The method of claim 20, wherein the mycophenolic acid is introduced into the cell culture medium as part of a feed medium, or as one or more boli from a distinct stock solution.

22. The method of claim 1, wherein the method further comprises controlling or modulating cell culture temperature.

23. The method of claim 22, wherein the cell culture temperature is about 25 to about 42° C.

24. The method of claim 22, wherein the mycophenolic acid is introduced at the same time as the cell culture temperature is controlled or modulated.

25. The method of claim 22, wherein the mycophenolic acid is introduced at a different time than the time when the cell culture temperature is controlled or modulated.

26. The method of claim 1, wherein the method further comprises controlling or modulating cell culture seed density.

27. A method of altering the glycosylation pattern of a recombinant glycoprotein produced in cell culture comprising:

culturing eukaryotic cells engineered to express a recombinant glycoprotein of interest in a cell culture medium, wherein the cell culture medium is supplemented with an additive comprising mycophenolic acid;

wherein the glycosylation pattern of the recombinant glycoprotein of interest is altered relative to the same recombinant glycoprotein produced by the same cells in the same cell culture medium without the additive;

wherein the eukaryotic cells engineered to express the recombinant glycoprotein of interest are hybridoma cells.

28. A method of altering the glycosylation pattern of a recombinant glycoprotein produced in cell culture comprising:

culturing eukaryotic cells engineered to express a recombinant glycoprotein of interest in a cell culture medium, wherein the cell culture medium is supplemented with an additive comprising mycophenolic acid;

wherein the glycosylation pattern of the recombinant glycoprotein of interest is altered relative to the same recombinant glycoprotein produced by the same cells in the same cell culture medium without the additive;

wherein the cell culture is a perfusion culture.

* * * * *